United States Patent
Hampapuram et al.

(10) Patent No.: US 10,702,215 B2
(45) Date of Patent: *Jul. 7, 2020

(54) SYSTEMS AND METHODS FOR DYNAMICALLY AND INTELLIGENTLY MONITORING A HOST'S GLYCEMIC CONDITION AFTER AN ALERT IS TRIGGERED

(71) Applicant: DexCom, Inc., San Diego, CA (US)

(72) Inventors: Hari Hampapuram, Portland, OR (US); Anna Leigh Davis, Cardiff by the Sea, CA (US); Naresh C. Bhavaraju, San Diego, CA (US); Apurv Ullas Kamath, San Diego, CA (US); Claudio Cobelli, Padua (IT); Giovanni Sparacino, Padua (IT); Andrea Facchinetti, Padua (IT); Chiara Zecchin, Pernumia (IT)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/674,979

(22) Filed: Nov. 5, 2019

(65) Prior Publication Data

US 2020/0060630 A1 Feb. 27, 2020

Related U.S. Application Data

(63) Continuation of application No. 16/172,550, filed on Oct. 26, 2018, now Pat. No. 10,555,705, which is a
(Continued)

(51) Int. Cl.
*A61B 5/00* (2006.01)
*A61B 5/145* (2006.01)
*G06F 19/00* (2018.01)

(52) U.S. Cl.
CPC .......... *A61B 5/746* (2013.01); *A61B 5/0004* (2013.01); *A61B 5/0022* (2013.01);
(Continued)

(58) Field of Classification Search
CPC ...... A61B 5/746; A61B 5/0004; A61B 5/0022; A61B 5/0031; A61B 5/14503;
(Continued)

(56) References Cited

U.S. PATENT DOCUMENTS

| | | |
|---|---|---|
| 5,299,571 A | 4/1994 | Mastrototaro |
| 5,390,671 A | 2/1995 | Lord et al. |

(Continued)

FOREIGN PATENT DOCUMENTS

| | | |
|---|---|---|
| EP | 1077634 B1 | 2/2001 |
| EP | 1078258 B1 | 2/2001 |

(Continued)

OTHER PUBLICATIONS

Arnold et al., IEEE Transactions on Biomedical Engineering, 45(5):553-562 (1998); "Adaptive AR Modeling of Nonstationary by Means of Kalman Filtering".

(Continued)

*Primary Examiner* — Kerri L McNally
(74) *Attorney, Agent, or Firm* — Knobbe, Martens, Olson & Bear, LLP

(57) ABSTRACT

Systems and methods for providing sensitive and specific alarms indicative of glycemic condition are provided herein. In an embodiment, a method of processing sensor data by a continuous analyte sensor includes: evaluating sensor data using a first function to determine whether a real time glucose value meets a first threshold; evaluating sensor data using a second function to determine whether a predicted glucose value meets a second threshold; activating a hypoglycemic indicator if either the first threshold is met or if the second threshold is predicted to be met; and providing an output based on the activated hypoglycemic indicator.

29 Claims, 18 Drawing Sheets

Related U.S. Application Data continuation of application No. 15/486,704, filed on Apr. 13, 2017, now Pat. No. 10,143,426, which is a continuation of application No. 14/720,668, filed on May 22, 2015, now Pat. No. 9,655,565, which is a continuation of application No. 13/742,841, filed on Jan. 16, 2013, now Pat. No. 9,119,529, which is a continuation of application No. 13/742,694, filed on Jan. 16, 2013, now Pat. No. 9,119,528.

(60) Provisional application No. 61/720,286, filed on Oct. 30, 2012.

(52) U.S. Cl.
CPC ........ *A61B 5/0031* (2013.01); *A61B 5/14503* (2013.01); *A61B 5/14532* (2013.01); *A61B 5/4848* (2013.01); *A61B 5/4866* (2013.01); *A61B 5/7221* (2013.01); *A61B 5/7275* (2013.01); *G06F 19/00* (2013.01); *A61B 5/002* (2013.01)

(58) Field of Classification Search
CPC . A61B 5/14532; A61B 5/4848; A61B 5/4866; A61B 5/7221; A61B 5/7275; A61B 5/002
USPC ..................................................... 340/573.1
See application file for complete search history.

(56) References Cited

U.S. PATENT DOCUMENTS

| | | |
|---|---|---|
| 5,568,806 A | 10/1996 | Cheney et al. |
| 5,586,553 A | 12/1996 | Halili et al. |
| 5,680,858 A | 10/1997 | Hansen et al. |
| 5,851,197 A | 12/1998 | Marano et al. |
| 5,971,922 A | 10/1999 | Arita et al. |
| 5,993,411 A | 11/1999 | Choi |
| 6,093,172 A | 7/2000 | Funderburk et al. |
| 6,180,416 B1 | 1/2001 | Kurnik et al. |
| 6,197,001 B1 | 3/2001 | Wilson et al. |
| 6,212,424 B1 | 4/2001 | Robinson |
| 6,236,872 B1 | 5/2001 | Diab et al. |
| 6,254,586 B1 | 7/2001 | Mann et al. |
| 6,272,364 B1 | 8/2001 | Kurnik |
| 6,293,925 B1 | 9/2001 | Safabash et al. |
| 6,424,847 B1 | 7/2002 | Mastrototaro et al. |
| 6,544,212 B2 | 4/2003 | Galley et al. |
| 6,546,269 B1 | 4/2003 | Kurnik |
| 6,553,244 B2 | 4/2003 | Lesho et al. |
| 6,558,351 B1 | 5/2003 | Steil et al. |
| 6,560,471 B1 | 5/2003 | Heller et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,577,899 B2 | 6/2003 | Lebel et al. |
| 6,579,690 B1 | 6/2003 | Bonnecaze et al. |
| 6,607,509 B2 | 8/2003 | Bobroff et al. |
| 6,653,091 B1 | 11/2003 | Dunn et al. |
| 6,656,114 B1 | 12/2003 | Poulsen et al. |
| 6,695,860 B1 | 2/2004 | Ward et al. |
| 6,740,518 B1 | 5/2004 | Duong et al. |
| 6,882,940 B2 | 4/2005 | Potts et al. |
| 6,895,263 B2 | 5/2005 | Shin et al. |
| 6,990,366 B2 | 1/2006 | Say et al. |
| 6,991,619 B2 | 1/2006 | Marano-Ford et al. |
| 6,991,620 B2 | 1/2006 | Marano-Ford et al. |
| 6,997,907 B2 | 2/2006 | Safabash et al. |
| 7,003,336 B2 | 2/2006 | Holker et al. |
| 7,003,341 B2 | 2/2006 | Say et al. |
| 7,022,072 B2 | 4/2006 | Fox et al. |
| 7,022,108 B2 | 4/2006 | Marano-Ford et al. |
| 7,029,444 B2 | 4/2006 | Shin et al. |
| 7,190,988 B2 | 3/2007 | Say et al. |
| 7,207,974 B2 | 4/2007 | Safabash et al. |
| 7,228,162 B2 | 6/2007 | Ward et al. |
| 7,282,029 B1 | 10/2007 | Poulsen et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,343,188 B2 | 3/2008 | Sohrab |
| 7,381,184 B2 | 6/2008 | Funderburk et al. |
| 7,384,397 B2 | 6/2008 | Zhang et al. |
| 7,389,133 B1 | 6/2008 | Kotulla et al. |
| 7,399,277 B2 | 7/2008 | Saidara et al. |
| 7,402,153 B2 | 7/2008 | Steil et al. |
| 7,494,465 B2 | 2/2009 | Brister et al. |
| 7,582,059 B2 | 9/2009 | Funderburk et al. |
| 7,602,310 B2 | 10/2009 | Mann et al. |
| 7,618,369 B2 | 11/2009 | Hayter et al. |
| 7,630,748 B2 | 12/2009 | Budiman |
| 7,647,237 B2 | 1/2010 | Malave et al. |
| 7,653,425 B2 | 1/2010 | Hayter et al. |
| 7,654,956 B2 | 2/2010 | Brister et al. |
| 7,660,615 B2 | 2/2010 | Van Antwerp et al. |
| 7,670,288 B2 | 3/2010 | Sher |
| 7,682,338 B2 | 3/2010 | Griffin |
| 7,686,787 B2 | 3/2010 | Moberg et al. |
| 7,695,434 B2 | 4/2010 | Malecha |
| 7,697,967 B2 | 4/2010 | Stafford |
| 7,699,807 B2 | 4/2010 | Faust et al. |
| 7,704,229 B2 | 4/2010 | Moberg et al. |
| 7,729,737 B2 | 6/2010 | Ward |
| 7,731,657 B2 | 6/2010 | Stafford |
| 7,731,659 B2 | 6/2010 | Malecha |
| 7,736,310 B2 | 6/2010 | Taub |
| 7,736,338 B2 | 6/2010 | Kavazov et al. |
| 7,736,344 B2 | 6/2010 | Moberg et al. |
| 7,740,613 B2 | 6/2010 | Yokoi et al. |
| 7,744,589 B2 | 6/2010 | Mounce et al. |
| 7,762,793 B2 | 7/2010 | Gray et al. |
| H2246 H | 8/2010 | Miller et al. |
| 7,766,830 B2 | 8/2010 | Fox et al. |
| 7,768,386 B2 | 8/2010 | Hayter et al. |
| 7,771,393 B2 | 8/2010 | Liniger et al. |
| 7,774,038 B2 | 8/2010 | Wang et al. |
| 7,783,442 B2 | 8/2010 | Mueller et al. |
| 7,785,293 B2 | 8/2010 | Gray et al. |
| 7,789,857 B2 | 9/2010 | Moberg et al. |
| 7,815,569 B2 | 10/2010 | Kovatchev et al. |
| 7,815,607 B2 | 10/2010 | Rutti et al. |
| 7,846,132 B2 | 12/2010 | Gravesen et al. |
| 7,850,652 B2 | 12/2010 | Liniger et al. |
| 7,860,544 B2 | 12/2010 | Say et al. |
| 7,866,026 B1 | 1/2011 | Wang et al. |
| 7,869,853 B1 | 1/2011 | Say et al. |
| 7,871,394 B2 | 1/2011 | Halbert et al. |
| 7,878,975 B2 | 2/2011 | Liljeryd et al. |
| 7,885,698 B2 | 2/2011 | Feldman |
| 7,890,295 B2 | 2/2011 | Shin et al. |
| 7,895,740 B2 | 3/2011 | Wang et al. |
| 7,899,545 B2 | 3/2011 | John |
| 7,912,655 B2 | 3/2011 | Power et al. |
| 7,912,674 B2 | 3/2011 | Killoren-Clark et al. |
| 7,920,907 B2 | 4/2011 | McGarraugh et al. |
| 7,946,985 B2 | 5/2011 | Mastrototaro et al. |
| 7,970,449 B2 | 6/2011 | Ward |
| 7,976,466 B2 | 7/2011 | Ward |
| 7,981,034 B2 | 7/2011 | Jennewine et al. |
| 7,988,630 B1 | 8/2011 | Osorio et al. |
| 7,996,158 B2 | 8/2011 | Hayter et al. |
| 8,103,456 B2 | 1/2012 | Doniger et al. |
| 8,103,471 B2 | 1/2012 | Hayter |
| 8,129,173 B2 | 3/2012 | Shapiro et al. |
| 8,135,548 B2 | 3/2012 | Breton et al. |
| 8,219,173 B2 | 7/2012 | Budiman et al. |
| 8,224,415 B2 | 7/2012 | Budiman |
| 8,260,558 B2 | 9/2012 | Hayter et al. |
| 8,273,022 B2 | 9/2012 | Say et al. |
| 9,119,528 B2 * | 9/2015 | Cobelli .............. A61B 5/0022 |
| 9,655,565 B2 | 5/2017 | Hampapuram et al. |
| 10,143,426 B2 | 12/2018 | Hampapuram |
| 2005/0004439 A1 | 1/2005 | Shin et al. |
| 2005/0027182 A1 | 2/2005 | Siddiqui et al. |

(56) References Cited

U.S. PATENT DOCUMENTS

| | | | |
|---|---|---|---|
| 2005/0177035 A1* | 8/2005 | Botvinick | A61B 5/14532 600/347 |
| 2008/0033254 A1 | 2/2008 | Karnath et al. | |
| 2008/0314395 A1 | 12/2008 | Kovatchev et al. | |
| 2009/0005666 A1 | 1/2009 | Shin et al. | |
| 2009/0105636 A1 | 4/2009 | Hayter et al. | |
| 2009/0160656 A1 | 6/2009 | Seetharaman et al. | |
| 2010/0137699 A1 | 6/2010 | Sher | |
| 2011/0098548 A1 | 4/2011 | Budiman et al. | |
| 2011/0106011 A1* | 5/2011 | Cinar | A61B 5/14532 604/151 |
| 2011/0184267 A1* | 7/2011 | Duke | A61B 5/14532 600/365 |
| 2011/0193704 A1* | 8/2011 | Harper | A61B 5/7275 340/573.1 |
| 2011/0225112 A1* | 9/2011 | Cameron | G06F 19/3456 706/20 |
| 2014/0012511 A1 | 1/2014 | Mensinger et al. | |

FOREIGN PATENT DOCUMENTS

| | | |
|---|---|---|
| EP | 1102559 B1 | 5/2001 |
| EP | 1119637 B1 | 8/2001 |
| EP | 1144028 B1 | 10/2001 |
| EP | 1437674 B1 | 7/2004 |
| EP | 1473050 B1 | 11/2004 |
| EP | 1503660 B1 | 2/2005 |
| EP | 1518495 B1 | 3/2005 |
| EP | 1703839 B1 | 9/2006 |
| EP | 1706022 B1 | 10/2006 |
| EP | 1759201 B1 | 3/2007 |
| EP | 1890597 B1 | 2/2008 |
| EP | 1927602 B1 | 6/2008 |
| EP | 1931253 B1 | 6/2008 |
| EP | 2051620 B1 | 4/2009 |
| EP | 2069771 B1 | 6/2009 |
| WO | WO 1999/058051 | 11/1999 |
| WO | WO 2002/082989 | 10/2002 |
| WO | WO 2005 065538 | 7/2005 |
| WO | WO 2008/042918 | 4/2008 |
| WO | WO 2009/136372 | 12/2009 |
| WO | WO 2011/051922 | 5/2011 |
| WO | WO 2013/090731 | 6/2013 |
| WO | WO 2013/128912 | 9/2013 |
| WO | WO 2014/011488 | 1/2014 |

OTHER PUBLICATIONS

Bremer et al., Diabetes, 48:445-451, (Mar. 1999); "Is Blood Glucose Predictable From Previous Values? A Solicitation for Data".

Choleau et al., Biosensors & Bioelectronics, 17:641-646, (2002); "Calibration of a subcutaneous amperometric glucose sensor part 1: Effect of measurement of uncertainties on the determination of sensor sensitivity and background current".

Choleau et al., Biosensors & Bioelectronics, 17:647-654, (2002); "Calibration of a subcutaneous amperometric glucose sensor implanted for 7 days in diabetic patients part 2: Superiority of the one-point calibration method".

Commenges, Daniel, IEEE Transactions on Automatic Control, 29(3):229-243, (1984); "The deconvolution problem: fast algorithms including the preconditioned conjugate-gradient to compute a MAP Estimator".

Dassau et al, Diabetes Care, 33(6):1249-1254, (Jun. 2010); "Real-Time Hypoglycemia Prediction Suite Using Continuous Glucose Monitoring".

DiNicolao et al., Automatica, 33(5):851-870, (1997); "Nonparametric Input Estimation in Physiological Systems: Problems, Methods and Case Studies".

Eren-Oruklu et al., Diabetes Technology & Therapeutics, 11(4):243-253, (2009); "Estimation of Future Glucose Concentrations with Subject-Specific Recursive Linear Models".

Eren-Oruklu et al., Journal of Diabetes Science and Technology, 4(1):25-33, (Jan. 2010); "Hypoglycemia Prediction with Subject-Specific Recursive Time-Series Models".

Facchinetti et al., IEEE Transactions on Biomedical Engineering, 57(3):634, (2010); "An online self-tunable method to denoise CGM sensor data".

Facchinetti et al., IEEE Transactions on Biomedical Engineering, 58(9):2664, (2011); "Online denoising method to handle intra-individual variability of signal-to-noise ratio in continuous glucose monitoring".

Freeland et al., Annals of Biomedical Engineering, 27:525-537, (1999); "Inference of blood glucose concentrations from subcutaneous glucose concentrations: applications to glucose Biosensors".

Gani et al., IEEE Transactions on Biomedical Engineering, 56(2):246-254, (Feb. 2009); "Predicting Subcutaneous Glucose Concentration in Humans: Data-Driven Glucose Modeling".

Gani et al., IEEE Transactions on Information Technology in Biomedicine, 14(1):157-165, (Jan. 2010); "Universal Glucose Models for Predicting Subcutaneous Glucose Concentration in Humans".

Guerra et al., Diabetes Technology & Therapeutics, 13(8):843-852, (2011); "A Dynamic Risk Measure from Continuous Glucose Monitoring Data".

Guerra et al., IEEE Transactions on Biomedical Engineering, 59(6):1658-1669, (2012); "Enhancing the accuracy of subcutaneous glucose sensors: a real-time deconvolution-based a real-time devconvolution-based approach".

http://en.wikipedia.org/wiki/Spectral_density; (Jan. 29, 2013); Spectral Density.

King et al., J. Diab. Sci. Tech., 1(1):36, (2007); "A prospective evaluation of insulin dosing recommendations in patients with type 1 diabetes at near normal glucose control: Basal Dosing".

Kovatchev et al., Journal of Theoretical Medicine, 3:1-10, (2000); "Risk Analysis of Blood Glucose Data: A Quantitative Approach to Optimizing the Control of Insulin Dependent Diabetes".

Leal et al., J. Diab. Sci. Tech., 4(2):391, (2010); "Real-time glucose estimation algorithm for continuous glucose monitoring using autoregressive models".

Lu et al., et al., Transactions on Biomedical Engineering, 57(8):1839-1846, (Aug. 2010); "The Importance of Different Frequency Bands in Predicting Subcutaneous Glucose Concentration in Type 1 Diabetic Patients".

Palerm et al., 2007, J. Diabetes Sciences and Technology, 1(5):624-629; "Hypoglycemia detection and prediction using continuous glucose monitoring—a study on hypoglycemic clamp data".

Panteleon et al., Diabetes Technology & Therapeutics, 5(3):401-410, (2003); "The role of the independent variable to glucose sensor calibration".

Perez-Gandia et al., Networking Research Center on Bioengineering, Biomaterials and Nano-medicine (CIBER-BBN), Madrid, Spain (2007); "Artificial Neural Network Algorithm for On-Line Glucose Prediction from Continuous Glucose Monitoring".

Phillips, D.L., J. Assoc. Comput., Mach. 9:84-97, (1962); "A technique for the numerical solution of certain integral equations of the first kind".

Rebrin et al., J. Diabetes Sci. Tech., 4(5):1087, (2010); "Use of subcutaneous interstitial fluid glucose to estimate blood glucose: revisiting delay and sensor offset".

Reifman et al., Journal of Diabetes Science and Technology, 1(4):478-486, (Jul. 2007); "Predictive Monitoring for Improved Management of Glucose Levels".

Sandham et al., 1998, IX European Signal Processing Conference; 1998, pp. 673-676; "Blood glucose prediction for diabetes therapy using a recurrent artificial neural network".

Sparacino et al., IEEE Transactions on Biomedical Engineering, 43(5):512-529, (1996); "A Stochastic Deconvolution Method to Reconstruct Insulin Secretion Rate After a Glucose Stimulus".

Sparacino et al., IEEE Transactions on Biomedical Engineering, 54(5):931-937, (May 2007); "Glucose Concentration can be Predicted Ahead in Time from Continuous Glucose Monitoring Sensor Time-Series".

(56) References Cited

OTHER PUBLICATIONS

Tarvainen, M.P., IEEE Transactions on Biomedical Engineering, 51(3):516-524, (2004); "Estimates of nonstationary EEG with Kalman smoother approach: An application to event-related Synchronization (ERS)".

Tikhonov, A.N., Soviet Method. Dokl., 4:1035-1038, (1963); "Solution of incorrectly formulated problems and the regularization method".

* cited by examiner

SYSTEMS AND METHODS FOR DYNAMICALLY AND INTELLIGENTLY MONITORING A HOST'S GLYCEMIC CONDITION AFTER AN ALERT IS TRIGGERED

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/172,550, filed Oct. 26, 2018, which is a continuation of U.S. application Ser. No. 15/486,704, filed Apr. 13, 2017, now U.S. Pat. No. 10,143,426, which is a continuation of U.S. application Ser. No. 14/720,668, filed May 22, 2015, now U.S. Pat. No. 9,655,565, which is a continuation of U.S. application Ser. No. 13/742,841, filed Jan. 16, 2013, now U.S. Pat. No. 9,119,529, which is a continuation of U.S. application Ser. No. 13/742,694, filed Jan. 16, 2013, now U.S. Pat. No. 9,119,528, which claims the benefit of U.S. Provisional Application No. 61/720,286, filed Oct. 30, 2012. Each of the aforementioned applications is incorporated by reference herein in its entirety, and each is hereby expressly made a part of this specification.

BACKGROUND

The present systems and methods relate to processing analyte sensor data from a continuous analyte sensor. More particularly, the present systems and methods relate to providing accurate predictive alarms to a user.

DESCRIPTION OF RELATED ART

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose (SMBG) monitor, which typically requires uncomfortable finger pricks to obtain blood samples for measurement. Due to the lack of comfort and convenience associated with finger pricks, a person with diabetes normally only measures his or her glucose levels two to four times per day. Unfortunately, time intervals between measurements can be spread far enough apart that the person with diabetes finds out too late of a hyperglycemic or hypoglycemic condition, sometimes incurring dangerous side effects. It is not only unlikely that a person with diabetes will take a timely SMBG value, it is also likely that he or she will not know if his or her blood glucose value is going up (higher) or down (lower) based on conventional methods. Diabetics thus may be inhibited from making educated insulin therapy decisions.

Another device that some diabetics use to monitor their blood glucose is a continuous analyte sensor. A continuous analyte sensor typically includes a sensor that is placed subcutaneously, transdermally (e.g., transcutaneously), or intravascularly. The sensor measures the concentration of a given analyte within the body, and generates a signal that is transmitted to electronics associated with the sensor.

One of the major perceived benefits of a continuous analyte sensor is the ability of these devices to have alarms to alert the diabetic user of hyperglycemic or hypoglycemic events before they occur. Additionally, it is desirable for these alarms to be accurate, so that a user does not become de-sensitized from their alarm going off, such that they ignore it because it has become a nuisance. The present disclosure addresses these needs.

SUMMARY

The present systems and methods relate to processing analyte sensor data. Provided herein are systems and methods that allow a user to receive alerts or alarms indicative of glycemic condition in a more accurate and useful way. Consequently, the user may have an improved user experience using such systems and methods.

In a first aspect, a method of activating a hypoglycemic indicator based on continuous glucose sensor data is provided, the method comprising: evaluating sensor data using a first function to determine whether a real time glucose value meets one or more first criteria; evaluating sensor data using a second function to determine whether a predicted glucose value meets one or more second criteria; activating a hypoglycemic indicator if either the one or more first criteria or the one or more second criteria are met; and providing an output based on the activated hypoglycemic indicator. In an embodiment of the first aspect, the evaluating sensor data using a first function to determine whether a real time glucose value meets one or more first criteria comprises determining whether the real-time glucose value passes a glucose threshold. In an embodiment of the first aspect, the evaluating sensor data using a first function to determine whether a real time glucose value meets one or more first criteria further comprises determining whether an amplitude of rate of change or direction of rate of change meets a rate of change criterion. In an embodiment of the first aspect, the evaluating sensor data using a first function to determine whether the real time glucose value meets one or more first criteria comprises evaluating a static risk of a substantially real time glucose value. In an embodiment of the first aspect, the evaluating sensor data using a second function to determine whether the predicted glucose value meets one or more second criteria comprises evaluating a dynamic risk of the predicted glucose value. In an embodiment of the first aspect, the second function comprises an artificial neural network model that uses at least one of exercise, stress, illness or surgery to determine the predicted glucose value. In an embodiment of the first aspect, the second function utilizes a first order autoregressive model to determine the predicted glucose value. In an embodiment of the first aspect, the first order autoregressive model comprises a parameter alpha, and wherein alpha is estimated recursively each time a sensor data points is received. In an embodiment of the first aspect, the first order autoregressive model comprises a forgetting factor, a prediction horizon and a prediction threshold tuned to provide no more than one additional alarm per week based on a retrospective analysis comparing the use of the first function and the second function together as compared to the first function alone. In an embodiment of the first aspect, evaluating the sensor data using the first function and the second function allows for increased warning time of hypoglycemic alerts without substantially increasing the number of alerts as compared to evaluating the sensor data using the first function without evaluating the sensor data using the second function. In an embodiment of the first aspect, the second function comprises a Kalman Filter to determine the predicted glucose value using as an input an estimate of the rate of change of the blood glucose. In an embodiment of the first aspect, the one or more first criteria comprises a first threshold that is configured to be user settable. In an embodiment of the first aspect, the one or more second criteria comprises a second threshold that is not user settable. In an embodiment of the first aspect, the second function comprises a prediction horizon that is not user settable. In an embodiment of the first aspect, the one or more second criteria comprises a second threshold that is adaptively set by the processor module based on the first threshold. In an embodiment of the first aspect, the second function comprises a prediction horizon that is adaptively set by the processor module based on the first threshold. In an embodiment of the first aspect, the hypoglycemic indicator comprises a flag that has a particular set of instructions associated with it depending on whether the hypoglycemic indicator was activated based on the first function meeting the one or more first criteria or whether the hypoglycemic indicator was activated based on the second function meeting the one or more second criteria. In an embodiment of the first aspect, the output comprises at least one of an audible, tactile or visual output, and wherein the output is differentiated and/or provides information selectively based on whether the hypoglycemic indicator was activated based on the first function meeting the one or more first criteria or whether the hypoglycemic indicator was activated based on the second function meeting the one or more second criteria. In an embodiment of the first aspect, providing an output comprises transmitting a message to an insulin delivery device including instructions associated with at least one of: a) suspending insulin delivery, b) initiating a hypoglycemia and/or hyperglycemia minimizer algorithm, c) controlling insulin delivery or d) information associated with the hypoglycemia indicator.

In a second aspect, a system for processing data is provided, the system comprising: a continuous analyte sensor configured to be implanted within a body; and sensor electronics configured to receive and process sensor data output by the sensor, the sensor electronics including a processor configured to: evaluate sensor data using a first function to determine whether a real time glucose value meets one or more first criteria; evaluate sensor data using a second function to determine whether a predicted glucose value meets one or more second criteria; activate a hypoglycemic indicator if either the one or more first criteria or the one or more second criteria are met; and provide an output based on the activated hypoglycemic indicator. In an embodiment of the second aspect, the evaluating sensor data using a first function to determine whether a real time glucose value meets one or more first criteria comprises determining whether the real-time glucose value passes a glucose threshold. In an embodiment of the second aspect, the evaluating sensor data using a first function to determine whether a real time glucose value meets one or more first criteria further comprises determining whether an amplitude of rate of change or direction of rate of change meets a rate of change criterion. In an embodiment of the second aspect, the evaluating sensor data using a first function to determine whether the real time glucose value meets one or more first criteria comprises evaluating a static risk of a substantially real time glucose value. In an embodiment of the second aspect, the evaluating sensor data using a second function to determine whether the predicted glucose value meets one or more second criteria comprises evaluating a dynamic risk of the predicted glucose value. In an embodiment of the second aspect, the second function comprises an artificial neural network model that uses at least one of exercise, stress, illness or surgery to determine the predicted glucose value. In an embodiment of the second aspect, the second function utilizes a first order autoregressive model to determine the predicted glucose value. In an embodiment of the second aspect, the first order autoregressive model comprises a parameter alpha, and wherein alpha is estimated recursively each time a sensor data points is received. In an embodiment of the second aspect, the first order autoregressive model comprises a forgetting factor, a prediction horizon and a prediction threshold tuned to provide no more than one additional alarm per week based on a retrospective analysis comparing the use of the first function and the second function together as compared to the first function alone. In an embodiment of the second aspect, evaluating the sensor data using the first function and the second function allows for increased warning time of hypoglycemic alerts without substantially increasing the number of alerts as compared to evaluating the sensor data using the first function without evaluating the sensor data using the second function. In an embodiment of the second aspect, the second function comprises a Kalman Filter to determine the predicted glucose value using as an input an estimate of the rate of change of the blood glucose. In an embodiment of the second aspect, the one or more first criteria comprises a first threshold that is configured to be user settable. In an embodiment of the second aspect, the one or more second criteria comprises a second threshold that is not user settable. In an embodiment of the second aspect, the second function comprises a prediction horizon that is not user settable. In an embodiment of the second aspect, the one or more second criteria comprises a second threshold that is adaptively set by the processor module based on the first threshold. In an embodiment of the second aspect, the second function comprises a prediction horizon that is adaptively set by the processor module based on the first threshold. In an embodiment of the second aspect, the hypoglycemic indicator comprises a flag that has a particular set of instructions associated with it depending on whether the hypoglycemic indicator was activated based on the first function meeting the one or more first criteria or whether the hypoglycemic indicator was activated based on the second function meeting the one or more second criteria. In an embodiment of the second aspect, the output comprises at least one of an audible, tactile or visual output, and wherein the output is differentiated and/or provides information selectively based on whether the hypoglycemic indicator was activated based on the first function meeting the one or more first criteria or whether the hypoglycemic indicator was activated based on the second function meeting the one or more second criteria. In an embodiment of the second aspect, providing output comprises transmitting a message to an insulin delivery device including instructions associated with at least one of: a) suspending insulin delivery, b) initiating a hypoglycemia and/or hyperglycemia minimizer algorithm, c) controlling insulin delivery or d) information associated with the hypoglycemia indicator.

In a third aspect, a method of transitioning between states associated with a host's glycemic condition is provided, the method comprising: evaluating sensor data from a continuous glucose sensor and activating an alert state based on the sensor data meeting one or more active transition criteria associated with a hypoglycemic condition or hyperglycemic condition; providing an output associated with the active alert state, wherein the output is indicative of the hypoglycemic condition or hyperglycemic condition; transitioning from the active state to an acknowledged state for a time period responsive to at least one of a user acknowledgment of the alert state or data indicative of the host's glucose trending toward euglycemia; actively monitoring data associated with the host's hypoglycemic or hyperglycemic condition for a time period in the acknowledged state; and transitioning from the acknowledged state to at least one of an inactive state or active state responsive to the data associated with the host's hypoglycemic or hyperglycemic condition meeting one or more predetermined criteria. In an embodiment of the third aspect, the transitioning from the active state to an acknowledged state comprises transitioning from the active state to the acknowledged state based on the data indicative of the host's glucose trending toward euglycemia, wherein the data is selected from the group consisting of a) sensor data indicative of a change in glucose trend or b) insulin information associated with a correction of the condition. In an embodiment of the third aspect, the transitioning from the active state to an acknowledged state comprises transitioning from the active state to the acknowledged state based on the a user acknowledgment, wherein the data is selected from the group consisting of a) a user acknowledgement of the alert on a user interface or b) user input insulin information or c) user input of meal information. In an embodiment of the third aspect, the actively monitoring comprises monitoring at least one of the sensor data, sensor diagnostic information, meal information, insulin information, or event information. In an embodiment of the third aspect, transitioning from the acknowledged state comprises transitioning from the acknowledged state to the inactive state based on the sensor data no longer meeting the one or more criteria associated with a hypoglycemic condition or hyperglycemic condition. In an embodiment of the third aspect, transitioning from the acknowledged state comprises transitioning from the acknowledged state to the inactive state based on the sensor data meeting one or more inactive transition criteria, wherein the inactivation criteria are different from the one or more active transition criteria associated with a hypoglycemic condition or hyperglycemic condition. In an embodiment of the third aspect, transitioning from the acknowledged state comprises transitioning from the acknowledged state to the inactive state based on insulin data and/or meal information. In an embodiment of the third aspect, transitioning from the acknowledged state comprises transitioning from the acknowledged state to the active state based on the one or more active transition criteria associated with a hypoglycemic condition or hyperglycemic condition being met and based on an expiration of a predetermined time period. In an embodiment of the third aspect, after receiving the user acknowledgement of the alert state and determining data is indicative of the host's glucose trending toward euglycemia, further comprising transitioning from the acknowledged state to the active state based on the host's glucose trending away from euglycemia during the active monitoring time period. In an embodiment of the third aspect, the method further comprises selectively outputting information associated with the state transition. In an embodiment of the third aspect, the output associated with a transition to the active state is different from the output association with a transition from the acknowledged state to the inactive state.

In a fourth aspect, a system for processing data is provided, the system comprising: a continuous analyte sensor configured to be implanted within a body; and sensor electronics configured to receive and process sensor data output by the sensor, the sensor electronics including a processor configured to: evaluate sensor data from a continuous glucose sensor and activating an alert state based on the sensor data meeting one or more active transition criteria associated with a hypoglycemic condition or hyperglycemic condition; provide an output associated with the active alert state, wherein the output is indicative of the hypoglycemic condition or hyperglycemic condition; transition from the active state to an acknowledged state for a time period responsive to at least one of a user acknowledgment of the alert state or data indicative of the host's glucose trending toward euglycemia; actively monitor data associated with the host's hypoglycemic or hyperglycemic condition for a time period in the acknowledged state; and transition from the acknowledged state to at least one of an inactive state or active state responsive to the data associated with the host's hypoglycemic or hyperglycemic condition meeting one or more predetermined criteria. In an embodiment of the fourth aspect, the transitioning from the active state to an acknowledged state comprises transitioning from the active state to the acknowledged state based on the data indicative of the host's glucose trending toward euglycemia, wherein the data is selected from the group consisting of a) sensor data indicative of a change in glucose trend or b) insulin information associated with a correction of the condition. In an embodiment of the fourth aspect, transitioning from the active state to an acknowledged state comprises transitioning from the active state to the acknowledged state based on the a user acknowledgment, wherein the data is selected from the group consisting of a) a user acknowledgement of the alert on a user interface or b) user input insulin information or c) user input of meal information. In an embodiment of the fourth aspect, the actively monitoring comprises monitoring at least one of the sensor data, sensor diagnostic information, meal information, insulin information, or event information. In an embodiment of the fourth aspect, transitioning from the acknowledged state comprises transitioning from the acknowledged state to the inactive state based on the sensor data no longer meeting the one or more criteria associated with a hypoglycemic condition or hyperglycemic condition. In an embodiment of the fourth aspect, transitioning from the acknowledged state comprises transitioning from the acknowledged state to the inactive state based on the sensor data meeting one or more inactive transition criteria, wherein the inactivation criteria are different from the one or more active transition criteria associated with a hypoglycemic condition or hyperglycemic condition. In an embodiment of the fourth aspect, transitioning from the acknowledged state comprises transitioning from the acknowledged state to the inactive state based on insulin data and/or meal information. In an embodiment of the fourth aspect, transitioning from the acknowledged state comprises transitioning from the acknowledged state to the active state based on the one or more active transition criteria associated with a hypoglycemic condition or hyperglycemic condition being met and based on an expiration of a predetermined time period. In an embodiment of the fourth aspect, after receiving the user acknowledgement of the alert state and determining data is indicative of the host's glucose trending toward euglycemia, further comprising transitioning from the acknowledged state to the active state based on the host's glucose trending away from euglycemia during the active monitoring time period. In an embodiment of the fourth aspect, the system further comprises selectively outputting information associated with the state transition. In an embodiment of the fourth aspect, the output associated with a transition to the active state is different from the output association with a transition from the acknowledged state to the inactive state.

In a fifth aspect, a method of determining when to re-alert a user based after a user has acknowledged a first alert is provided, the method comprising: initially activating an alert state based on one or more criteria based on data associated with a hypoglycemic or hyperglycemic condition being met; transitioning to an acknowledged state for an predetermined active monitoring time period responsive to at least one of a user acknowledgment or data indicative of the host's glucose trending toward euglycemia; actively monitoring, by a processor module, data associated with the host's hypoglycemic or hyperglycemic condition during the active monitoring time period; and reactivating the first alert state during the acknowledgement time period initiated by the data associated with the host's hypoglycemic or hyperglycemic condition meeting one or more second criteria. In an embodiment of the fifth aspect, the second one or more criteria are different from the first one or more criteria. In an embodiment of the fifth aspect, the method further comprises providing a first output associated with the initially activating and providing a second output associated with the reactivating. In an embodiment of the fifth aspect, the first output and the second output are different. In an embodiment of the fifth aspect, the second criteria comprise conditions indicative of the host's glucose trending toward euglycemia and further comprise conditions indicative of the host's glucose trending away from euglycemia after trending toward euglycemia during the active monitoring time period. In an embodiment of the fifth aspect, the one or more second criteria associated with reactivation comprise a change in a real-time glucose value as compared to the real-time glucose value associated with the initially activating.

In a sixth aspect, a system for processing data is provided, the system comprising: a continuous analyte sensor configured to be implanted within a body; and sensor electronics configured to receive and process sensor data output by the sensor, the sensor electronics including a processor configured to: initially activate an alert state based on one or more criteria based on data associated with a hypoglycemic or hyperglycemic condition being met; transition to an acknowledged state for an predetermined active monitoring time period responsive to at least one of a user acknowledgment or data indicative of the host's glucose trending toward euglycemia; actively monitor data associated with the host's hypoglycemic or hyperglycemic condition during the active monitoring time period; and reactivate the first alert state during the acknowledgement time period initiated by the data associated with the host's hypoglycemic or hyperglycemic condition meeting one or more second criteria. In an embodiment of the sixth aspect, the second one or more criteria are different from the first one or more criteria. In an embodiment of the sixth aspect, the system further comprises providing a first output associated with the initially activating and providing a second output associated with the reactivating. In an embodiment of the sixth aspect, the first output and the second output are different. In an embodiment of the sixth aspect, the second criteria comprise conditions indicative of the host's glucose trending toward euglycemia and further comprise conditions indicative of the host's glucose trending away from euglycemia after trending toward euglycemia during the active monitoring time period. In an embodiment of the sixth aspect, the one or more second criteria associated with reactivation comprise a change in a real-time glucose value as compared to the real-time glucose value associated with the initially activating.

In a seventh aspect, a method of avoiding unnecessary hyperglycemic alerts is provided, the method comprising: initially activating a first alert state based on one or more first criteria associated with a hyperglycemic condition; waiting a time period before providing an output associated with the first alert state; actively monitoring, by a processor module, data associated with the host's hyperglycemic condition during the waiting time period; and providing an output associated with the first alert state after the waiting time period based on the data associated with the host's hyperglycemic condition meeting one or more second criteria. In an embodiment of the seventh aspect, the actively monitoring comprises determining an average glucose over a window of time. In an embodiment of the seventh aspect, the actively monitoring comprises determining an amplitude and/or direction of rate of change. In an embodiment of the seventh aspect, the actively monitoring comprises determining an amplitude and/or direction of rate of acceleration. In an embodiment of the seventh aspect, the actively monitoring comprises evaluating insulin information. In an embodiment of the seventh aspect, the actively monitoring comprises evaluating meal information or timing. In an embodiment of the seventh aspect, the waiting time period is user selectable. In an embodiment of the seventh aspect, the method further comprises not providing output associated with the first alert state after the waiting time period based on the data associated with the host's hyperglycemic condition not meeting the one or more second criteria. In an embodiment of the seventh aspect, the one or more first criteria and the one or more second criteria are the same. In an embodiment of the seventh aspect, the one or more first criteria and the one or more second criteria are different. In an embodiment of the seventh aspect, the method further comprises transitioning from the first alert state to an inactive alert state based on the data associated with the host's hyperglycemic condition meeting one or more third criteria. In an embodiment of the seventh aspect, the one or more first criteria and the one or more third criteria are the same. In an embodiment of the seventh aspect, the one or more first criteria and the one or more third criteria are different.

In an eighth aspect, a system for processing data is provided, the system comprising: a continuous analyte sensor configured to be implanted within a body; and sensor electronics configured to receive and process sensor data output by the sensor, the sensor electronics including a processor configured to: initially activate a first alert state based on one or more first criteria associated with a hyperglycemic condition; wait a time period before providing an output associated with the first alert state; actively monitor data associated with the host's hyperglycemic condition during the waiting time period; and provide an output associated with the first alert state after the waiting time period based on the data associated with the host's hyperglycemic condition meeting one or more second criteria. In an embodiment of the eighth aspect, the actively monitoring comprises determining an average glucose over a window of time. In an embodiment of the eighth aspect, the actively monitoring comprises determining an amplitude and/or direction of rate of change. In an embodiment of the eighth aspect, the actively monitoring comprises determining an amplitude and/or direction of rate of acceleration. In an embodiment of the eighth aspect, the actively monitoring comprises evaluating insulin information. In an embodiment of the eighth aspect, the actively monitoring comprises evaluating meal information or timing. In an embodiment of the eighth aspect, the waiting time period is user selectable. In an embodiment of the eighth aspect, the system further comprises not providing output associated with the first alert state after the waiting time period based on the data associated with the host's hyperglycemic condition not meeting the one or more second criteria. In an embodiment of the eighth aspect, the one or more first criteria and the one or more second criteria are the same. In an embodiment of the eighth aspect, the one or more first criteria and the one or more second criteria are different. In an embodiment of the eighth aspect, the system further comprises transitioning from the first alert state to an inactive alert state based on the data associated with the host's hyperglycemic condition meeting one or more third criteria. In an embodiment of the eighth aspect, the one or more first criteria and the one or more third criteria are the same. In an embodiment of the eighth aspect, the one or more first criteria and the one or more third criteria are different.

BRIEF DESCRIPTION OF THE DRAWINGS

The details of the present disclosure, both as to its structure and operation, may be understood in part by study of the accompanying drawings, in which like reference numerals refer to like parts. The drawings are not necessarily to scale, emphasis instead being placed upon illustrating the principles of the disclosure.

DETAILED DESCRIPTION

Figure 1:
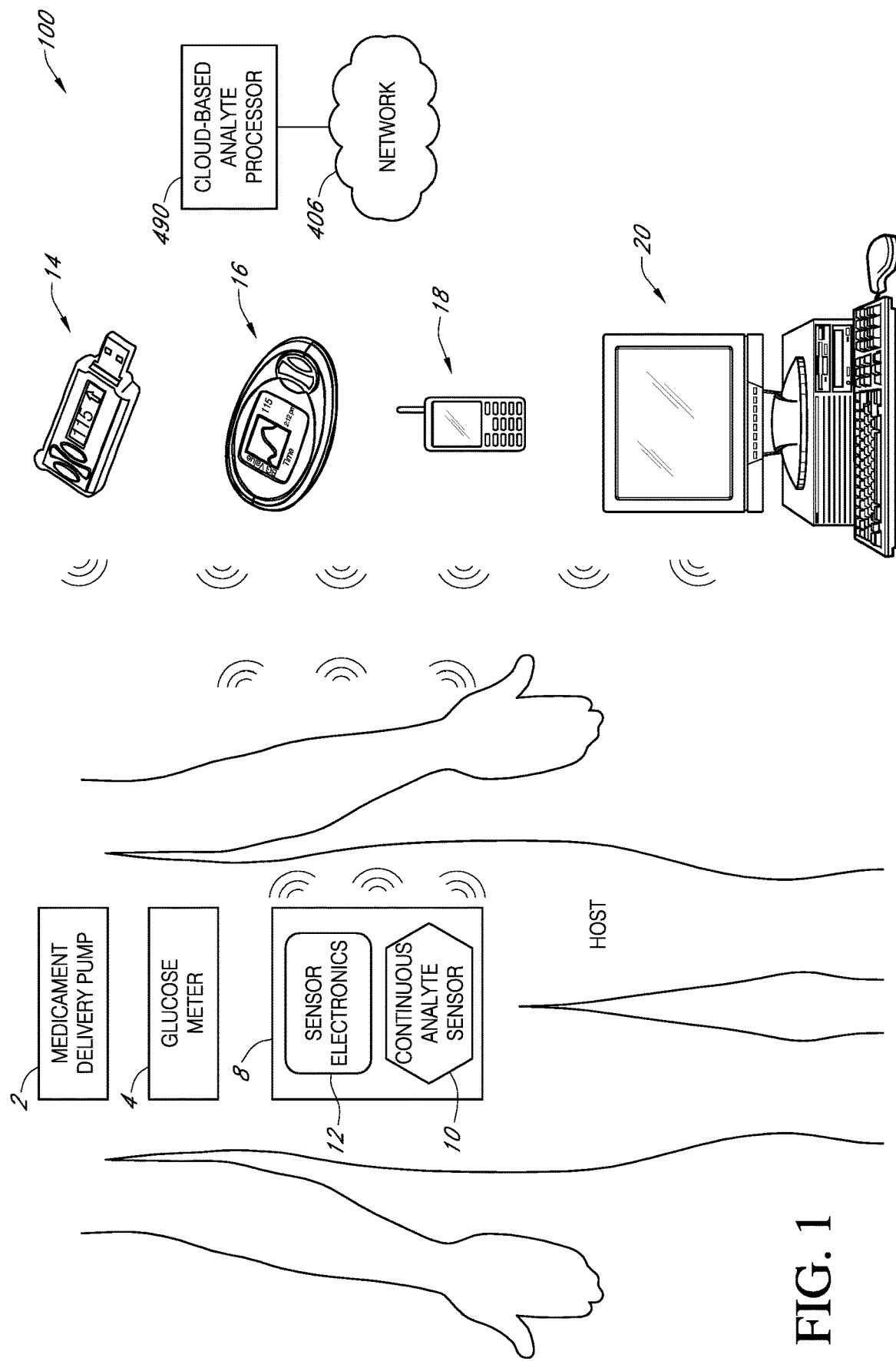
FIG. 1 is a schematic view of a continuous analyte sensor system attached to a host and communicating with a plurality of example devices.

The following detailed description describes the present embodiments with reference to the drawings. In the drawings, reference numbers label elements of the present embodiments. These reference numbers are reproduced below in connection with the discussion of the corresponding drawing features.

Sensor System and Applicator

FIG. 1 depicts an example system 100, in accordance with some example implementations. The system 100 includes a continuous analyte sensor system 8 including sensor electronics 12 and a continuous analyte sensor 10. The system 100 may include other devices and/or sensors, such as medicament delivery pump 2 and glucose meter 4. The continuous analyte sensor 10 may be physically connected to sensor electronics 12 and may be integral with (e.g., non-releasably attached to) or releasably attachable to the continuous analyte sensor 10. The sensor electronics 12, medicament delivery pump 2, and/or glucose meter 4 may couple with one or more devices, such as display devices 14, 16, 18, and/or 20.

In some example implementations, the system 100 may include a cloud-based analyte processor 490 configured to analyze analyte data (and/or other patient related data) provided via network 406 (e.g., via wired, wireless, or a combination thereof) from sensor system 8 and other devices, such as display devices 14-20 and the like, associated with the host (also referred to as a patient) and generate reports providing high-level information, such as statistics, regarding the measured analyte over a certain time frame. A full discussion of using a cloud-based analyte processing system may be found in U.S. Patent Application No. 61/655,991, entitled "Cloud-Based Processing of Analyte Data" and filed on Jun. 5, 2012, herein incorporated by reference in its entirety.

In some example implementations, the sensor electronics 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics 12 may include hardware, firmware, software, or a combination thereof to provide measurement of levels of the analyte via a continuous analyte sensor, such as a continuous glucose sensor. An example implementation of the sensor electronics 12 is described further below with respect to FIG. 2.

The term "sensor data", as used herein is a broad term and is to be given its ordinary and customary meaning to a person of ordinary skill in the art (and is not to be limited to a special or customized meaning), and furthermore refers without limitation to any data associated with a sensor, such as a continuous analyte sensor. Sensor data includes a raw data stream, or simply a data stream, of analog or digital signal related to a measured analyte from an analyte sensor (or other signal received from another sensor), as well as calibrated and/or filtered raw data. In one example, the sensor data comprises digital data in "counts" converted by an A/D converter from an analog signal (e.g., voltage or amps) and includes one or more data points representative of a glucose concentration. Thus, the terms "sensor data point" and "data point" refer generally to a digital representation of sensor data at a particular time. The term broadly encompasses a plurality of time spaced data points from a sensor, such as from a substantially continuous glucose sensor, which includes individual measurements taken at time intervals ranging from fractions of a second up to, e.g., 1, 2, or 5 minutes or longer. In another example, the sensor data includes an integrated digital value representative of one or more data points averaged over a time period. In some embodiments, sensor data may include calibrated data, smoothed data, filtered data, transformed data, and/or any other data associated with a sensor.

The sensor electronics 12 may, as noted, couple (e.g., wirelessly and the like) with one or more devices, such as display devices 14, 16, 18, and/or 20. The display devices 14, 16, 18, and/or 20 may be configured for presenting information (and/or alarming), such as sensor information transmitted by the sensor electronics 12 for display at the display devices 14, 16, 18, and/or 20.

The display devices may include a relatively small, key fob-like display device 14, a relatively large, hand-held display device 16, a cellular phone 18 (e.g., a smart phone, a tablet, and the like), a computer 20, and/or any other user equipment configured to at least present information (e.g., medicament delivery information, discrete self-monitoring glucose readings, heart rate monitor, caloric intake monitor, and the like).

In some example implementations, the relatively small, key fob-like display device 14 may comprise a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the large display device 16) and may be configured to display certain types of displayable sensor information, such as a numerical value and an arrow.

In some example implementations, the relatively large, hand-held display device 16 may comprise a hand-held receiver device, a palm-top computer, and/or the like. This large display device may include a relatively larger display (e.g., larger than the small display device 14) and may be configured to display information, such as a graphical representation of the continuous sensor data including current and historic sensor data output by sensor system 8.

In some example implementations, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some example implementations, the continuous analyte sensor 10 may analyze a plurality of intermittent blood samples, although other analytes may be used as well.

In some example implementations, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescence monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

Although the disclosure herein refers to some implementations that include a continuous analyte sensor 10 comprising a glucose sensor, the continuous analyte sensor 10 may comprises other types of analyte sensors as well. Moreover, although some implementations refer to the glucose sensor as an implantable glucose sensor, other types of devices capable of detecting a concentration of glucose and providing an output signal representative of glucose concentration may be used as well. Furthermore, although the description herein refers to glucose as the analyte being measured, processed, and the like, other analytes may be used as well including, for example, ketone bodies (e.g., acetone, acetoacetic acid and beta hydroxybutyric acid, lactate, etc.), glucagon, Acetyl Co A, triglycerides, fatty acids, intermediaries in the citric acid cycle, choline, insulin, cortisol, testosterone, and the like.

Figure 2:
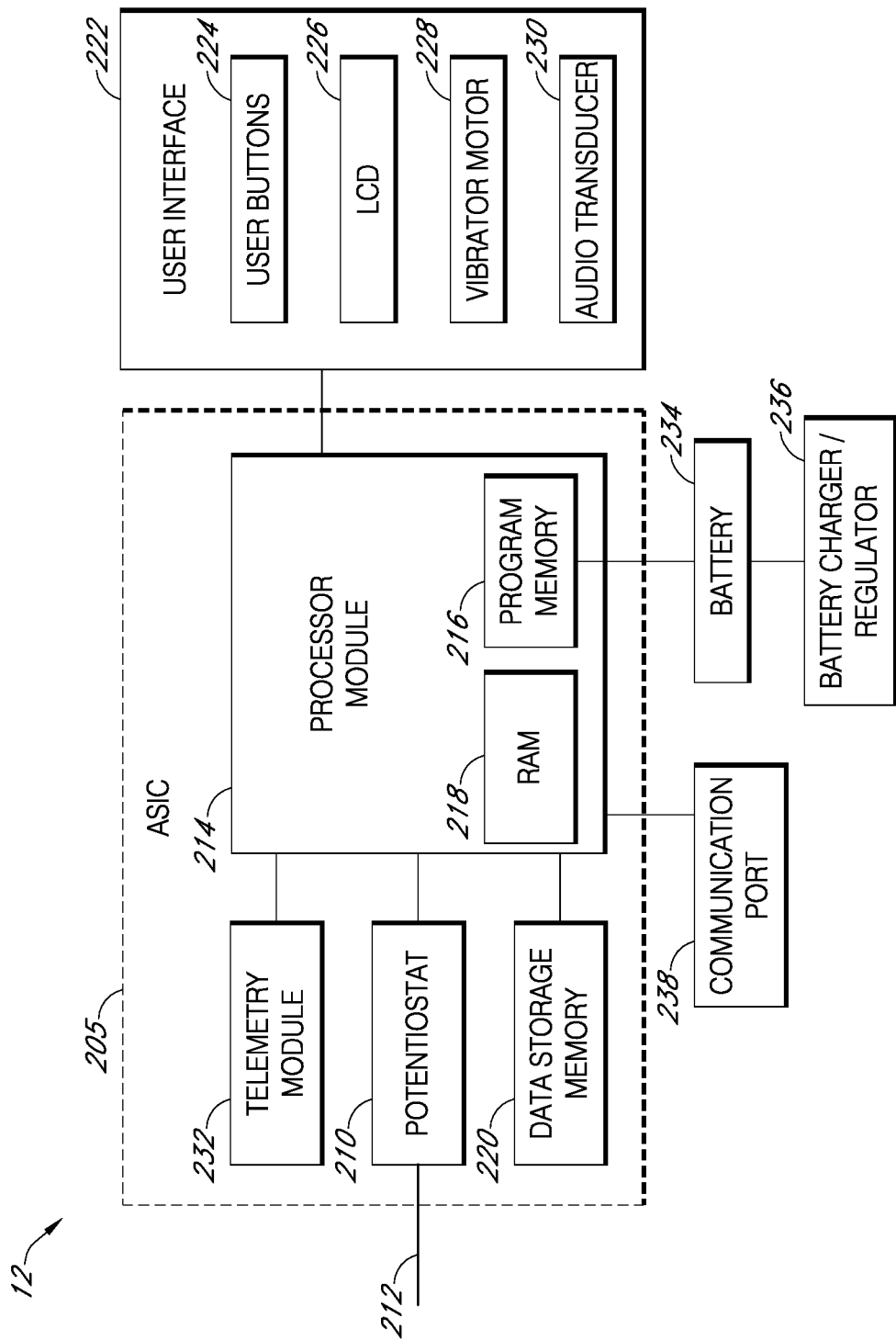
FIG. 2 is a block diagram that illustrates electronics associated with the sensor system of FIG. 1.
Figure 3A:
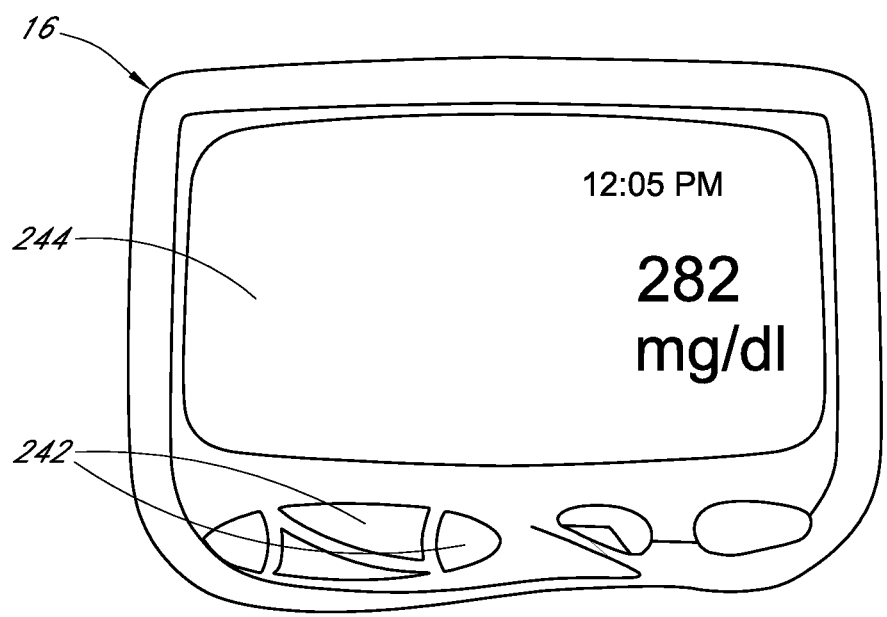
FIG. 3A illustrates an embodiment, where the receiver of FIG. 1 shows a numeric representation of the estimated analyte value on its user interface.
Figure 3B:
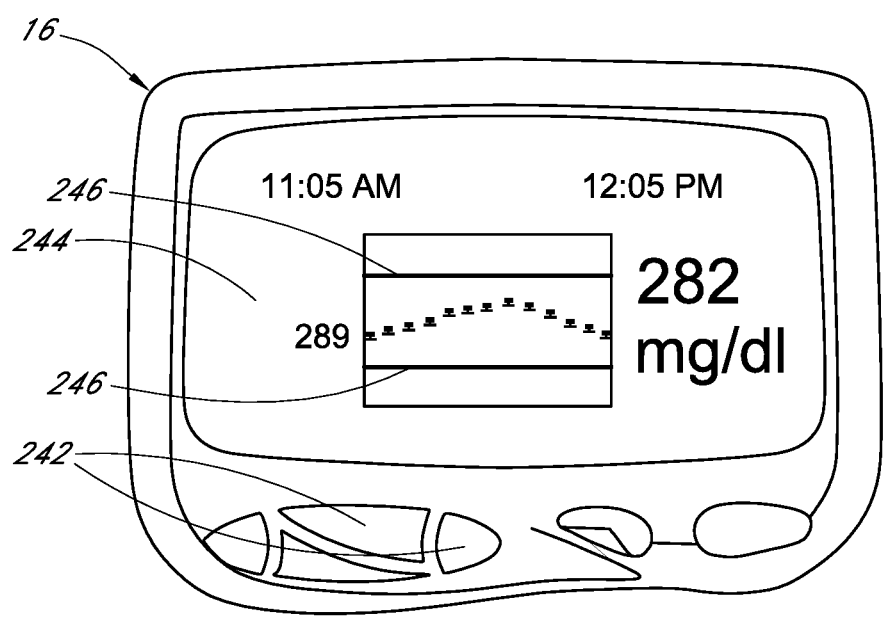
FIG. 3B illustrates an embodiment, where the receiver of FIG. 1 shows an estimated glucose value and one hour of historical data trend on its user interface.
Figure 3C:
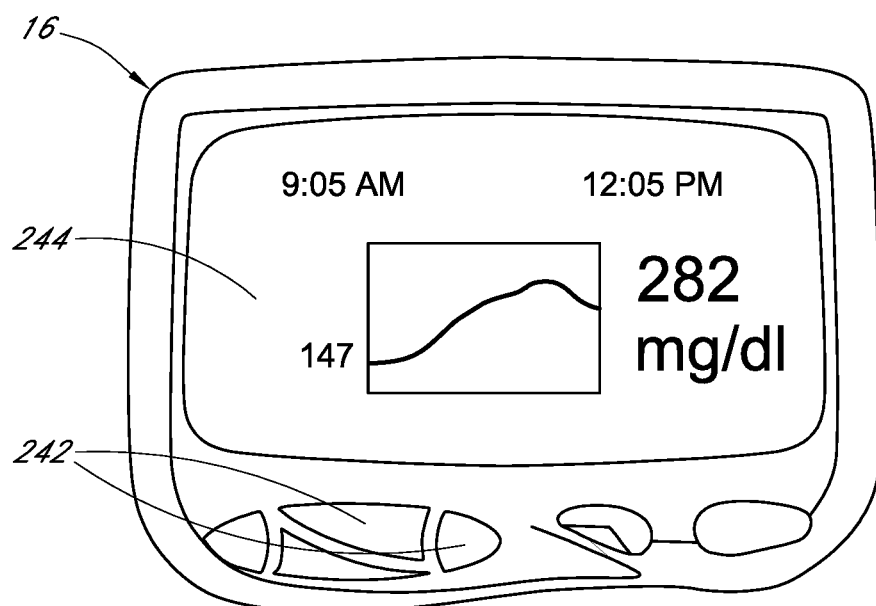
FIG. 3C illustrates an embodiment, where the receiver of FIG. 1 shows an estimated glucose value and three hours of historical trend data on its user interface.
Figure 3D:
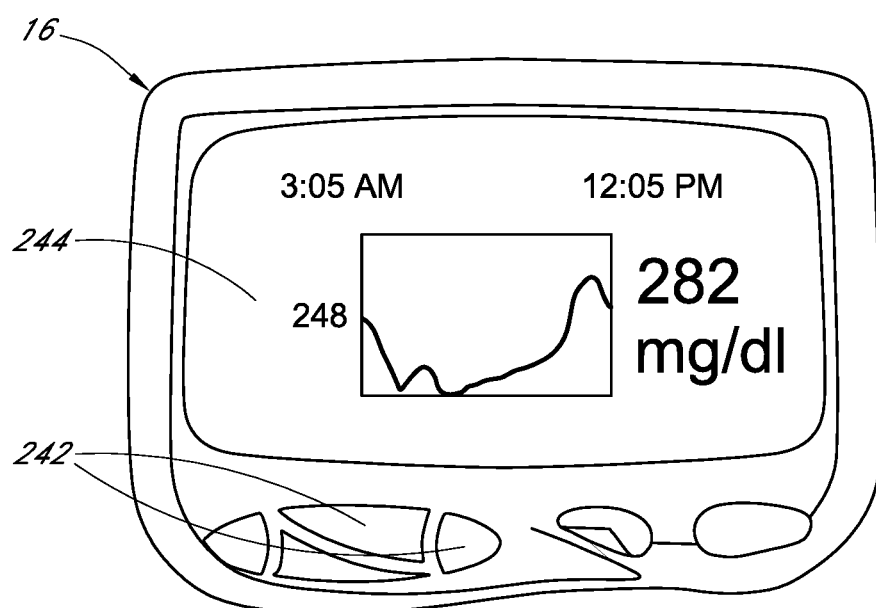
FIG. 3D illustrates an embodiment, where the receiver of FIG. 1 shows and estimated glucose value and nine hours of historical trend data on its user interface.

FIG. 2 depicts an example of sensor electronics 12, in accordance with some example implementations. The sensor electronics 12 may include sensor electronics that are configured to process sensor information, such as sensor data, and generate transformed sensor data and displayable sensor information, e.g., via a processor module. For example, the processor module may transform sensor data into one or more of the following: filtered sensor data (e.g., one or more filtered analyte concentration values), raw sensor data, calibrated sensor data (e.g., one or more calibrated analyte concentration values), rate of change information, trend information, rate of acceleration/deceleration information, sensor diagnostic information, location information, alarm/alert information, calibration information, smoothing and/or filtering algorithms of sensor data, and/or the like.

In some embodiments, a processor module 214 is configured to achieve a substantial portion, if not all, of the data processing. Processor module 214 may be integral to sensor electronics 12 and/or may be located remotely, such as in one or more of devices 14, 16, 18, and/or 20 and/or cloud 490. In some embodiments, processor module 214 may comprise a plurality of smaller subcomponents or submodules. For example, processor module 214 may include an alert module (not shown) or prediction module (not shown), or any other suitable module that may be utilized to efficiently process data. When processor module 214 is made up of a plurality of submodules, the submodules may be located within processor module 214, including within the sensor electronic 12 or other associated devices (e.g., 14, 16, 18, 20 and/or 490). For example, in some embodiments, processor module 214 may be located at least partially within cloud-based analyte processor 490 or elsewhere in network 406.

In some example implementations, the processor module 214 may be configured to calibrate the sensor data, and the data storage memory 220 may store the calibrated sensor data points as transformed sensor data. Moreover, the processor module 214 may be configured, in some example implementations, to wirelessly receive calibration information from a display device, such as devices 14, 16, 18, and/or 20, to enable calibration of the sensor data from sensor 12. Furthermore, the processor module 214 may be configured to perform additional algorithmic processing on the sensor data (e.g., calibrated and/or filtered data and/or other sensor information), and the data storage memory 220 may be configured to store the transformed sensor data and/or sensor diagnostic information associated with the algorithms.

In some example implementations, the sensor electronics 12 may comprise an application-specific integrated circuit (ASIC) 205 coupled to a user interface 222. The ASIC 205 may further include a potentiostat 210, a telemetry module 232 for transmitting data from the sensor electronics 12 to one or more devices, such devices 14, 16, 18, and/or 20, and/or other components for signal processing and data storage (e.g., processor module 214 and data storage memory 220). Although FIG. 2 depicts ASIC 205, other types of circuitry may be used as well, including field programmable gate arrays (FPGA), one or more microprocessors configured to provide some (if not all of) the processing performed by the sensor electronics 12, analog circuitry, digital circuitry, or a combination thereof.

In the example depicted at FIG. 2, the potentiostat 210 is coupled to a continuous analyte sensor 10, such as a glucose sensor to generate sensor data from the analyte. The potentiostat 210 may also provide via data line 212 a voltage to the continuous analyte sensor 10 to bias the sensor for measurement of a value (e.g., a current and the like) indicative of the analyte concentration in a host (also referred to as the analog portion of the sensor). The potentiostat 210 may have one or more channels depending on the number of working electrodes at the continuous analyte sensor 10.

In some example implementations, the potentiostat 210 may include a resistor that translates a current value from the sensor 10 into a voltage value, while in some example implementations, a current-to-frequency converter (not shown) may also be configured to integrate continuously a measured current value from the sensor 10 using, for example, a charge-counting device. In some example implementations, an analog-to-digital converter (not shown) may digitize the analog signal from the sensor 10 into so-called "counts" to allow processing by the processor module 214. The resulting counts may be directly related to the current measured by the potentiostat 210, which may be directly related to an analyte level, such as a glucose level, in the host.

The telemetry module 232 may be operably connected to processor module 214 and may provide the hardware, firmware, and/or software that enable wireless communication between the sensor electronics 12 and one or more other devices, such as display devices, processors, network access devices, and the like. A variety of wireless radio technologies that can be implemented in the telemetry module 232 include Bluetooth, Bluetooth Low-Energy, ANT, ANT+, ZigBee, IEEE 802.11, IEEE 802.16, cellular radio access technologies, radio frequency (RF), infrared (IR), paging network communication, magnetic induction, satellite data communication, spread spectrum communication, frequency hopping communication, near field communications, and/or the like. In some example implementations, the telemetry module 232 comprises a Bluetooth chip, although the Bluetooth technology may also be implemented in a combination of the telemetry module 232 and the processor module 214.

The processor module 214 may control the processing performed by the sensor electronics 12. For example, the processor module 214 may be configured to process data (e.g., counts), from the sensor, filter the data, calibrate the data, perform fail-safe checking, and/or the like.

In some example implementations, the processor module 214 may comprise a digital filter, such as for example an infinite impulse response (IIR) or a finite impulse response (FIR) filter. This digital filter may smooth a raw data stream received from sensor 10. Generally, digital filters are programmed to filter data sampled at a predetermined time interval (also referred to as a sample rate). In some example implementations, such as when the potentiostat 210 is configured to measure the analyte (e.g., glucose and/or the like) at discrete time intervals, these time intervals determine the sampling rate of the digital filter. In some example implementations, the potentiostat 210 may be configured to measure continuously the analyte, for example, using a current-to-frequency converter. In these current-to-frequency converter implementations, the processor module 214 may be programmed to request, at predetermined time intervals (acquisition time), digital values from the integrator of the current-to-frequency converter. These digital values obtained by the processor module 214 from the integrator may be averaged over the acquisition time due to the continuity of the current measurement. As such, the acquisition time may be determined by the sampling rate of the digital filter.

The processor module 214 may further include a data generator (not shown) configured to generate data packages for transmission to devices, such as the display devices 14, 16, 18, and/or 20. Furthermore, the processor module 214 may generate data packets for transmission to these outside sources via telemetry module 232. In some example implementations, the data packages may, as noted, be customizable for each display device, and/or may include any available data, such as a time stamp, displayable sensor information, transformed sensor data, an identifier code for the sensor and/or sensor electronics 12, raw data, filtered data, calibrated data, rate of change information, trend information, error detection or correction, and/or the like.

The processor module 214 may also include a program memory 216 and other memory 218. The processor module 214 may be coupled to a communications interface, such as a communication port 238, and a source of power, such as a battery 234. Moreover, the battery 234 may be further coupled to a battery charger and/or regulator 236 to provide power to sensor electronics 12 and/or charge the battery 234.

The program memory 216 may be implemented as a semi-static memory for storing data, such as an identifier for a coupled sensor 10 (e.g., a sensor identifier (ID)) and for storing code (also referred to as program code) to configure the ASIC 205 to perform one or more of the operations/functions described herein. For example, the program code may configure processor module 214 to process data streams or counts, filter, calibrate, perform fail-safe checking, and the like.

The memory 218 may also be used to store information. For example, the processor module 214 including memory 218 may be used as the system's cache memory, where temporary storage is provided for recent sensor data received from the sensor. In some example implementations, the memory may comprise memory storage components, such as read-only memory (ROM), random-access memory (RAM), dynamic-RAM, static-RAM, non-static RAM, easily erasable programmable read only memory (EEPROM), rewritable ROMs, flash memory, and the like.

The data storage memory 220 may be coupled to the processor module 214 and may be configured to store a variety of sensor information. In some example implementations, the data storage memory 220 stores one or more days of continuous analyte sensor data. For example, the data storage memory may store 1, 2, 3, 4, 5, 6, 7, 8, 9, 10, 11, 12, 13, 14, 15, 20, and/or 30 (or more days) of continuous analyte sensor data received from sensor 10. The stored sensor information may include one or more of the following: a time stamp, raw sensor data (one or more raw analyte concentration values), calibrated data, filtered data, transformed sensor data, and/or any other displayable sensor information, calibration information (e.g., reference BG values and/or prior calibration information), sensor diagnostic information, and the like.

The user interface 222 may include a variety of interfaces, such as one or more buttons 224, a liquid crystal display (LCD) 226, a vibrator 228, an audio transducer (e.g., speaker) 230, a backlight (not shown), and/or the like. The components that comprise the user interface 222 may provide controls to interact with the user (e.g., the host). One or more buttons 224 may allow, for example, toggle, menu selection, option selection, status selection, yes/no response to on-screen questions, a "turn off" function (e.g., for an alarm), an "acknowledged" function (e.g., for an alarm), a reset, and/or the like. The LCD 226 may provide the user with, for example, visual data output. The audio transducer 230 (e.g., speaker) may provide audible signals in response to triggering of certain alerts, such as present and/or predicted hyperglycemic and hypoglycemic conditions. In some example implementations, audible signals may be differentiated by tone, volume, duty cycle, pattern, duration, and/or the like. In some example implementations, the audible signal may be configured to be silenced (e.g., acknowledged or turned off) by pressing one or more buttons 224 on the sensor electronics 12 and/or by signaling the sensor electronics 12 using a button or selection on a display device (e.g., key fob, cell phone, and/or the like).

Although audio and vibratory alarms are described with respect to FIG. 2, other alarming mechanisms may be used as well. For example, in some example implementations, a tactile alarm is provided including a poking mechanism configured to "poke" or physically contact the patient in response to one or more alarm conditions.

The battery 234 may be operatively connected to the processor module 214 (and possibly other components of the sensor electronics 12) and provide the necessary power for the sensor electronics 12. In some example implementations, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some example implementations, the battery is rechargeable. In some example implementations, a plurality of batteries can be used to power the system. In yet other implementations, the receiver can be transcutaneously powered via an inductive coupling, for example.

A battery charger and/or regulator 236 may be configured to receive energy from an internal and/or external charger. In some example implementations, a battery regulator (or balancer) 236 regulates the recharging process by bleeding off excess charge current to allow all cells or batteries in the sensor electronics 12 to be fully charged without overcharging other cells or batteries. In some example implementations, the battery 234 (or batteries) is configured to be charged via an inductive and/or wireless charging pad, although any other charging and/or power mechanism may be used as well.

One or more communication ports 238, also referred to as external connector(s), may be provided to allow communication with other devices, for example a PC communication (com) port can be provided to enable communication with systems that are separate from, or integral with, the sensor electronics 12. The communication port, for example, may comprise a serial (e.g., universal serial bus or "USB") communication port, and allow for communicating with another computer system (e.g., PC, personal digital assistant or "PDA," server, or the like). In some example implementations, the sensor electronics 12 is able to transmit historical data to a PC or other computing device (e.g., an analyte processor as disclosed herein) for retrospective analysis by a patient and/or physician.

In some continuous analyte sensor systems, an on-skin portion of the sensor electronics may be simplified to minimize complexity and/or size of on-skin electronics, for example, providing only raw, calibrated, and/or filtered data to a display device configured to run calibration and other algorithms required for displaying the sensor data. However, the sensor electronics 12 (e.g., via processor module 214) may be implemented to execute prospective algorithms used to generate transformed sensor data and/or displayable sensor information, including, for example, algorithms that: evaluate a clinical acceptability of reference and/or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor and/or sensor data, detect signal artifacts (noise), replace signal artifacts, determine a rate of change and/or trend of the sensor data, perform dynamic and intelligent analyte value estimation, perform diagnostics on the sensor and/or sensor data, set modes of operation, evaluate the data for aberrancies, and/or the like.

Although separate data storage and program memories are shown in FIG. 2, a variety of configurations may be used as well. For example, one or more memories may be used to provide storage space to support data processing and storage requirements at sensor electronics 12.

Referring now to FIGS. 3A to 3D, more detailed schematic views of hand-held receiver 16 is shown. Hand-held receiver 16 may comprise systems necessary to receive, process, and display sensor data from an analyte sensor, such as described elsewhere herein. Particularly, the hand-held receiver 16 can be a pager-sized device, for example, and comprise a user interface that has a plurality of buttons 242 and a liquid crystal display (LCD) screen 244, and which can include a backlight. In some embodiments, the user interface can also include a keyboard, a speaker, and a vibrator.

In some embodiments, a user is able to toggle through some or all of the screens shown in FIGS. 3A to 3D using a toggle button on the hand-held receiver. In some embodiments, the user is able to interactively select the type of output displayed on their user interface. In some embodiments, the sensor output can have alternative configurations.

In some embodiments, analyte values are displayed on e.g., a display of medical device received. In some embodiments, prompts or messages can be displayed on the display device to convey information to the user, such as reference outlier values, requests for reference analyte values, therapy recommendations, deviation of the measured analyte values from the estimated analyte values, providing predictive alert/alarm, monitoring the glycemic alert state after the alert/alarm is triggered, determining state changes, or the like. Additionally, prompts can be displayed to guide the user through calibration or troubleshooting of the calibration.

Figure 4A:
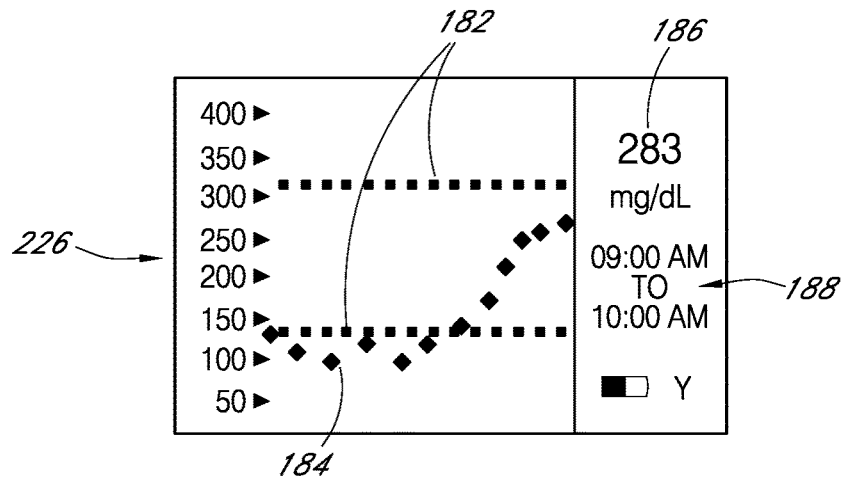
FIGS. 4A, 4B and 4C are illustrations of receiver liquid crystal displays showing embodiments of screen displays.
Figure 4B:
Figure 4C:
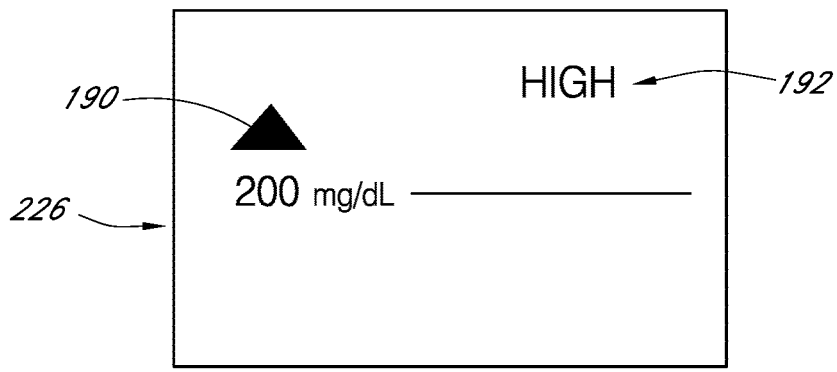

FIGS. 4A to 4C illustrate some additional visual displays that can be provided on the user interface 222. While these visual displays may include the same or similar output to the ones shown on hand-held device 16 in FIG. 3, and the visual displays of FIG. 4 can be provided on any suitable user interface 222, such as those on devices 14, 16, 18, 20. In some embodiments, the LCD 226 is a touch-activated screen, enabling each selection by a user, for example, from a menu on the screen. Buttons can provide for toggle, menu selection, option selection, mode selection, and reset, for example. In some alternative embodiments, a microphone can be provided to allow for voice-activated control.

FIG. 4A is an illustration of an LCD screen 226 showing continuous and single point glucose information in the form of a trend graph 184 and a single numerical value 186. The trend graph shows upper and lower boundaries 182 representing a target range between which the host should maintain his/her glucose values. Preferably, the receiver is configured such that these boundaries 182 can be configured or customized by a user, such as the host or a care provider. By providing visual boundaries 182, in combination with continuous analyte values over time (e.g., a trend graph 184), a user can better learn how to control his/her analyte concentration (e.g., a person with diabetes can better learn how to control his/her glucose concentration) as compared to single point (e.g., single numerical value 186) alone. Although FIG. 4A illustrates a 1-hour trend graph (e.g., depicted with a time range 188 of 1-hour), a variety of time ranges can be represented on the screen 226, for example, 3-hour, 9-hour, 1-day, and the like.

FIG. 4B is an illustration of an LCD screen 226 showing a low alert screen that can be displayed responsive to a host's analyte concentration falling below a lower boundary (see boundaries 182). In this example screen, a host's glucose concentration has fallen to 55 mg/dL, which is below the lower boundary set in FIG. 4A, for example. The arrow 190 represents the direction of the analyte trend, for example, indicating that the glucose concentration is continuing to drop. The annotation 192 ("LOW") is helpful in immediately and clearly alerting the host that his/her glucose concentration has dropped below a preset limit, and what may be considered to be a clinically safe value, for example.

In contrast, FIG. 4C is an illustration of an LCD screen 226 showing a high alert screen that can be displayed responsive to a host's analyte concentration rising above an upper boundary (see boundaries 182). In this example screen, a host's glucose concentration has risen to 200 mg/dL, which is above a boundary set by the host, thereby triggering the high alert screen. The arrow 190 represents the direction of the analyte trend, for example, indicating that the glucose concentration is continuing to rise. The annotation 192 ("HIGH") is helpful in immediately and clearly alerting the host that his/her glucose concentration has above a preset limit, and what may be considered to be a clinically safe value, for example.

Although a few example screens are depicted herein, a variety of screens can be provided for illustrating any of the information described in the provided embodiments, as well as additional information. A user can toggle between these screens and/or the screens can be automatically displayed responsive to programming within the e.g., hand-held receiver 16, and can be simultaneously accompanied by another type of alert (e.g., audible or tactile).

Figure 4D:
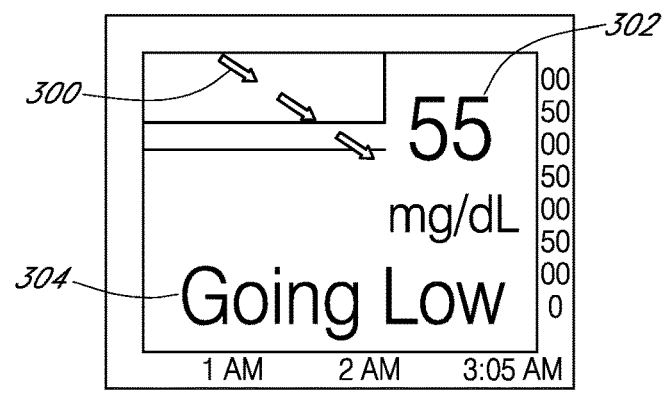
FIG. 4D is a screenshot of a smartphone display illustrating one embodiment of an alert indicting that the user's blood glucose is dropping and will soon be in a low range.
Figure 4E:
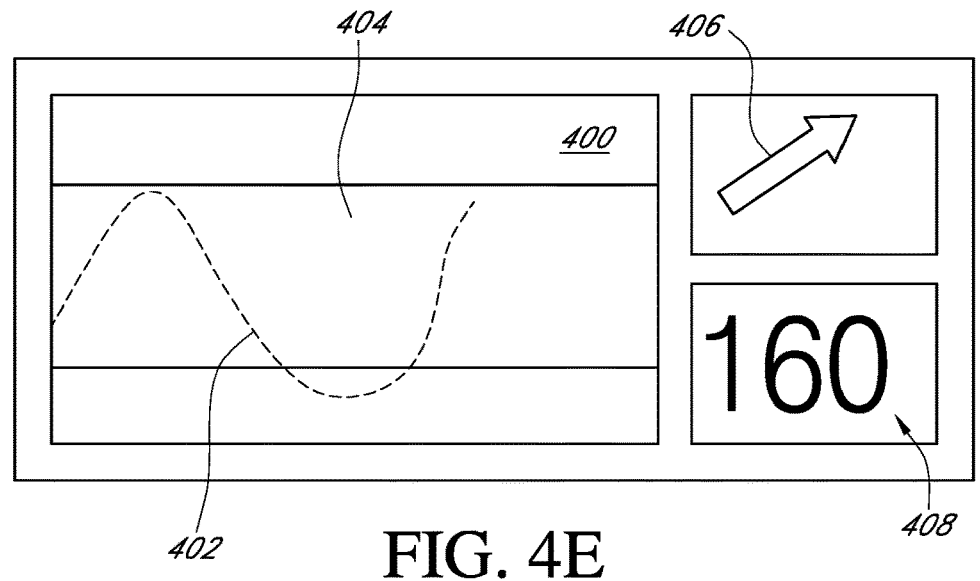
FIG. 4E is a screenshot of a smartphone display illustrating one embodiment of a blood glucose trend graph.
Figure 4F:
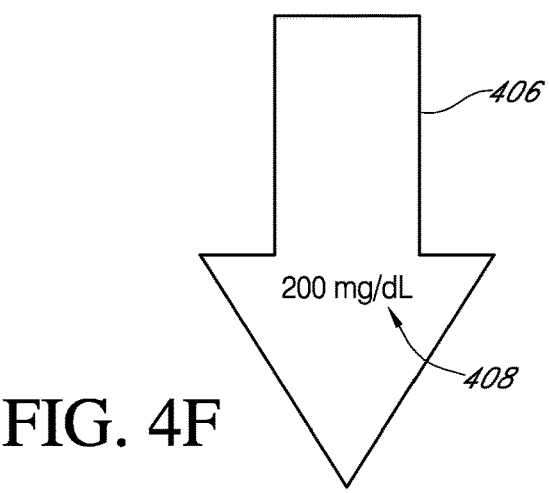
FIG. 4F is an embodiment of a blood glucose trend arrow.

For example, FIG. 4D is a screenshot of a smartphone 18 display illustrating one embodiment of an alert indicting that the user's blood glucose is dropping and will soon be in a low range. FIG. 4E is a screenshot of a smartphone 18 display illustrating one embodiment of a blood glucose trend graph. FIG. 4F is an embodiment of a blood glucose trend arrow.

In some embodiments, the processor module 214 may provide a predictive alert on a smartphone 18 display or user interface 222 when a severe hypoglycemic event is predicted to occur in the near future. For example, the predictive alert may be shown when a severe hypoglycemic event is predicted to occur within 5 minutes, 10 minutes, 15 minutes, 20 minutes, 30 minutes, etc. With reference to FIG. 4D, an arrow 300 may be displayed on a trend screen pointing towards a BG value 302 that indicates a severe hypoglycemic event, such as 55 mg/dL. The arrow 300 may change color as it transitions from euglycemia to hypoglycemia, to emphasize the change in glucose levels that is expected. Furthermore, the arrow 300 may be animated to flash to emphasize the seriousness of the alert. The display may also show text 304, such as Going LOW. This predictive alert may be configured to be prioritized over (override) whatever mode or application the smartphone 18 is in at the time the processor module 214 determines that a severe hypoglycemic event is predicted to occur. In other words, the alert may interrupt whatever is currently on the smartphone's user interface 222.

In these embodiments, the processor module 214 may be programmed with a blood glucose value corresponding to a threshold below which the user is considered to be hypoglycemic. As the processor module 214 receives as inputs multiple EGV's at time-spaced intervals, it processes the inputs by comparing each one to the programmed value, and also to previously received EGV's. If the user's blood glucose shows a downward trend, and is approaching the programmed value, the processor module 214 outputs an alert such as the one shown in FIG. 4D to the smartphone's user interface 222. The user thus receives an advance warning of a potential hypoglycemic event, so that he or she can take appropriate action to avoid the hypoglycemic event.

In various other embodiments, the processor module 214 may change the color of the user interface 222 to reflect the user's current blood glucose level. For example, the user's EGV may be displayed on the screen as a number, as a trend graph, a horizontal bar graph, etc. The text and/or background on the user interface 222 may change when the user's current blood glucose level transitions from one state to another. For example, the text/background may show a first color, such as green, if the user's blood glucose is within a healthy range, and a second color, such as red, if the user's blood glucose is low or high. Alternatively, a first color may be used for the healthy range, a second color for low, and a third color for high. Further, when in the low or high range, as the user's blood glucose becomes increasingly lower or higher, the intensity of the color may increase. The text/background may also flash, with the frequency of the flashing increasing as the user's blood glucose becomes increasingly lower or higher.

In these embodiments, the processor module 214 may be programmed with blood glucose values corresponding to low and high threshold BG values. As the processor module 214 receives as inputs multiple EGV's at time-spaced intervals, it processes the inputs by comparing each one to the programmed values. If the user's blood glucose value crosses one of the thresholds, the processor module 214 outputs an alert to the smartphone's user interface 222 in the form of changing the color of the text and/or background. If the user's blood glucose value continues to become increasingly low or high, the processor module 214 produces additional outputs, such as increasing the intensity of the color and/or causing the text/background to flash. These additional outputs may be generated in response to the processor module 214 comparing input EGV's to additional programmed threshold values.

In various other embodiments, the processor module 214 may use iconography and/or alert symbols that reflect real time data. For example, the user's blood glucose becomes low, an icon on the smartphone 18 may show an image of the user's BG trend graph using e.g., actual data points from EGV's. The input-processing-output for this embodiment would be substantially the same as that for the previous embodiment.

With extremely low blood glucose, a person can lose consciousness. Thus, in certain of the present embodiments, at a predetermined level or event (low glucose level, no button pressing after alert, etc.) that might signify a loss of consciousness, the processor module 214 may go into an emergency response instruction mode. This mode may include an alarm to alert others in close proximity to the user that something is wrong. For example, step-by-step instructions on how to assist the unconscious user may be shown on the smartphone's user interface 222, such as administering glucose tabs or another form of carbohydrates, calling an ambulance, etc.

In these embodiments, the processor module 214 may receive an input from a CGM, which is the user's EGV. The processor module 214 may process the input by comparing it to one or more threshold values, and determine that the user's blood glucose is low. The processor module 214 may produce an output in the form of an alert. If the user does not respond to the alert by pressing a button or an area on a touchscreen user interface 222, for example, the processor module 214 may determine that the user may be unconscious, and produces another output in the form of the emergency response instruction mode described herein.

In various other embodiments, the processor module 214 may provide differentiated visual high/low thresholds versus alert thresholds. For example, the processor module 214 may be programmed with low and high blood glucose thresholds. These thresholds may be shown on a blood glucose trend graph on the user interface 222 as horizontal lines that the user should strive not to cross. Ordinarily, crossing either of the lines might generate an alert. However, excessive alerts can be annoying to the user, and can decrease patient compliance. Thus, in some embodiments, the visual high/low target range boundaries shown on the graph may be different from boundaries that generate an alert. For example, the boundaries that generate an alert might be wider than the visual target range threshold boundaries on the user interface 222, and the boundaries that generate an alert may be hidden from view. This configuration gives the user a little bit of a buffer zone to cross either of the visual boundaries without generating an alert. Alternatively, the boundaries that generate an alert might be visible, but distinguishable from the target range boundaries. Examples of visual distinctions include different colors, flashing vs. static, solid vs. dashed, different line weights, an alarm icon adjacent the alarm lines, etc. In some embodiments, the high/low target boundaries may always be displayed, but the alert boundaries may be shown or not based on a user setting, a mode (e.g. silent), thresholds, etc.

In various other embodiments, a user interface of the processor module 214 may be the first thing that the user sees when he or she activates the smartphone's user interface 222. For example, many smartphones 18 automatically put the user interface 222 to sleep (e.g., in a sleep mode) when no activity is detected for a predetermined amount of time. This measure saves battery power. To reactivate the user interface 222, the user must press a button on the smartphone 18. In certain embodiments, when the user reactivates the user interface 222, the first thing he or she sees is the user interface of the processor module 214. In these embodiments, the processor module 214 receives as an input a notification that the user interface 222 has entered sleep mode, followed by a later notification that the user interface 222 has been reactivated. The processor module 214 may process these inputs and produce as an output a display of the user interface 222 of the processor module 214 on the smartphone 18.

In various other embodiments, a trend graph displayed by the processor module 214 is color coded. For example, with reference to FIG. 4E, the color of the graph 400 (either the trend line 402 or the background 404) may be green if within a target range, yellow if ±10% outside the target range, orange if ±15% outside the target range, and red if ±20% outside the target range. A trend arrow 406 may be similarly color coded, and the angle at which the trend arrow 406 is oriented may correspond to the actual rate of change of the user's glucose, e.g. a more horizontal arrow indicates a low rate of change, while a steeply sloping arrow indicates a high rate of change. In these embodiments, the processor module 214 may receive as inputs continuous EGV's from a sensor system 8. In some embodiments, the rate of change is calculated by the sensor system 8 and sent to the processor module 214 for display (e.g., determination of how to display and resulting display), although the processor module 214 may also perform rate of change calculations. The rate of change based on a linear or non-linear function is applied to a window of recent sensor data. In some embodiments, the rate of change calculation comprises calculating at least two point-to-point rate of change calculations, and wherein the rate of change calculation further comprises adaptively selecting a filter to apply to the point-to-point rate of change calculation based at least in part on a level of noise determined. The processor module 214 may output these values as data points on the trend graph 400 on the user interface 222 and also updates the value 408 shown in the box containing the user's most recent EGV. If the user's blood glucose is dropping, the processor module 214 outputs this information by orienting the arrow 406 downward, while if the user's blood glucose is rising the processor module 214 outputs this information by orienting the arrow 406 upward. In some embodiments, the trend arrow is located on the end of the trend graph (e.g., rather an in a separate box/area).

In certain embodiments, a size of the value 408 shown in the box containing the user's most recent EGV may change size depending on how far off the user is from their target zone. For example, as the user's glucose gets farther and farther away from the target zone, the number could get bigger and bigger. This amplification could be one directional or either direction, meaning the EGV displayed on the trend graph could get bigger and bigger if it's outside the target range in either direction or only get bigger and bigger if it's outside the target range on the low side (e.g., hypo). The same applies to the trend arrow 406. With reference to FIG. 4F, the trend arrow 406 could be drawn large enough to fit the EGV 408 inside the arrow 406. The layout of the trend arrow 406/EGV 408 in FIG. 4F may be used independently of the foregoing embodiment in which the size of the trend arrow 406/EGV 408 changes dynamically as the user's glucose changes.

In various other embodiments related to that of FIG. 4E, rather than using a hard threshold for the transition from one color to the next, the display could instead show a gradient type of trend graph. That is, rather than transitioning directly from green to yellow as soon as the user's glucose hits the threshold of, say ±10% outside the target range, the display would instead gradually transition from green to yellow as the user's glucose moves away from the target range toward the established threshold. Thus, at ±5% outside the target range, the display would show a color between green and yellow, with the color becoming gradually more yellow as the user's glucose moves through ±6% outside the target range, ±7% outside the target range, ±8% outside the target range, etc.

Predictive Alerts/Alarms

In some embodiments, the sensor outputs a signal in the form of electrical current; however any output signal from any measurement technique may be used for the predictive alerts/alarms described herein. In general, a conversion function is applied to the sensor signal in order to produce a user output that the user understands as representative of a concentration of analyte in his or her bloodstream. Such a proper conversion function may take into account numerous variables, e.g., sensitivity (slope), baseline (intercept), drift, temperature correction, factory-derived information or other calibrations or adjustment to the data. After a suitable conversion function is applied, the user may see an output similar to that shown in e.g., FIGS. 3A to 3D.

In the scope of preventing the consequences of diabetes, it is desirable to prevent hypoglycemia and/or hyperglycemia episodes instead of simply generating alerts when such episodes occur. For example, an alert generated to indicate that without intervention a hypoglycemia episode will occur within 20 minutes would allow the host or patient to ingest and absorb sugar in time.

Figure 5:
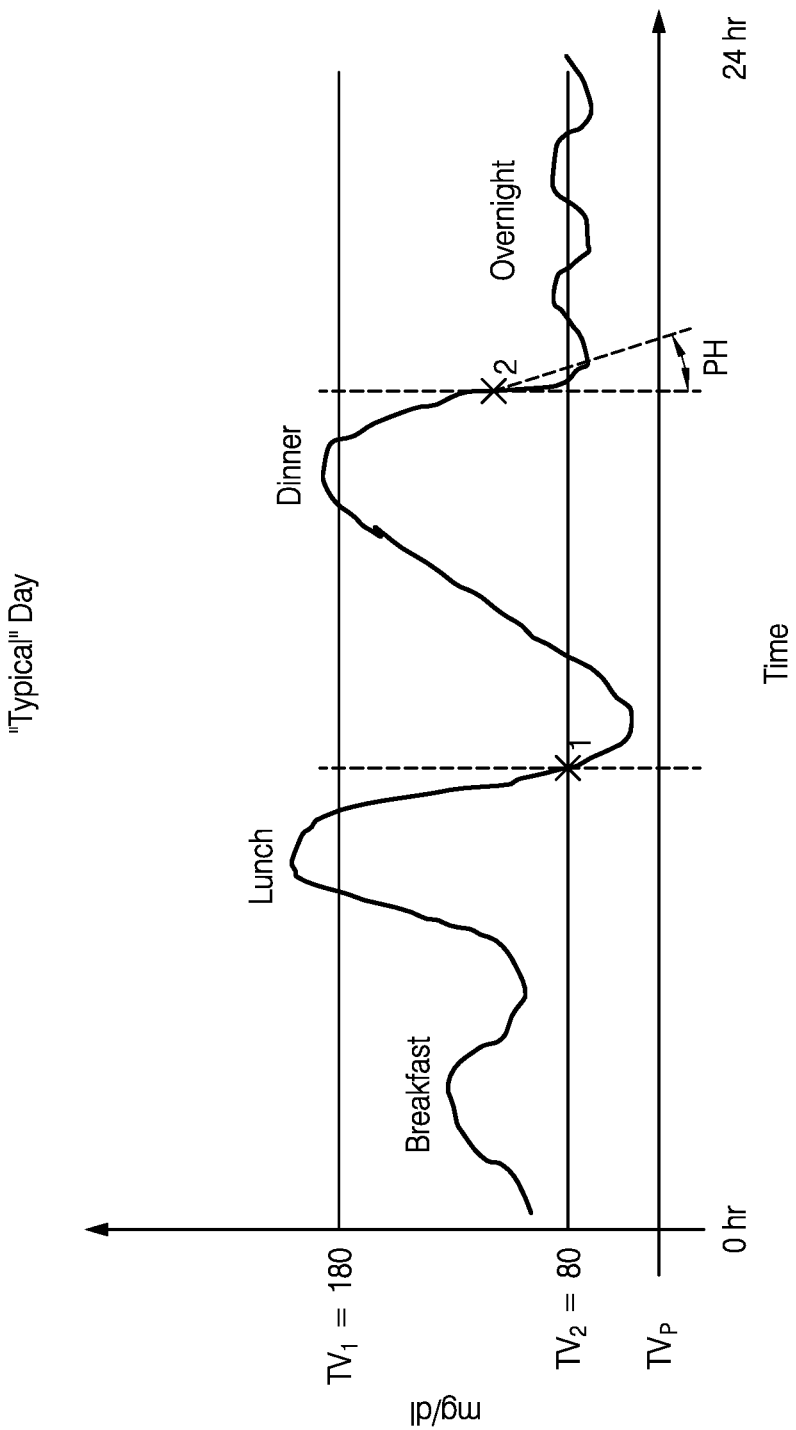
FIG. 5 is an illustration of a continuous trace of glucose values measured during a time frame in accordance with an embodiment of the disclosure.

Referring now to FIG. 5, an example of a continuous trace of glucose values measured during a time frame and having a threshold flag $x_1$ and a predictive flag $x_2$ located thereon is shown. As presented in FIG. 5, the example glucose trace embodies a graph having a glucose level e.g., mg/dl, compared against a time frame e.g., 24 hours.

As shown, there are three threshold values or limits used in the monitoring of the glucose values in some embodiments: $TV_1$, $TV_2$ and $TV_P$. $TV_1$ may be settable by the user and generally defines the upper limit or upper glucose value that a user may operate at before being alerted by the monitor. Similarly, $TV_2$ may be settable by the user and generally defines the lower limit or lower glucose value that a user may operate at before being alerted by the monitor. $TV_P$ is the predictive threshold, e.g., the threshold against which a predicted value is compared. It should be appreciated that although the illustrated embodiment envisions a threshold value, threshold ranges or other criteria (e.g., glycemic states) may alternatively be used.

As shown, $TV_P$ does not have a particular glucose value given. This is because $TV_P$ may not be settable by the user; it may be a fixed value or permanent value set during factory settings. In some embodiments, $TV_P$ may represent a dangerously low glucose value e.g., be indicative of a serious hypoglycemic event. In some embodiments, $TV_P$ may represent a value at or around 55 mg/dL.

In some embodiments, $TV_P$ may be adaptively determined based on $TV_2$. For example, if the user sets $TV_2$ to be a relative high value, e.g., 90 mg/dL, an algorithm or function may determine that $TV_P$ should be set at 65 mg/dL. Conversely, if the user sets $TV_2$ to be a relative low value, e.g., 70 mg/dL, an algorithm or function may determine that $TV_P$ should be set at 55 mg/dL. Additionally or alternatively, the prediction horizon, PH, may be preset or adaptively selected based on another parameter associated with prediction, for example, based on $TV_2$ selected and/or $TV_P$.

Still referring to FIG. 5, there are shown two flags $x_1$ and $x_2$. Flag $x_1$ may generally be considered a threshold flag, and may be configured to alert the user that a first threshold, e.g., $TV_2$, has been met. In some embodiments, threshold flag $x_1$ operates to notify the user in real time, or approximately real time (e.g., may take into account processing delay, etc.) when a threshold has been met or crossed. An example of using threshold flag $x_1$ is when the user wants to be notified of when his glucose level hits a certain value, high or low. When the user's glucose value is determined to meet that predetermined user set value, the user may be notified via an alert or alarm. Additional rate of change conditions may be added (e.g. $TV_1$ and rate of change increasing at >0.5 mg/dL/min or $TV_2$ and rate of change decreasing at >0.5 mg/dL/min).

Flag $x_2$ may generally be considered a predictive flag, and may be configured to alert the user that a second threshold, e.g., $TV_P$, is predicted to be met within a predetermined or predefined time frame or time horizon PH. In some embodiments, predictive flag $x_2$ operates to notify the user in real time that a threshold is predicted to be crossed or met in a predefined time frame, e.g., 20 minutes.

An advantage of the glucose monitoring profile shown in FIG. 5 is that prediction may be paired with a threshold alert that is settable by the user, where an alert will sound for whichever condition is met first (threshold or prediction) Use of prediction algorithm parameters (e.g., reliance on modeled versus measured data, time-sensitive weighting of past data, prediction horizon PH, and prediction threshold $TV_P$) tuned in advance may increase or optimize warning time for patients before a severe event occurs and may minimize the number of nuisance/false alarms heard by user.

In some embodiments, the prediction parameters ($TV_P$ and PH) may be invisible to the user and preset or fixed. In some embodiments the prediction parameters are determined from the sensor manufacturer using a variety of historical data using e.g., the user's historical data, a population historical data, the particular sensor's historical data, etc.

Referring back to FIG. 3A, an example glucose trace of a user's day is shown. From looking at the trace, it can be appreciated that the glucose trace generally falls within a shaded or bound region 246. This region may be generally referred to as a "target zone", and the user is encouraged to "stay between the lines". This region is generally viewable to a user on their monitor or device with a viewing screen as can serve as a quick check on how a user's glucose looked for a particular time period. Another example of the bound region is shown in FIG. 4A and designated as reference numeral 182.

In some embodiments, this shaded "target zone" differs from the region defined by $TV_1$ and $TV_2$, hereinafter referred to as the "alert boundary". In some embodiments, $TV_1$ and $TV_2$ are not viewable by a user, but are rather internal values used by appropriate algorithms or functions to e.g., alert the user when necessary.

In other embodiments, the alert boundary may be viewable to the user. It should be appreciated that values, pictures or icons, or simple designations such as "HIGH" and "LOW" may be associated with $TV_1$ and $TV_2$, respectively. Additionally, $TV_P$ may be shown, as a simple alarm icon, for example.

In some embodiments, the predictive alerts may be activated using a simple on/off button. Additionally, in some embodiments, there may be one or more general settings for prediction such as "sensitive", "normal", "non-annoying" for different user needs. For example, a sensitive prediction setting may use a PH=30 minutes and $TV_P$=70 mg/dL; a normal prediction setting may set values at PH=20 min and $TV_P$=55 mg/dL; and a non-annoying prediction setting may set values at PH=10 min and $TV_P$=55 mg/dL.

It should be noted that, although the disclosure focuses on prediction horizon and criteria associated with prediction at low glucose (hypoglycemia), all of the principles applied to hypoglycemic alarms/alerts may be implemented for high glucose (hyperglycemia) as may be appreciated by one skilled in the art.

Figure 6:
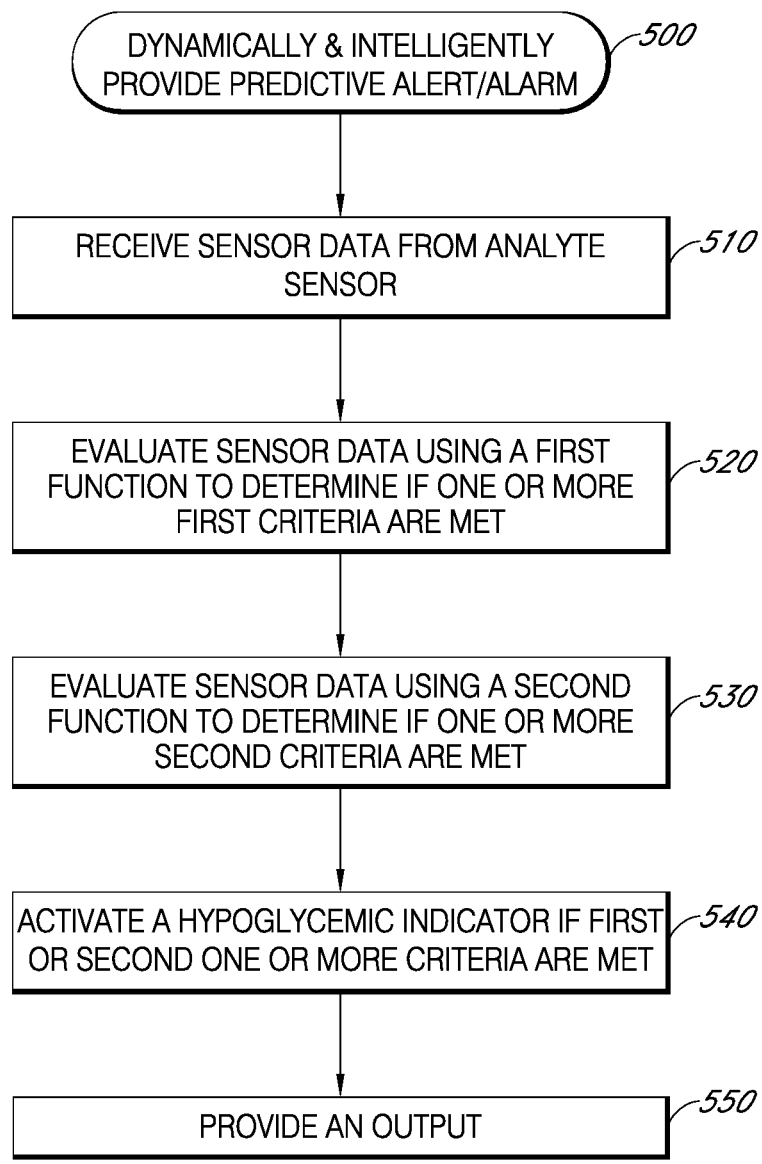
FIG. 6 is a flowchart illustrating a process for dynamically and intelligently providing a prediction alert/alarm in accordance with an embodiment of the disclosure.

FIG. 6 is a flowchart 500 illustrating a process for dynamically and intelligently providing a prediction alert/alarm in accordance with an embodiment of the disclosure. As explained above, providing a predictive alert/alarm is highly desirable as it may minimize and/or prevent the number of hypoglycemia and/or hyperglycemia episodes a user experiences.

At block 510, processor module 214 may be configured to receive sensor data (e.g., a data stream), including one or more time-spaced sensor data points, from the sensor 10. The sensor data point(s) can be averaged, smoothed, and/or filtered in certain embodiments using a filter, for example, a finite impulse response (FIR) or infinite impulse response (IIR) filter.

At block 520, processor module 214 may be configured to evaluate the sensor data using a first set of instructions or criteria. The first set of instructions or criteria may include any algorithm suitable for determining if a data point has met one or more first predetermined criteria associated with hypoglycemia or hyperglycemia. Such predetermined criteria may be input by the user using e.g., a menu for inputting various alert thresholds. Alternatively, the predetermined criteria may be set according to factory settings and may be fixed, such that the user cannot change, e.g., the alert threshold. In some embodiments, the predetermined threshold is saved in e.g., a lookup table, and may depend on other parameters such as time of day (e.g., more or less sensitive at nighttime), historical patient information, or the like. In other embodiments, more complex algorithms may be used to define a user's current glycemic state, rather than static thresholds, such as static risk or dynamic risk models, where the criteria would be defined based on the output of these complex algorithms or instructions (e.g., gradients, yes/no indicators, percentages, probabilities, or the like).

In some embodiments, the sensor data comprises real time glucose values (e.g. blood glucose values (BGs)), calibrated glucose values (e.g., estimated glucose values (EGVs)), rate of change of glucose values, direction of change of glucose values, acceleration or deceleration of glucose values, insulin information, event information, historical trend analysis results, and the like. Consequently, in some embodiments, the processor module 214 may be configured to evaluate sensor data using a first function to determine whether a real time glucose value meets one or more first predetermined criteria.

In some embodiments, the criteria may be thought of as including at least one component. For example, the criteria may be representative of a singular or absolute value. In some embodiments, the criteria may comprise two or more components. For example, the threshold may be representative of a range of values. Alternatively, the threshold may be representative of a singular value associated with a time component. In other embodiments, the threshold may be representative of a singular value associated with a direction or rate of direction.

As mentioned above, the one or more criteria may be a first threshold value set by a user. For example, the user may decide that he wants to be alerted whenever his glucose reading drops to 70 mg/dL or 70 mg/dL and rate of change is negative (indicative of decreasing glucose level). In other cases, the user may decide that 70 mg/dL might be to too low of a reading, and wants to be alerted whenever his glucose drops below 80 mg/dL. As understood by those of skill in the art, there is a fine balance between being alerted too often, e.g., nuisance alarms, and being adequately alerted when there is a real event. Consequently, the user may be allowed to have some input on how often he is alerted, based on selecting the first threshold value. The higher the selected value, the more sensitive the alert trigger, e.g., the more often a user is going to be alerted.

In some embodiments, the first threshold may be a user settable number or a qualitatively sensitive indication for the threshold being crossed. The qualitatively sensitive indication may include settings such as "sensitive", "normal", "non-annoying", etc., as described above. For example, the analyte monitoring system 8 may detect a high number of alerts (e.g., >2 a day) and prompt the user with a question to determine if settings should be adjusted to avoid unnecessary annoyances. For example, system 8 may suggest to the user to change the qualitatively sensitive indication from sensitive to normal or from normal to non-annoying if a higher than usual number of alerts (e.g., twice as usual) are being provided.

In some embodiments, the first set of instructions or criteria may include any algorithm suitable for determining if a data point has met or crossed a predetermined threshold. In some embodiments the first set of instructions or criteria may include a more complex assessment of glycemic state, including for example, other parameters such as amplitude and/or direction of rate of change of glucose, rate of acceleration/deceleration of glucose, insulin and/or meal consumption. In some embodiments, the first set of instructions or criteria may use a measure of risk, such as the static risk and/or dynamic risk models for continuous glucose monitoring data to generate and determine whether a particular criterion has been met. In some embodiments, the algorithm performs its calculations on uncalibrated sensor data, after which the results are converted into calibrated data and compared to the criteria and/or threshold. Performing some or all of the algorithmic processing on uncalibrated data may be advantageous to reduce negative impacts of error or bias associated with calibration; however in some embodiments, the algorithmic processing may be performed on calibrated data.

In other embodiments, more complex algorithms may be used to define a user's predicted glycemic state, rather than static thresholds, such as static risk or dynamic risk models, where the input could include real-time or predicted values and where the criteria would be defined based on the output of these complex algorithms (gradients, yes/no indicators, percentages, probabilities, or the like).

At block 530, processor module 214 may be configured to evaluate the sensor data using a second set of instructions or criteria. In some embodiments, the first set of instructions from block 520 is different than the second set of instructions from block 530.

Similar to block 520, in block 530, the second set of instructions or criteria may include any algorithm or algorithms suitable for evaluating sensor data to determine whether a glycemic state (hyper- or hypo-glycemia) is predicted, for example, by determining if a data point is predicted or projected to cross a predetermined threshold. Suitable algorithms include algorithms based on polynomial and autoregressive models, algorithms based on Kalman Filtering (KF), artificial neural networks, statistical and numerical logical algorithms, and machine learning.

In some embodiments, the second set of instructions may use utilize an artificial neural network that can consider other relevant information, if available, such as food, exercise, stress, illness or surgery to predict a future glucose value. The architecture may include three layers, with a first layer gathering the inputs, a hidden layer that transforms the inputs using polynomial or non-linear functions, e.g. squaring, sigmoidal, thresholding, and a third output layer that combines the outputs of hidden layer into output or predicted value(s). Neurons may be totally connected and feedforward. One useful artificial neural network implementation is described by W. A Sandham, D. Nikoletou. D. J. Hamilton, K. Patterson. A Japp and C. MacGregor, in "Blood glucose prediction for diabetes therapy using a recurrent artificial neural network," in *IX European Signal Processing Conference (EUSIPCO)*, Rhodes, 1998, pp. 673-676. Each neuron in second and third layers takes as input a weight combination of outputs from the previous layer. These weights are tuned to give the best predicted value through a process called training. That is, a neural network starts with an initial guess and using training and testing data sets with known input and outputs, finds the best possible weights to give optimal outputs. Once the training process is complete, the network may be used to predict outputs for any new data. The network input information may be the current glucose measurement and its timestamps together with a limited number of previous glucose samples from the CGM system. The NNM (neural network model) may take into account the glucose measurements up to 20 minutes before the current time. Since the sampling rate varies from one CGM system to another, the number of the NNM inputs may be different for each dataset. The output of the network may be the glucose prediction at the prediction horizon time.

In some embodiments, the second set of instructions may use an autoregressive model (first order, second order or third order, for example) to predict a future glucose value. One useful first-order autoregressive model implementation is described by G. Sparacino, F. Zanderigo. S. Corazza, A. Maran, A. Facchinetti and C. Cobelli, in "Glucose Concentration can be Predicted. Ahead in Time From Continuous Glucose Monitoring Sensor Time-Series." Biomedical Engineering. IEEE Transactions 011. 2007, voL 54, pp. 931-937. This algorithm predicts the future glucose value by taking the current glucose value y(n) and multiplying the previous glucose value y(n−1) by some coefficient $\alpha$. When glucose is rising, $\alpha$ will be some value slightly larger than 1 and when it is falling a will be a little less than 1. In this algorithm, the model parameter ($\alpha$) may be estimated recursively (e.g., updated every 5 minutes to account for glucose dynamics) to minimize the sum of squared residuals for all pairs of predicted and current glucose values. An estimate of alpha may be updated (e.g., using a weighted least squares regression) every time a new sensor data point is received (e.g., every 5 minutes). Prediction parameters (e.g., forgetting factor, prediction horizon, and prediction threshold) may be tuned in advance to optimize warning time for patients before a severe hypo event occurs (e.g., 55 mg/dL), and to minimize the number of nuisance/false alerts heard by patient. For example, the direction of glucose changes over time, so a forgetting factor $\mu$ may be used to weight the most recent data more heavily with a value between 0 and 1. Prediction horizon and/or prediction thresholds may be predetermined by the system and/or user selectable as described in more detail elsewhere herein.

In some embodiments, the first order autoregressive model includes a forgetting factor, a prediction horizon and a prediction threshold tuned to provide no more than one additional alarm per week based on a retrospective analysis comparing the use of the first function and the second function together as compared to the first function alone. In some embodiments, this is at least partially achieved by monitoring the user's qualitatively sensitive indication and prompting or urging the user to select the appropriate setting.

In some embodiments, the second set of instructions may use a Kalman filter (an optimal estimation method) to predict a future glucose value. The Kalman filter trades off the probability that a measured glucose change is due to sensor noise versus an actual change in glucose, to obtain the maximum likelihood estimate of glucose (and its first and second derivatives). One useful Kalman Filter implementation is described by Palerm, C. and Bequette, W. in "Hypoglycemia Detection and Prediction Using Continuous Glucose Monitoring—A Study on Hypoglycemic Clamp Data," J Diabetes Sci Technol. 2007 September; 1(5): 624-629. The states are the blood glucose concentration ($g_k$), its rate of change ($d_k$, e.g., the velocity), and the rate of change of the rate of change ($f_k$, e.g., the acceleration). The latter is assumed to vary in a random fashion, driven by input noise $w_k$ (with covariance matrix Q), which describes changes to the process. The sensor glucose measurements are assumed to contain noise, described by $\upsilon_k$ (with covariance matrix R). Prediction model parameters (e.g., Q/R ratio, prediction horizon, and prediction threshold) may be tuned in advance and/or user selectable.

In some embodiments, the second set of instructions or function may optionally include a mechanism to include user input, such as insulin, exercise, meals, stress, illness, historical patient information (e.g., patterns or trends), etc.

In some embodiments, the sensor data comprises real time glucose values, (e.g. blood glucose values (BGs)), calibrated glucose values (e.g., estimated glucose values (EGVs)), rate of change of glucose values, direction of change of glucose values, acceleration or deceleration of glucose values, insulin information, event information, historical trend analysis results, and the like Consequently, in some embodiments, the processor module 214 may be configured to evaluate sensor data using a second function to determine whether a predicted glucose value meets one or more predictive alarm criteria.

The second predetermined criteria may include a single value, a range of values, a direction associated with the value, a rate of direction, etc. In some embodiments, the second criteria include a predetermined threshold, which is a fixed value set as part of factory settings. For example, it may be desirable to have a second threshold that the user cannot manipulate or change because of the importance associated with the threshold. For example, in some embodiments, the second predetermined threshold may represent a value that is indicative of a severe hypoglycemic event, e.g., 55 mg/dL.

In some embodiments, the second predetermined criteria is determined based on a probability of hypoglycemia within a particular time frame, which may account for the rate at which sensor data is changing, the direction the sensor data is going, the current glucose level, past history of glucose change, insulin information, meal information, exercise information, etc. An example of applying additional criteria to the processor module 214 is that if hypoglycemia is predicted in the near future but the current glucose level is 200 mg/dL then that prediction is not probable or likely, thus, limits on glucose value, rates of changes, and the like, may be applied. Another example, this time of using meal information, is that if the user indicated that they recently ate a meal, then it may be the glucose will quickly turn around and it is not necessary to alert them at this time.

In some embodiments, the second predetermined criteria may be at least partially or adaptively based on the first predetermined threshold. For example, a suitable set of algorithms or functions may base e.g., the prediction horizon and/or the second predetermined threshold on the first predetermined threshold.

In some embodiments, the second set of instructions is completely predictive, meaning that the instructions use past and/or current data to determine if a user will meet or cross through the second predetermined threshold in a predetermined time frame or horizon. The predetermined time frame or horizon is preferably long enough for a user to take action to turn around a predicted event. For example, the predetermined horizon may be at least 15 minutes in some embodiments, at least 20 minutes in some embodiments, and at least 30 minutes in some embodiments.

In some embodiments, the predetermined time frame or horizon may have addition capabilities or take additional information into consideration when setting the time frame. For example, as is known by those of skill in the art, some continuous glucose monitoring systems sense glucose in the interstitial fluid, rather than blood (e.g., capillary blood from which finger stick measurements are traditionally derived). Consequently, there may be a time lag between the value measured and the actual blood glucose value, e.g. 5 minutes or more. In some examples the time lag can be as small as 0 minutes, where in other examples the time lag is as large as 15 minutes or more. There may also be variability in the time lag, which may be represented by a standard deviation in the measurement, e.g., 10 minutes for a 5 minute lag.

As sensors become more accurate through improved sensor design, the inaccuracy due to time lag may become a more substantial contributor to the total error. While not wishing to be bound by any particular theory, it is suspected that physiology, time since the sensor was inserted, glucose state (hypo- or hyper-), glucose rate of change, knowledge of filtering performed, and other variables may influence the amount of time lag a sensor will experience. Consequently, in some embodiments, a time lag adjustment algorithm or set of instructions may be used in determining or in conjunction with setting the predetermined time frame or time horizon. In some embodiments, the time lag adjustment set of instructions uses near time prediction to predict and display the estimated glucose value at a future point in time, e.g. from about 2.5 minutes to about 15 minutes, depending on additional information e.g., obtained through algorithmic or alternate detection means. For example, information that may influence the prediction horizon include: time since the sensor was inserted, glucose state or rate of change, adaptive learning algorithms that can learn what each individual's average time lag is and apply a unique setting, etc. Consequently, in some embodiments, a time adjustment lag algorithm may use as one or more inputs, one or more of the following variables: time since the sensor was inserted, glucose state or rate of change, user a priori information. In some embodiments, additional sensors may be implemented to directly or indirectly measure time lag. An example sensor could be the use of impedance data between the working and reference electrodes that are separated in space or between an electrode at the sensing area and a secondary electrode on the surface of the skin.

In some embodiments, blocks 520 and/or 530 may be iteratively repeated with the receipt of any new data, including data derived from the sensor, another medical device (e.g., insulin delivery device) and/or the user or host (via user input) prior to the activation of a hypoglycemic indicator.

At block 540, processor module 214 may be configured to activate a hypoglycemic indicator if either the first criteria is met or if the second criteria is predicted to be met. In some embodiments, the processor module 214 is configured to determine which set of instructions has met its criteria (e.g., 520 or 530 where $x_1$ or $x_2$ is flagged). For example, the first set of instructions may determine first threshold has been met at 8:47 pm in block 520, using real time data. In the same example, the second set of instructions may determine second threshold is predicted to be met at 9:00 pm in block 530, using the 20 minute prediction horizon. In this example then, where both the first and second evaluations have met their criteria, either or both may be used in subsequent processing.

As described above, the hypoglycemic indicator may comprise a single indicator representative of whichever function determines or predicts that a threshold will be crossed first in time. In some embodiments, the hypoglycemic indicator comprises a flag that has a particular set of instructions associated with it, depending on whether the first evaluation using the first criteria ($x_1$) or the second evaluation using the second criteria ($x_2$) were met. The responses to the first or second evaluations may also be differentiated in processing and/or output differently. In some embodiments, where both evaluations show criteria being met, there is unique processing and output indicating both actual and prediction-based criteria were met. Alternatively, rules may be provided to determine which criteria were met.

For example, in some embodiments, the $x_1$ and $x_2$ flags may be differentiated on the user display or user interface 222. In some embodiments, the user interface 222 may be configured to show the simultaneous display or both criteria ($x_1$ and $x_2$), such as "$x_1$ is at 76 mg/dL" and "$x_2$ is predicted to be at 55 mg/dL in 20 minutes."

At block 550, processor module 214 may be configured to provide an alert or alarm if warranted by the detection of a threshold being met or predicted to be met, as represented by the hypoglycemic indicator. In some embodiments, the processor module 214 provides an alarm or alert based on the detection of the threshold that is met or predicted to be met at an earliest time point. In some embodiments, providing an alert based on the earliest detected or predicted threshold is desirable because it may provide a user more time to turn around an actual or predicted a hypoglycemic and/or hyperglycemic event.

In addition to sending any of the above-described sensor data to an insulin delivery device, in some embodiments, the processor module 214 may send a message to an insulin delivery device including at least one of: a) suspend insulin delivery (e.g. configured to suspend a basal or bolus delivery of glucose in an insulin delivery device responsive to sensor data meeting a predetermined criterion), b) initiate a hypoglycemia and/or hyperglycemia minimizer algorithm (e.g. an algorithm configured to control a user's blood glucose to a target range using an automatic insulin delivery device), c) control insulin delivery responsive thereto or d) information associated with the alert (e.g., hypoglycemia indicator). Sensor data and/or messages may be sent directly to a dedicated insulin delivery device or indirectly through a controller, such as in a smart phone or via the cloud. Some embodiments provide the necessary sensor data useful for a hypoglycemic hypo-avoidance system to be sent to the insulin delivery device, for example, a hypoglycemic indicator may include information useful for determining when and for how long to suspend or reduce basal insulin delivery (e.g., predicted glucose value and prediction horizon, rate of change of glucose, static risk, dynamic risk) or may send the actual instructions (e.g., suspend basal delivery for 20 minutes).

In some embodiments, the alert and/or alert settings may be manipulated by a user or set one or more thresholds (e.g., from about 60-100 mg/dL). In some embodiments, the user can disable/enable the first and/or second functions. In some embodiments, a single message indicating an "early warning" or alert may be provided to the user. In some embodiments, particularly in the context of a closed loop or semi-closed loop systems, the settings are configured based on a control algorithm, which may be programmable or downloadable by a user.

In some embodiments, the alert may be selected from the group including: audible, tactile, visual and/or data transmissions (e.g., to a remote monitoring site) to subsequent audible, tactile and/or visual output to a user interface 222. For example, if a child host's alarm is activated, the data may be transmitted to a parent's smartphone (and the same or different alarm information may be provided). In such an example, the child host may receive an audible alarm, while the parent may receive a detailed glucose log. In some embodiments, if the first function determines that the first threshold is met first, an alert is provided to a user. In other embodiments, if the second function predicts that the second threshold will be met first, an alarm is provided to a user.

In some embodiments, a prediction alarm could trump a threshold alert to give a greater sense of urgency. For example, if the prediction alarm is associated with a reading of 55 mg/dL having a 20 minute prediction horizon, and the threshold alert is associated with a reading of 70 mg/dL, the prediction alarm indicator would be configured to control the alert screens and output.

In some embodiments, prediction alarm sounds/screens may convey a greater sense of urgency than the settable threshold alert. A rationale for having a differing sound/screen for alarms and alerts is to assist the user in understanding the difference between the two thresholds, e.g., that one may be a routine alert, while the other is indicative of a serious event. In some embodiments, whichever alert is met or predicted to be met first in time, is the alert conveyed to the user. It should be appreciated that these predictive and threshold alerts are different than target alerts, which may be used to "keep a user between the lines", such as described above with respect to FIGS. 3B and 4A. In some embodiments, information from the results of both the first and second sets of instructions may be combined and relayed on a user interface, whether or not they both met certain criteria. For example, a combined alert screen would include both a predictive alarm (e.g., an indication that the host is below the alert threshold ($TV_2$) and is predicted to be below predicted threshold $TV_P$ within 20 minutes or an indication that the host is below the alert threshold ($TV_2$) but is not predicted to be below predicted threshold $TV_P$ within 20 minutes). In some embodiments, additional information, such as therapy recommendations or requests for additional information may be displayed.

Once a hypoglycemic alert or alarm has been triggered, the processor module 214 may continue onto the post-alert monitoring, described in more detail below. Additionally or alternatively, where a system includes remote monitoring (e.g., a remote electronic device receiving and tracking a user, such as a parent's cell phone or a caretaker's personal computer), once a hypoglycemic alert has been triggered, and sent to the remote device, an increase in communication, data transmission, or the like, may be initiated to allow the caretaker or parent to more closely monitor the patient during hypoglycemic or predicted hypoglycemic events. The increase in communication or data transmission can include more frequent pushing and pulling of sensor data, additional input from or messaging to or from the remote device, or the like. The request for additional information may originate at the remote device and processor module 214 may be configured to receive and process such requests for additional information directly from the remote device.

Post-Alert Monitoring

Another issue commonly confronted with continuous glucose monitors, is that once an alert or alarm is triggered, the user may remain at or about the threshold value that triggered the alert, and may thereafter continue to trigger repeat or redundant alerts. Such alerts may be a nuisance to the user, causing them to suspend (e.g., snooze) alert/alarm feature of the monitor. A snooze that considers only time (e.g., rather than additional sensor data) may be undesirable, as there may be situations following the initial trigger of an alarm that would require an additional alarm to be provided to the user. If the user has suspended the alert/alarm feature, and suspend or "snooze" feature is solely time-based, the user may not be aware that they are in danger of approaching a hypoglycemic and/or hyperglycemic event during suspend or snooze time period.

Figure 7:
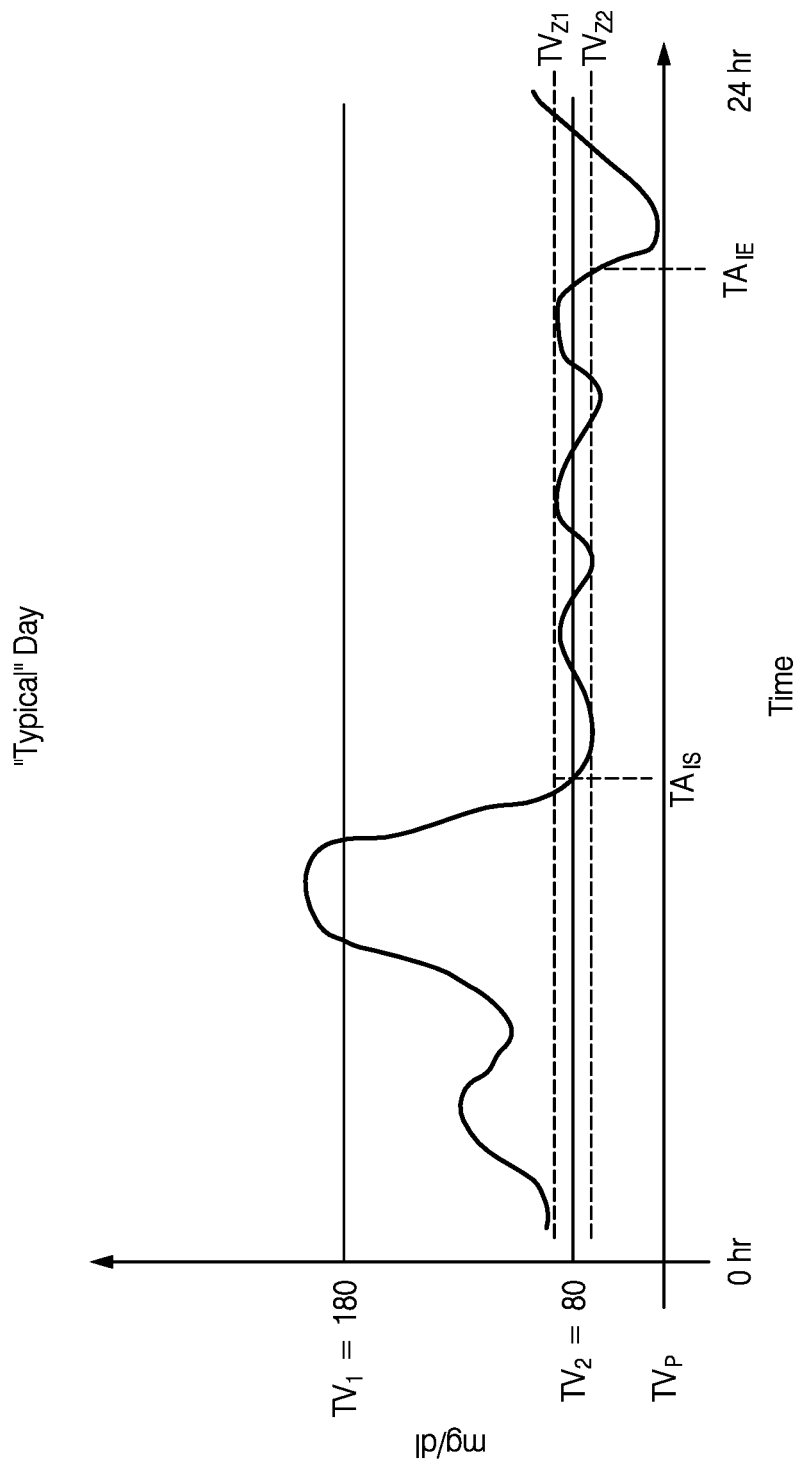
FIG. 7 is an illustration of a continuous trace of glucose values measured during a time frame in accordance with an embodiment of the disclosure.

Referring now to FIG. 7, an example of a continuous trace of glucose values measured during a time frame showing different scenarios that may cause an alert/alarm to be repeated is shown. Similar to FIG. 5, in FIG. 7, the example continuous glucose trace may embody a graph having a glucose level e.g., mg/dL, compared against a time frame e.g., 24 hours.

As shown, there are three threshold values or limits used in the monitoring of the glucose values: $TV_1$, $TV_2$ and $TV_P$. These values have already been discussed in the FIG. 5 discussion above.

In FIG. 7, there is a region or zone defined between a first and second time point $TA_{1S}$ and $TA_{1E}$. Time point $TA_{1S}$ may generally be referred to as a time that the first alert begins or starts. Assuming the user has acknowledged the alert soon after Time point $TA_{1S}$, Time point $TA_{1E}$ may generally be referred to as the time that the user's glycemic state changes. As shown, at $TA_{1S}$, a user may first be provided an alert that a threshold value $TV_2$ has been met. In the time interval following $TA_{1S}$, the user's glucose value generally hovers or oscillates around the same glucose level that triggered the initial alert, during which time re-alerts should not occur, and after which re-alerts should occur.

In some conventional systems, each time a user's glucose value would cross a threshold such as $TV_1$ and $TV_2$, the user would be alerted again that a threshold had been crossed. This would be annoying at best, and may even influence a user to turn off the alarms of the sensor following the first alert $TA_{1S}$. Further, if the user turned off or even "snoozed" or the one or more threshold alerts (e.g., at 80 mg/dl) using a simple time-based snooze, the user may not be aware of the worsening condition after $TA_{1E}$.

Still referring to FIG. 7, the region or zone where the glucose value oscillates may be further defined by a first and/or second glucose threshold $TV_{Z1}$ and $TV_{Z2}$. First glucose threshold value $TV_{Z1}$ may generally be referred to as the upper region or zone limit for a value that oscillates around e.g., $TV_2$. Second glucose threshold value $TV_{Z2}$ may generally be referred to as the lower region or zone limit for a value that oscillates around e.g., $TV_2$. In some embodiments, taken together, $TV_{Z1}$ and $TV_{Z2}$ provide a buffer zone, which also may be referred to as a margin (e.g., +/−5, 10, 15% or +/−5, 10, 15, 20 mg/dL) above and below a threshold value that would trigger an initial alert by which few, if any, repeat alerts are provided to the user. In other words, after the initial alert is provided to the user at $TA_{1S}$ and the user acknowledges the alert, the user may not be re-alerted until after $TA_{1E}$, e.g., when the glucose value exits the buffer zone (e.g., change in glycemic state). In some embodiments, $TV_{Z1}$ and $TV_{Z2}$ may have asymmetrical bounds and/or no lower bound (no $TV_{Z2}$). For at least the reason that the glucose trace scenario suggests, more intelligent and dynamic decision making may be advantageous such that a user is not overly alarmed in certain situations (e.g., between $TA_{1S}$ and $TA_{1E}$), but sufficiently alarmed in other situations (e.g., after $TA_{1E}$). Such a buffer zone, also referred to as margins or deltas herein, may be bidirectional and/or asymmetrical depending on the condition.

Figure 8:
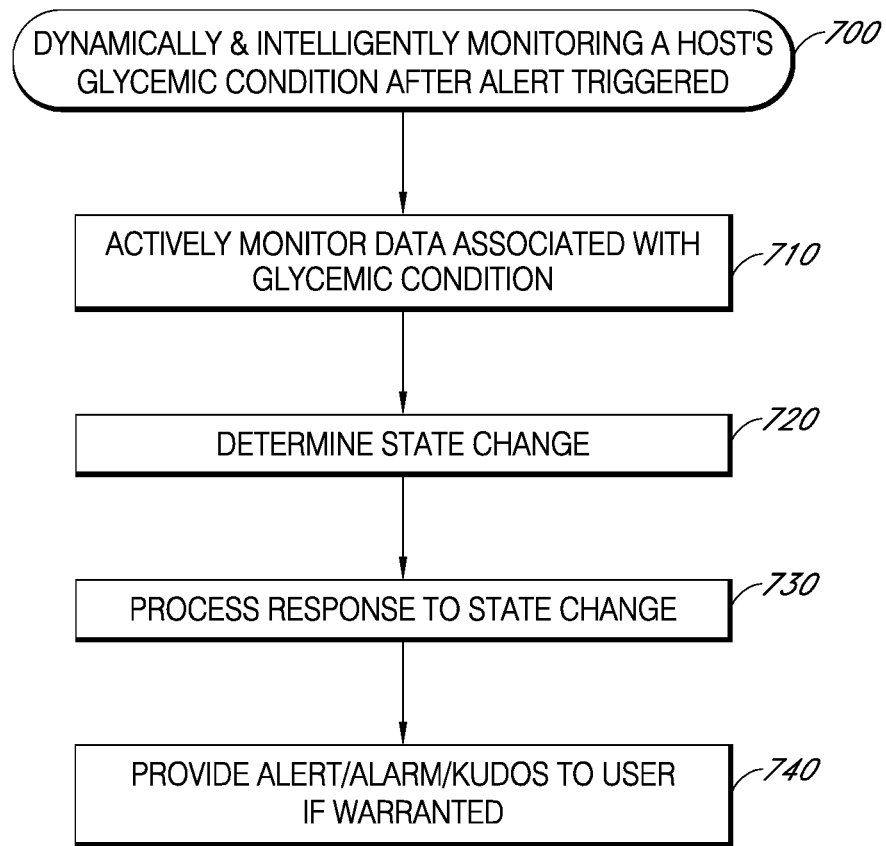
FIG. 8 is a flowchart illustrating a process for dynamically and intelligently monitoring the status after an alert/alarm has been triggered in accordance with an embodiment of the disclosure.

FIG. 8 is a flowchart illustrating a process 700 for dynamically and intelligently monitoring the hosts' glycemic condition after activating an alert state based on the sensor data meeting one or more active transition criteria associated with a hypoglycemic condition or hyperglycemic condition, for example, as described with reference to block 540. Additionally, post alert monitoring may be applied for any alarm or alert, whether evaluating against multiple criteria as in blocks 520 and 530, or simply compared against a single threshold (e.g., hypoglycemic or hyperglycemic threshold). In some embodiments, the triggering of an alert or alarm is merely the flagging or marking of the alert or alarm, for example, some hyperglycemic alert conditions include a wait time (e.g., 0 to 120 minutes), for example, an "enable wait before first alert" option that the user can set/enable. When this input enabled, the wait time will be applied before alerting the user for the first time, as described in more detail elsewhere herein, unless the actively monitoring determines a worsening condition.

In some embodiments, the triggering of an alert or alarm includes providing the alert or alarm to the user. In general, the processor module may be configured to provide an output associated with the active alert state, wherein the output is indicative of the hypoglycemic condition or hyperglycemic condition. In some embodiments, the post-alert monitoring will begin regardless of whether a user has acknowledged the alert, where the acknowledgement will alter the post-alert state as described elsewhere herein. In some embodiments, post-alert monitoring begins with a transition from the active state to the acknowledged state.

Criteria for triggering an alert, also referred to as transitioning from an inactive state to active state or activation criteria, may be any criteria or threshold associated with hypoglycemia or hyperglycemia. Activation criteria may include glucose value, predicted glucose value, rate of change of glucose (direction and/or amplitude), rate of acceleration of glucose (direction and/or amplitude), static risk models, dynamic risk models, or the like. Additionally or alternatively, activation criteria disclosed for transitioning 1055 from inactive state 1030 to active state 1010 may initiate the dynamic and intelligent monitoring the hosts' glycemic condition after activating an alert state associated with hypoglycemia or hyperglycemia.

At block 710, processor module 214 may be configured to actively monitor data associated with the host's hypoglycemic or hyperglycemic condition for a time period following the triggering or an alert/alarm to the user (e.g., as described in FIG. 6 and associated text) and/or user acknowledgement. In some embodiments, the user or host has acknowledged the initial alert. As described in more detail elsewhere herein, acknowledgement of an alarm may include a user interaction with the system ("user action"), such as a button or menu selection, or other data input (e.g., meal or insulin information entered). Additionally or alternatively, acknowledgement of an alarm may be based on monitoring of data associated with the glycemic state, including sensor data, insulin data, meal data, or the like. In some embodiments, the acknowledgement may come from a remote monitor, such as a parent's cell phone, or the like. Acknowledgement of an alarm may cause the processor module 214 to transition from the active state to the acknowledged state, during which active monitoring may occur.

In some embodiments, processor module 214 actively monitors data associated with the host's hypoglycemic or hyperglycemic condition for a time period in the acknowledged state or continuously while in the acknowledged state until a state transition to inactive (e.g. based on inactivation criteria). In some embodiments, processor module 214 monitors sensor data or other data received post-alert activation. For example, the data may include information such as: sensor data (e.g., glucose levels, trends, distances between peaks and valleys indicative of meal timing, etc), sensor diagnostic information (noise indicators), meal information (e.g., caloric intake and time of intake), insulin information, or other event information. In some embodiments, actively monitoring data includes determining an average glucose over a window of time, an amplitude and/or direction of rate of change of glucose or an amplitude and/or direction of rate of acceleration of glucose.

In some embodiments, processor module 214 tracks how quickly and/or how often the user acknowledges the alarms to determine further processing. For example, patterns that evaluate timing of user acknowledgement, information about the type of alert that was triggered and/or resulting recovery from the condition may be evaluated and future acknowledgements or alerts modified based thereon. In general, however, the processor module 214 may process alarms based on the assumption that a user acknowledgement of the alert/alarm indicates the user is aware of the conditions. Accordingly, re-alert conditions may be different, e.g., more stringent, in some embodiments, as described herein.

In some embodiments, the sensor data is actively monitored during the acknowledgement time period, also referred to as the active monitoring time period. Suitable time periods include, for example, 20 minute, 40 minute, 60 minute, etc., time periods, and may be user settable. Such time periods may commence or begin at the first data point following the alert or alarm triggering data point. In some embodiments, the user may be allowed to select the time period. In some embodiments, the post-alert sensor data monitoring continues until the alert is inactivated, as described in more detail elsewhere herein.

At block 720, processor module 214 is configured to transition from the acknowledged state to at least one of an inactive state or active state responsive to the data associated with the host's hypoglycemic or hyperglycemic condition meeting one or more predetermined criteria. The processor module 214 may determine if there has been a change in state based on the sensor data or other data associated with the host's glycemic condition. In some embodiments, the change in state may be indicative of a change in the host's glycemic condition.

In some embodiments, a change in state may be a positive event, such as an indication that a user has safely turned around a predicted hypoglycemic event, which may trigger the acknowledged state to recognize a sub-state of recovery and/or inactive state, as described in more detail elsewhere herein. In other embodiments, a change in status may be a negative event, such as an indication that a user has dropped further toward a hypoglycemic event (e.g., acceleration/deceleration analysis of the sensor data) for a particular time period (e.g., 20 minutes), with or without a sub-state of recovery being determined. In this second example discussing the negative event, it may be desirable to reactivate the alert, even when a user has acknowledged the alert. This second alert or alarm may be valuable in warning the user that his condition is declining—that whatever action he took following the first alarm, if any, was insufficient to turn around or improve his glucose reading. In some embodiments, a status change indicative of such a negative event may override an acknowledged state (described elsewhere herein), causing the system to transition back into an active alert state (also referred to as re-alert or reactivation). However, if the system was already in an active alert state (e.g., unacknowledged by a user), the resulting output may escalate, e.g., louder and more frequent, and/or may result in a communication with 911, a care taker, or the like.

In some embodiments, processor module 214 may be configured to determine no change has occurred over the last x minutes, for example 15, 30, 45 or 60 minutes, such as described with reference to conditions associated with remaining in a particular state (e.g., active state) and/or reactivation conditions as described in more detail elsewhere herein. No change may occur, for example, in situations where the data points are hovering around the threshold value that triggered the initial alert (e.g., with low rates of change). It may be appreciated that in such situations, each time a data point crosses the threshold in an undesirable direction, e.g., below a threshold for a hypoglycemic event or above a threshold for a hyperglycemic event, an alert or alarm would be triggered in conventional systems. This is typically thought of as a nuisance, and may be a reason a user would act to turn off his alerts or become desensitized to the alerts. In these situations, the intelligent post-alert monitoring algorithms would likely avoid these annoying alerts (e.g., as long as a user remains in the same state and/or reactivation conditions have not been met, which are described in more detail elsewhere herein).

As used herein, the user may be in different monitoring "states" such that processor module 214 can detect when the user transitions from one state to another. Examples of such states include, for example, "active", "inactive" and "acknowledged".

The active state is herein defined as an alert state post-alert trigger, where data is being monitored to determine whether to change the alert state to "acknowledged" or "inactive." The active state may be entered from an inactive and/or acknowledged state by comparing data (sensor, glucose, insulin, user provided information, etc.) against different criteria, respectively for each state transition. Re-alerts and/or reactivation of the alerts may occur in this state, which escalate the initial alert, even when an acknowledgement has not occurred.

The inactive state is herein defined as an alert state post-alert trigger, where evaluation of data indicates the glycemic state is in a safe or target zone. The inactive state may be entered from an active and/or acknowledged state by comparing data (sensor, insulin, user provided information, etc.) against different criteria, respectively for each state transition.

The acknowledged state is herein defined as an alert state post-alert trigger, where the user has acknowledged an alert and/or alarm and where no additional alerts/alarms will be provided for a predetermined time period, unless certain re-activation criteria are met (wherein the reactivation criteria are different and/or more stringent that the initial activation criteria, for example, which is described in more detail elsewhere herein). The acknowledged state may be entered from the active state based on user interaction and/or data indicative of a recovery from the hyper- or hypoglycemic condition. It should be appreciated that the terms used herein for the states and/or functions are merely descriptive and may go by other names, provided the functions remain substantially the same.

In some embodiments, a user may acknowledge an alert by pressing a button, selecting a menu screen, or the like. In some embodiments, a timer is set for a predetermined time period when the system enters the acknowledged state, after which predetermined time period the state may automatically transition into active and/or inactive based on selected conditions.

In some embodiments, the acknowledged state evaluates data associated with the hosts' glycemic condition (including glucose, meal and/or insulin information) and may transition into the acknowledged state based on the evaluation indicating the host's recovery from the glycemic condition that triggered the alert. The host's recovery may be also considered as a sub-state of acknowledged and may be determined by comparing data (sensor, glucose, insulin, user provided information, etc.) against different criteria, respectively for each state transition. Re-alerts may be suspended for some time period, when in the acknowledged state and/or acknowledged and recovering sub-state.

In some embodiments, if the user does not acknowledge the alert, the alert remains in active state. In some embodiments, if the user does not acknowledge the alert after X minutes (e.g., 5, 10, 15 minutes), the alert may be escalated via output to a secondary display device, a remote monitor, emergency contact, etc. Similarly, if the conditions worsens during active monitoring (e.g., in acknowledged state), the alert may be escalated via output to a secondary display device, remote monitor, emergency contact, etc.

An example showing the various transitions from one state to another is provided in the discussion of FIG. 11 below. It should be appreciated that using different states to describe that user or host's glycemic condition is useful in tracking the user's condition after an alert or alarm has been triggered. Thus, certain trends, such as a user's glycemic condition improving or just hovering about a non-serious alert may be reason enough to discontinue alerting the user. However, other trends, such as a user's rapid decline in glycemic condition or even hovering about a serious alert, may be reason to continue to warn or alarm the user. A number of suitable responses (e.g., associated with reactivation of an active alert) may be saved in an e.g., lookup table, depending on the state transition and other known information.

Figure 11:
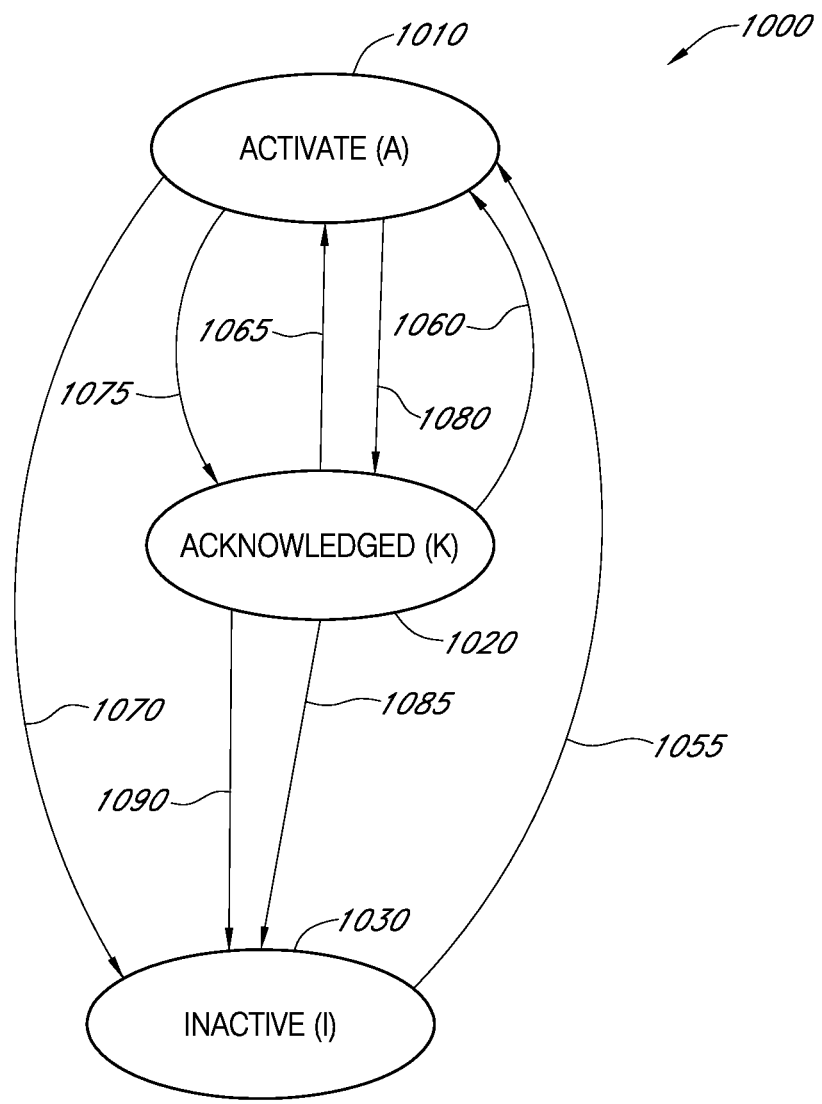
FIG. 11 is an illustration of a state diagram showing the transitions from various states in accordance with an embodiment of the disclosure.

Referring now to FIG. 11, a state diagram 1000 is provided that shows the transitions between the following states: active (A) 1010, acknowledged (K) 1020, and inactive (I) 1030. These states and their transitions may be described as follows:

Upon activation of an alert, the processor module transitions (1055) from an inactive state (1030) to an active state (1010). Conditions for activation include various criteria or thresholds, hereinafter referred to as "activation criteria" or "activation conditions", useful for detecting actual or upcoming hyperglycemia or hypoglycemia, such as described in more detail elsewhere herein (e.g., FIG. 6). Alert conditions are met as designated by reference numeral 1055. In addition to sensor data (glucose values, derivatives (rate of change) and double derivatives thereof (acceleration)), alert conditions may relate to other data including insulin data and/or user input (meal information, exercise information, etc.). Additionally, embodiments discussed herein with respect to reactivation may be applied here (e.g., analysis of static risk and/or dynamic risk). However, regardless of the detection method for an active hypoglycemic or hyperglycemic condition, the disclosed active monitoring and state transitions may apply.

In some embodiments, certain of the following activation conditions may apply for a state transition from inactive to active based on a hyperglycemic condition: the glucose level exceeds a predetermined threshold (e.g., 160, 180, 200, 220 mg/dL); the average glucose level over a predetermined time period (e.g., 10, 20, 30, 40 minutes) is more than a predetermined threshold (e.g., 160, 180, 200, 220 mg/dL); the current glucose level is more than a predetermined threshold plus a predetermined margin (e.g., 25, 50, 75 mg/dL); and/or the rate of change of glucose is greater than a predetermined threshold (e.g., −0.5 mg/dL).

In some embodiments, the following activation conditions may apply for a state transition from inactive to active based on a hypoglycemic condition: glucose level is less than a predetermined threshold (e.g., 80, 60, 60 mg/dL); glucose level is less than a predetermined threshold and rate of change is less than is a predetermined rate (1.0 mg/dL/min, e.g., not rising rapidly); or glucose level is predicted to go below a second threshold (e.g., 55 mg/dL) within a prediction horizon (e.g., 10, 15, 20 minutes).

In some embodiments, transitioning (1080) from the active state (1010) to an acknowledged state (1020) is based on data or acknowledgement criteria indicative of the host's glucose trending toward euglycemia, wherein the data may include sensor data indicative of a change in glucose trend and/or insulin information associated with a correction of the condition.

For example, upon activation of an alert indicative of hyper- or hypoglycemia, sensor data indicative of a change in glucose trend may include evaluating sensor data whereby a direction and/or amplitude of glucose level, rate of change of glucose level or acceleration/deceleration of glucose level indicative of a trend back toward euglycemia (e.g., change in direction or trend) is sufficient to automatically transition from active to acknowledged state (with or without user interaction with a user interface). A trend back toward euglycemia may also flag or trigger a "recovering" sub-state, which is a status within the acknowledged state indicative of trend back toward euglycemia. In one example, after an active transition associated with a hyperglycemic condition, a state transition to acknowledged, but recovering sub-state, may be based on an acknowledgement criteria or condition such as the glucose level (or average glucose level over a predetermined time period) is less than a predetermined threshold minus a delta (e.g., 10, 15, 20 mg/dL), and in some examples with a condition on rate of change trending toward euglycemia (e.g., decreasing faster than about 1 mg/dL/min). Similarly, after an active transition associated with a hypoglycemic condition, a state transition to acknowledged, but recovering sub-state, may be based on an acknowledgement criteria or condition such as the glucose level (or average glucose level over a predetermined time period) is greater than a predetermined threshold plus a delta (e.g., 10, 15, 20 mg/dL), and in some examples with a condition on rate of change trending toward euglycemia (e.g., increasing faster than about 1 mg/dL/min).

In some embodiments, transitioning (1075) from the active state (1010) to an acknowledged state (1020) is based on acknowledgement criteria indicative of a user acknowledgement of the alert on a user interface, user input insulin information and/or user input of meal information. For example, the user may hit a touch screen "button" to acknowledge the alert. Additionally or alternatively, when the continuous glucose sensor is operably connected to an insulin delivery device (including a remote programmer associated therewith), changes associated with basal or bolus delivery profiles or amounts may be considered as user input, particularly when the change was initiated by user interaction. Similarly, when the continuous glucose sensor is operably connected to an electronic device (or integral with the electronic device) capable of receiving meal information (e.g., carbohydrates and timing of consumption), such meal information may be considered as user input. In some embodiments, user input may come from another electronic device (e.g., via remote monitoring from a parents' smart phone, or the like).

In some embodiments, transitioning (1085) from the acknowledged state (1020) to the inactive state (1030) is based on the sensor data no longer meeting one or more active transition criteria associated with a hypoglycemic condition or hyperglycemic condition and/or based one or more inactive transition criteria (e.g., that may be different from the one or more active transition criteria associated with the a hypoglycemic condition or hyperglycemic condition (e.g., associated with the initial alert). Additionally or alternatively, transitioning (1080) from the acknowledged state to the inactive state may be based on insulin data and/or meal information. In some embodiments, transitioning (1090) includes a time element, for example, after the expiration of an acknowledgement (active monitoring) time period, which may be fixed and/or user settable.

Inactivation criteria for transitioning from acknowledged to inactive may be similar to or the same as conditions for inactive to active (except that acknowledged state would be entered when the one or more first or second criteria (e.g., see FIG. 6) were not met and/or for transitioning from active to inactive. In some embodiments, certain of the following inactivation criteria or conditions may apply for a state transition from acknowledged to inactive based on a hyperglycemic condition: the average glucose level over a predetermined time period (e.g., 10, 20, 30, 40 minutes) is less than a predetermined threshold (e.g., 160, 180, 200, 220 mg/dL); minus a predetermined delta (e.g., 10, 15, 20 mg/dL); the acknowledge time period has expired and the glucose level is less than a predetermined threshold (e.g., 160, 180, 200, 220 mg/dL); and/or the rate of change of glucose is dropping at a predetermined rate.

Alternatively, the inactivation criteria for transitioning from acknowledged to inactive may be different (e.g., more stringent). In addition to sensor data, other data including insulin data and/or user input may be considered for the state transition criteria. In some embodiments, the following inactivation criteria or conditions may apply for a state transition from acknowledged to inactive based on a hypoglycemic condition may include determining whether the glucose value has increased by more than a predetermined amount (e.g., 10, 15, 20 mg/dL, which may be indicative of some user action) and whether the glucose value has risen above the threshold condition (e.g., from the first function). Inactivation conditions for the real-time alert (first function) and predictive alert (second function) may be the same or different. In some embodiments, a positive glucose rate of change (increasing rise rate) exceeding a certain value may be used as a condition because it may be assumed that the rise rate is indicative of the user taking some preventive action. In some embodiments, the rise rate condition may be combined with a glucose value threshold condition. In some embodiments, the glucose value rise rate condition is 0.25, 0.5, or 1 mg/dL/min.

In some embodiments, in cases where a hypoglycemic condition has triggered an active state, and active monitoring after user acknowledgement, the state may transition from acknowledged state to inactive state prior to the expiration of the acknowledgement time period based on inactivation criteria or data indicative of hypoglycemic conditions significantly improving for example, a determination that the host's glucose level is greater than the low threshold plus a delta and the predicted glucose level for the prediction horizon is more than some predetermined limit (which may be the same or different from that prediction horizon or threshold of initial activation).

In some embodiments, transitioning (1060) from the acknowledged state (1020) to the active state (1010) is based on the one or more activation criteria associated with a hypoglycemic condition or hyperglycemic condition being met and based on an expiration of a predetermined time period. Activation criteria for transitioning from acknowledged to active may be any of the same conditions for initially alerting or may be different (e.g., based on glucose trending away from euglycemia). In addition to sensor data, other data including insulin data and/or user input may be considered for the state transition criteria. Additionally embodiments discussed herein with respect to reactivation may be applied here.

In some embodiments, reactivation criteria for transitioning (1065) from acknowledged state (1020) to active state (1010) may be different than criteria for initially transitioning to active state. For example, even when the user has acknowledged the alert (during the active monitoring and/or acknowledged time period), a worsening condition may indicate a need for a re-alert based on sensor data indicative of worsening glycemic conditions, such as the second function meeting one or more criteria and/or the sensor data indicative of glucose further trending away from euglycemia based one or more criteria indicative of worsening.

In some embodiments, the following reactivation criteria or conditions may apply for a state transition from acknowledged to active based on a hypoglycemic condition after acknowledged time has expired: glucose level is less than a predetermined threshold (e.g., 80, 60, 60 mg/dL); glucose level is than a predetermined threshold and rate of change is less than is a predetermined rate (e.g., 1.0 mg/dL/min, e.g., not rising rapidly); or glucose level is predicted to go below a second threshold (e.g., 55 mg/dL) within a prediction horizon (e.g., 10, 15, 20 minutes). However, in some embodiments, reactivation criteria indicative of a worsening hypoglycemic condition may case a state transition from acknowledged to active prior to expiration of the acknowledged time period (re-activation or re-alert) based on one or more re-alert criteria (e.g., different from criteria for initial alert), some of which are described in more detail elsewhere herein. In some embodiments, an alert activated by the first function (at 520) may trigger a re-alert or re-activation during the acknowledgement time period (transition to active prior to expiration of time period) if the second function meets the second criteria (at 530).

In some embodiments, the activation criteria associated with a hyperglycemic condition to transition from acknowledged to active may include a determination of whether: the glucose level exceeds a predetermined threshold (e.g., 160, 180, 200, 220 mg/dL); the average glucose level over a predetermined time period (e.g., 10, 20, 30, 40 minutes) is more than a predetermined threshold (e.g., 160, 180, 200, 220 mg/dL); the current glucose level is more than a predetermined threshold plus a predetermined margin (e.g., 25, 50, 75 mg/dL); and/or the rate of change of glucose is greater than a predetermined threshold (e.g., −0.5 mg/dL per minute).

In some embodiments, transitioning (1065) from the acknowledged state (1020) to the active state (1010), also referred to as reactivation, occurs after determining data is indicative of the host's glucose trending toward euglycemia, also referred to as the recovering sub-state, and the subsequently trending away from euglycemia during the active monitoring time period (based on one or more criteria). In other words, a rebound situation may occur, after an active alert, when a user's glycemic condition initially trends towards euglycemia (recovering), but subsequently trends back towards the hyper- or hypoglycemic condition. Accordingly, reactivating the first alert state during the acknowledgement time period may be by the data associated with the host's hypoglycemic or hyperglycemic condition meeting one or more rebound (e.g., reactivation) criteria indicative of a rebound situation. In general, criteria for transitioning from recovering to active may be any of the same conditions for initially alerting or may be different (e.g., a reversing trend of glucose value, rate of change or acceleration). In some embodiments, the one or more rebound criteria include conditions indicative of the host's glucose trending toward euglycemia (e.g., recovering substate) and subsequent conditions indicative of the host's glucose trending away from euglycemia during the active monitoring time period. In addition to sensor data, other data including insulin data and/or user input may be considered for the state transition criteria. Additionally embodiments discussed herein with respect to reactivation may be applied here.

In some embodiments, transitioning (1070) from active state (1010) to inactive state (1050) may be any of the same conditions for initially alerting (except that inactive state would be entered when the one or more first or second criteria (of FIG. 6) were not met). Alternatively, the inactivation criteria for transitioning from active to inactive may be different (e.g., different thresholds). In addition to sensor data, other data including insulin data and/or user input may be considered for the state transition criteria. In one example, a transition from active to inactive is based on the alert conditions no longer being met, e.g., EGV and delta EGV as described in more detail elsewhere herein.

In some embodiments, certain of the following inactivation criteria or conditions may apply for a state transition from active to inactive based on a hyperglycemic condition: the average glucose level over a predetermined time period (e.g., 10, 15, 30, 45 minutes) is less than a predetermined threshold (e.g., 160, 180, 200, 220 mg/dL) minus a predetermined delta (e.g., 10, 15, 20 mg/dL); the glucose level over a predetermined time period (e.g., 10, 15, 30, 45 minutes) goes below a predetermined threshold (e.g., 160, 180, 200, 220 mg/dL) minus a predetermined delta (e.g., 10, 15, 20 mg/dL); the average glucose level over a predetermined time period is less than a predetermined threshold; and/or the rate of change of glucose is falling (negative) at greater than a predetermined rate (e.g., 1 mg/dL/min).

In some embodiments, certain of the following inactivation criteria or conditions may apply for a state transition from active to inactive based on a hypoglycemic condition: the average glucose level over a predetermined time period (e.g., 10, 15, 30, 45 minutes) is greater than a predetermined threshold (e.g., 60, 70, 80 mg/dL) plus a predetermined delta (e.g., 10, 15, 20 mg/dL); the glucose level over a predetermined time period (e.g., 10, 15, 30, 45 minutes) goes above a predetermined threshold (e.g., 60, 70, 80 mg/dL) plus a predetermined delta (e.g., 10, 15, 20 mg/dL); the average glucose level over a predetermined time period is more than a predetermined threshold; and/or the rate of change of glucose is increase (positive) at greater than a predetermined rate (e.g., 1 mg/dL/min).

For example, in some embodiments, the criteria to get out of the acknowledged state, where the acknowledgement is based on data user acknowledgement (e.g., pressing button), to either an inactive state or active state (e.g., reactivation) are different from the criteria to get out of acknowledged state, wherein the acknowledgement is based on user action detected (e.g., recovery detected by monitoring of data). This acknowledgement based on user action detected is described in more detail below in the acknowledgement sub-state recovery discussion. For example, to go from the acknowledged state, where the acknowledgement is based on data user acknowledgement, to the inactive state, certain first criteria may apply (e.g., criteria that allow for oscillations around the threshold without inactivation occurring, or, in other words, criteria that ensure the user is not merely oscillating around the threshold). In contrast, to go from the acknowledged state, where the acknowledgement is based on user action detected (recovery sub-state), to the inactive state, certain second criteria may apply (e.g., the second criteria do not consider oscillations, but rather consider the data confirming the user's detected successfully recovered into euglycemia.

As mentioned above, the conditions or criteria for reactivation may be more stringent than for the initial activation. Similarly, the reactivation criteria to get out of the acknowledged state, where the acknowledgement is based on user acknowledgement (e.g., pressing a button), to the active state may be different from the reactivation criteria to get out of acknowledged state, wherein the acknowledgement is based on user action detected (e.g., recovery detected by monitoring of data). In some embodiments, the reactivation criteria for the transition from acknowledged (based on user acknowledgement) to active, may be time-based or could include a stringent second set of criteria (e.g., change greater than 200 mg/dL). In contrast, the reactivation criteria for the transition from acknowledged (based on user action detected, recovery sub-state) to active, may include recognizing a reversing trend or a worsening, etc. indicative of rebound conditions, based on monitoring of the sensor data.

Example worsening of conditions may include or be based on a strong change in glucose away from a target, and could be based on glucose level (g), amount of glucose change (Δg), rate of glucose change (Δg/t), rate of acceleration, or combinations thereof.

Referring back to FIG. 8, at block 730, processor module 214 may be configured to process a response to an alert state change or transition. In some embodiments, processor module 214 may include instructions or criteria on how to process an appropriate response for a status change. In some embodiments, such responses may be stored in e.g., a lookup table, or the like. In some embodiments, the output associated with a transition to the active state is different from the output associated with a transition from the acknowledged state to the active state and/or different from a transition from the acknowledged state to an inactive state.

It should be appreciated that depending on the status change there may be one or more possible and/or appropriate responses. For example, if sensor data indicates that a user has stabilized his glucose value and come down sufficiently from a hyperglycemic event (e.g., active to inactive state transition), a particular type of alert indicating a positive status change or kudos may be provided. The kudos may have a particular sound, e.g., particular pitch or number of chimes. In some embodiments, the user may be able to customize or select the alert signature, similar to that currently available to smart phone users.

In other embodiments, a particular type of alert indicating a negative status change or warning may be provided (e.g., transitioning back to active state). The warning may also have a particular sound and may, in some instances, be customizable by the user. In some embodiments, the severity of the warning may be reflected by the sound itself of the warning, e.g., the warning may be louder or more intense or maybe sound similar to a recognizable distress sound. In some embodiments, a re-alert or follow up alarm may be different than the initial alert.

State transitions are described in more detail elsewhere herein; however, it should be appreciated that any of a variety of indicators may be provided audibly, tactilely, visually and/or communicated via data transfer, based on preset or user selectable options.

At block 740, processor module 214 is optionally configured to output information associated with the state transition, for example, to provide an alert or alarm or kudos if warranted by the detection of a state or status change. In some embodiments, wherein the output associated with a transition to the active state is different from the output associated with a transition from the acknowledged state to the inactive state and/or active (reactivation) state. In some embodiments, the alert or alarm or kudos may be subject to a time restriction, e.g., such as if the user has pushed an acknowledgement on alerts. This may disable the user from receiving alerts/alarms/kudos in all but a handful of situations, such as where the alarm is characterized as a reactivation condition, as described in more detail with reference to FIG. 9.

Some use cases arise, wherein immediate notification of an alert may not be advantageous. For example, postprandial glycemic excursions are normal for people with diabetes, even with insulin injections, or people without diabetes. In some circumstances, alerting a user about glycemic excursions of which they are already aware may lead to frustration and desensitization of the alarms. It may be preferable to wait and determine whether the host's glycemic excursion follows a normal course of recovery before alerting them. Accordingly, in some embodiments, the processor module may be configured to provide output associated with a first alert state after waiting a predetermined time period, wherein the output is based on the data associated with the host's hyperglycemic condition meeting one or more second criteria after the predetermined waiting time period. Thus, it would follow that the processor module 214 may be configured to not provide output associated with the first alert state after the waiting time period based on the data associated with the host's hyperglycemic condition not meeting the one or more second criteria, thereby allowing the state to transition to the active state and back to the inactive state without alerting and/or otherwise providing output to a user. In these embodiments, the one or more first criteria and the one or more second criteria may be the same may be different and the waiting time period may be fixed or user selectable. For example, the one or more second criteria may include determine whether: the glucose level exceeds a predetermined threshold (e.g., 160, 180, 200, 220 mg/dL); the average glucose level over a predetermined time period (e.g., 10, 20, 30, 40 minutes) is more than a predetermined threshold (e.g., 160, 180, 200, 220 mg/dL); the current glucose level is more than a predetermined threshold plus a predetermined margin (e.g., 25, 50, 75 mg/dL); estimated time to a threshold (e.g., based on rate of change of glucose) and/or the rate of change of glucose is greater than a predetermined threshold (e.g., −0.5 mg/dL per minute).

Figure 9:
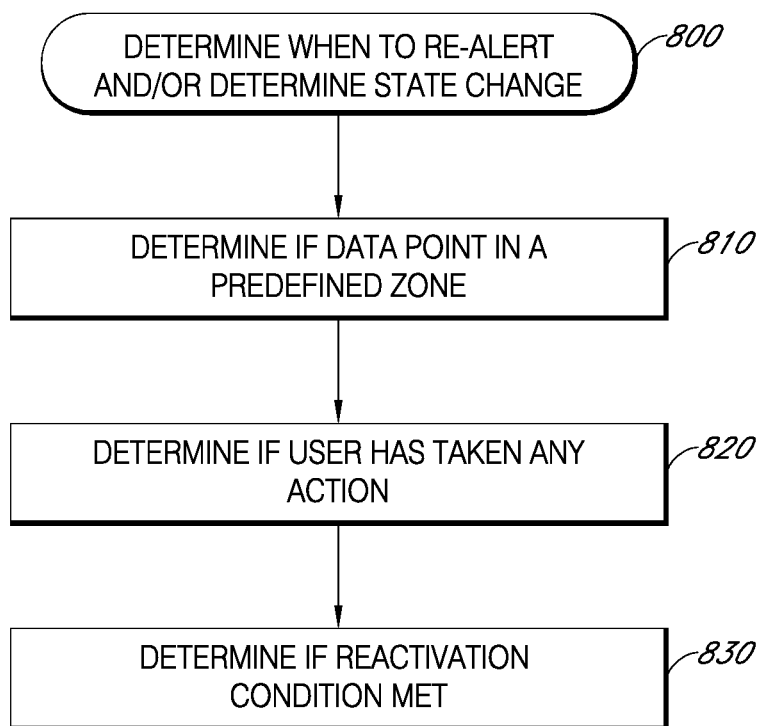
FIG. 9 is a flowchart illustrating a process for determining a status change in accordance with an embodiment of the disclosure.

FIG. 9 is a flowchart 800 illustrating an example process for determining when to re-alert and/or for determining a state transition post-alert activation from acknowledged back into an active state, also referred to as reactivation conditions, in accordance with an embodiment of the disclosure. In some embodiments, reactivation conditions have different criteria for going into an active alert state (providing alert output) as compared to an initial trigger of the active alert state, e.g., as described with reference to FIG. 6, in order to avoid unnecessary "flickering" re-alerts.

At block 810, processor module 214 may be configured to determine if one or more sensor data points is within a predetermined or predefined zone during a predetermined time period post-alert trigger, in one example embodiment. Such predetermined or predefined zone may include a region above and/or below the threshold that triggered the initial alert provided to the user. For example, referring back to FIG. 7, $TV_{Z1}$ and $TV_{Z2}$ may provide a buffer zone or envelope above and below a threshold value. In some embodiments, the predefined zone is a zone that defines a range surrounding a value that triggered the first alert. For example, the predefined zone may be 10 mg/dL above the value that triggered the first alert and/or 10 mg/dL below the value that triggered the first alert.

In some embodiments, a data point in a predefined zone is indicative of no status change. In such embodiments, no further action is performed. In embodiments utilizing state transitions, assuming the user has acknowledged the alert/alarm (or based on data analysis), the acknowledged alert state remains and no transitions to either inactive or active will occur. In contrast, if a sensor data point moves outside the zone, the state remains in acknowledged and may be actively monitored (e.g., for recovery or worsening based on certain criteria indicative of the host's glucose level trending towards or away from euglycemia), or for transition to inactive if the sensor data moves towards euglycemia based on a second (more stringent that first) one or more criteria, or transitions to active (e.g., reactivation if the sensor data moves away from euglycemia based on additional one or more reactivation criteria). For example, if the user transitions from the acknowledged state to the active state, the user may be re-alerted.

At block 820, processor module 214 also may be optionally configured to determine if a user has acknowledged an alert, as described in more detail elsewhere herein, whereby alerts or alarms are not provided to a user for a set time period, e.g. 30 minutes. In some embodiments, processor module 214 may be configured to determine if a user has taken some sort of action independent of the sensor during the predetermined time period post-alert trigger. For example, the user may have eaten or increased insulin since the initial alarm, which would likely lead to a noticeable change in glucose levels. The user may or may not input this type of information on the sensor. However, certain types of changes, e.g., insulin update, may have identifiable patterns that the processor module 214 may be able to determine was a user action, such as a change in glucose level, direction, rate of change, or acceleration/deceleration.

At block 830, processor module 214 may be configured to determine if a reactivation condition has been met by one or more sensor data points. As used herein, a "reactivation condition" refers to a condition that would cause an alert or alarm to be provided to the user after the initial alert, during the "acknowledged time period" when a user isn't expected to receive additional unnecessary alerts (e.g., a state transition from the acknowledged state to active state). Generally speaking, the reactivation condition will more likely than not relate to alarms for events considered to be dangerous to a user's health, e.g., a severe hypoglycemic event. In some embodiments, a reactivation condition may be thought of as a condition or event that would cause a host or user to change from acknowledged into an active state, as discussed with respect to FIG. 11.

Additionally, because the reactivation may have been unexpected or responsive to an attempt to suppress, the output associated with the reactivation may be more noticeable or different from other alarms, for example, by displaying explanatory information or questions of actions taken and/or by escalating the alarms as may be appreciated by one skilled in the art.

Figure 10:
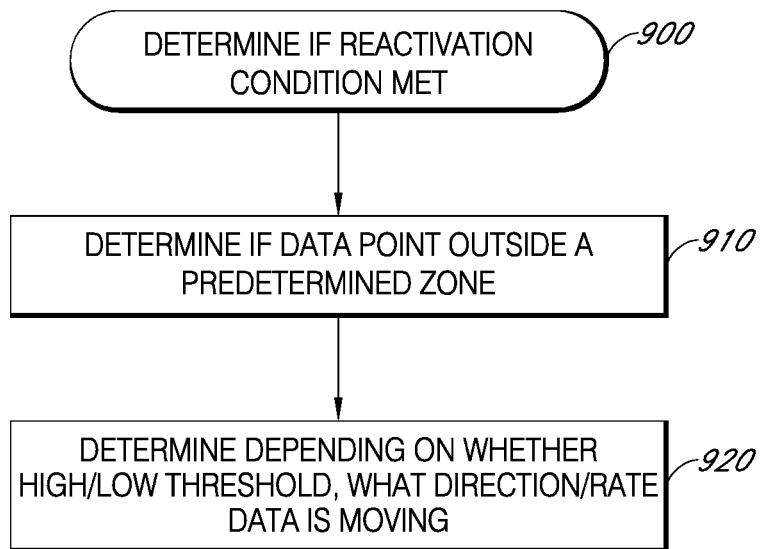
FIG. 10 is a flowchart illustrating a process for determining if a reactivation condition is met in accordance with an embodiment of the disclosure.

FIG. 10 is a flowchart 900 illustrating an example process for determining if a reactivation condition is met in accordance with an example embodiment of the disclosure. At block 910, processor module 214 may be configured to determine if one or more sensor data points is outside a predetermined or predefined zone. For example, as shown in FIG. 7, there may be regions or zones that data points seem to oscillate around after an alert has been provided to a user. Once a data point is determined to fall outside this predefined zone, it may be indicative of a user's glucose level moving toward an undesirable value or in an undesirable trend (e.g., trending away from euglycemia).

At block 920, processor module 214 may be configured to determine, depending on whether the data point has a high or low value, e.g. is within a range of the high or low threshold indicative of a hyperglycemic event or a hypoglycemic event, respectively, what direction and/or rate the data is moving or trending. Additionally, in some embodiments, the processor module 214 may be further configured to consider user input and/or insulin information as variables in assessing whether or not a reactivation condition has been met.

As may be appreciated, having a reactivation condition may also be thought of as intelligent acknowledged conditions, because it limits the number of alerts that may be provided to the user following a first alert. This can help ensure that a user is not annoyed by a series of additional alerts going off after the first alert, but allows for more intelligence and safety than a simple time-based snooze. In some embodiments, data points that may be considered to qualify as reactivation conditions may be predetermined by or fixed by factory settings. Such reactivation conditions may be stored, for example, in a lookup table.

In some embodiments, reactivation is intended to re-alert users when they have taken an action that is inadequate and returned to a dangerous zone. For example, after a low threshold alert the user may eat something that starts to increase their glucose but it is not enough so their glucose drops again. It is desirable to alert the user again in this situation, but it should be distinguishable from oscillating/ annoying alarms. This may be achieved by e.g., setting criteria of glucose rising some distance above the low threshold and then falling below, or rate of change increasing to e.g., above 1 mg/dL/min and then going negative again.

In some embodiments, following the first or initial alert to the user, the user may suspend additional alerts by acknowledging the initial alert. For example, when a user or host acknowledges the initial alert, additional alerts are suspended for a time period, except for re-alert conditions. In other words, following a threshold or predictive alert, the user would not hear another threshold or predictive alert immediately after, but would instead wait for a time period, e.g., 30 minutes. In some embodiments, the suspend time is user settable. In some embodiments, the user may have a default of 30 minutes and a maximum of e.g., 2 hours for safety.

In some embodiments, a post-alert set of instructions or algorithms may be used to detect the end of a hypoglycemic and/or hyperglycemic event transition to a recovering sub-state such that re-alert only occurs if another event occurs (e.g., rise of 5 mg/dL about threshold, upward slope greater than 1 mg/dL/min, etc.). In such embodiments, this can help prevent an annoying situation of stable glucose oscillating around 80 mg/dL and setting off threshold alert over and over, as described above.

In some embodiments, alerts may be generated if the user remains in the same condition, e.g., just below 70 mg/dL, for a long period of time because the length of time hypoglycemic may also be considered a health risk.

EXAMPLES

A number of examples are provided below. When referring to a "low" threshold, it should be understood that the low threshold relates generally to a low glucose value that may be indicative of a hypoglycemic event. Similarly, when referring to a "high" threshold, it should be understood that the high threshold relates generally to a high glucose value that may be indicative of a hyperglycemic event. As used herein, the glucose values may be estimated glucose values (EGVs) or any known type of glucose indicator or sensor data.

It should be appreciated that the following examples may be implemented according to the flow charts described above. The examples relate to specific implementations and are provided for a more in-depth understanding of how the disclosed processes can operate. The examples should not be construed as limiting, but rather as a general guide on how certain aspects may be performed.

Example 1: Low Threshold Alert

In this example, the processor module may be configured to receive sensor data (510) and evaluate the sensor data using a first function (520) to determine whether the "real-time" glucose value has crossed a first threshold (80 mg/dL) and using a second function (530) to determine whether the predicted glucose value will cross a second threshold (55 mg/dL) within 15 minutes (PH). The processor module may be configured to actively monitor data (710) associated with glycemic condition after a hypoglycemic indicator has been triggered based on the first or second function to determine whether a state change transition should occur. In this example, the following three inactivation conditions exist (to transition from active or acknowledged to inactive): 1) if the glucose value increases by more than a predetermined amount (15 mg/dL) and the glucose value is above the first threshold (80 mg/dL) since activation of the hypoglycemic indicator; 2) the rate of change of glucose is increasing at a rate greater than a predetermined value (1 mg/dL/min); and 3) the acknowledged time period is over (30 minutes).

Scenario A—Glucose Level is More than a Low Threshold

In this scenario, a hypoglycemic indicator is triggered based on the first function (host's glucose goes below 80 mg/dL), and the user is alerted via a user interface (visually and audibly). The user acknowledges the alert by pressing a button and the state transitions to the acknowledged state. In the acknowledged state, the processor module actively monitors the host's glycemic condition as the glucose value goes down to 65 mg/dL, then starts coming back up and reaches 75 mg/dL, but then starts falling again. In this example, the acknowledged state will remain for 30 minutes during which the user will not receive any additional alerts, during active monitoring the processor module determined the user's glucose to be recovering (coming back up and reaching 75 mg/dL), which triggered the recovering sub-state of acknowledged. The user will not be alerted until his/her glucose reaches a reactivation or inactivation condition. In the acknowledged state, recovering sub-state, criteria for re-alert may include any condition indicative of a glucose "rebound." Advantageously, the recovering sub-state takes advantage of the fact that some user interaction was detected, thus it can be assumed that the user has attempted to treat him/herself and should be re-alerted only if the user's action was not sufficient and a rebound (e.g., predetermined reversal of trend or worsening of glucose) is detected. In this scenario, the state transitioned back to active when the glucose started falling again (i.e., based on reactivation conditions), and the user was re-alerted.

Scenario B—Glucose Level Oscillating Around the Threshold

In this scenario, a hypoglycemic indicator is triggered based on the first function (host's glucose goes below 80 mg/dL), and the user is alerted via a user interface (visually and audibly), but this time the host's glucose stays in the range 70-90 mg/dL going above and below 80 mg/dL several times. Once the user acknowledges the alert, the acknowledged state is maintained and the user will not get any alerts until the acknowledged time is over. In other words, the states do not transition back and forth from active to inactive, causing re-alerts as the user oscillates above and below 80 mg/dL. Advantageously, this avoids annoying alerts by allowing for some buffer to avoid flickering of the alert off and on. If the user does not acknowledge, there may be re-alerts every 5 minutes (maintains in active state until acknowledged by the user). However, it is important to note that the alert is not a conventional "threshold" alert. Instead, it is an "early warning" alert and as a result warning the user of the condition is reasonable. After the acknowledged time is expired, the state will transition to either or active or inactive depending on whether the alert conditions are still met. The state will transition to active and the alert may be shown only if the EGV is still below the threshold of 80 mg/dL (e.g., if the acknowledged time is 30 minutes and after 30 minutes, the EGV is 75 mg/dL, the user will get an alert). The state will transition to inactive and the user will not get an alert if the EGV is 85 mg/dL (unless the fall rate predicted is enough to trigger the alert).

Scenario C—Prediction Followed by Crossing the Threshold

In this case, the user's glucose value is 100 mg/dL, and is predicted to reach 55 mg/dL in 15 minutes as determined by the second function (530). The active state is triggered and the alert is displayed to the user (according to block 550). Once the user acknowledges, the acknowledged state is maintained until the glucose value falls to 80 mg/dL (the low threshold) in 10 minutes, at which time the state remain as acknowledged as the host's glucose remains around 80 mg/dL for 20 minutes. Notably, no alert will be triggered when 80 mg/dL is reached (acknowledged state maintained), the state will transition back to active after 30 min if the threshold condition is met.

Example 2: Actionable Alerts Associated with Hyperglycemic Conditions

Advantageously, the user may be alerted only when it is likely that a user action is necessary. In one such example, the user may still be alerted as soon as the glucose value crosses an alert threshold. However, a user may also select to enable the wait time under certain conditions, for example, when a hyperglycemic excursion is correlated with known meal ingestion. In some embodiments, whether or not the wait time is enabled, annoying repeated alerts when the glucose value oscillates around the threshold may be minimized or eliminated, while ensuring that if the glucose value crosses the threshold twice due to reasons that are likely not related, then the user is alerted. For example, the user may be alerted once after the glucose value goes high due to carbohydrate intake (hyperglycemic alert) or not at all. Then the user takes insufficient amount of insulin, which causes the glucose value to go down a little bit, but comes back up once more.

Figure 12:
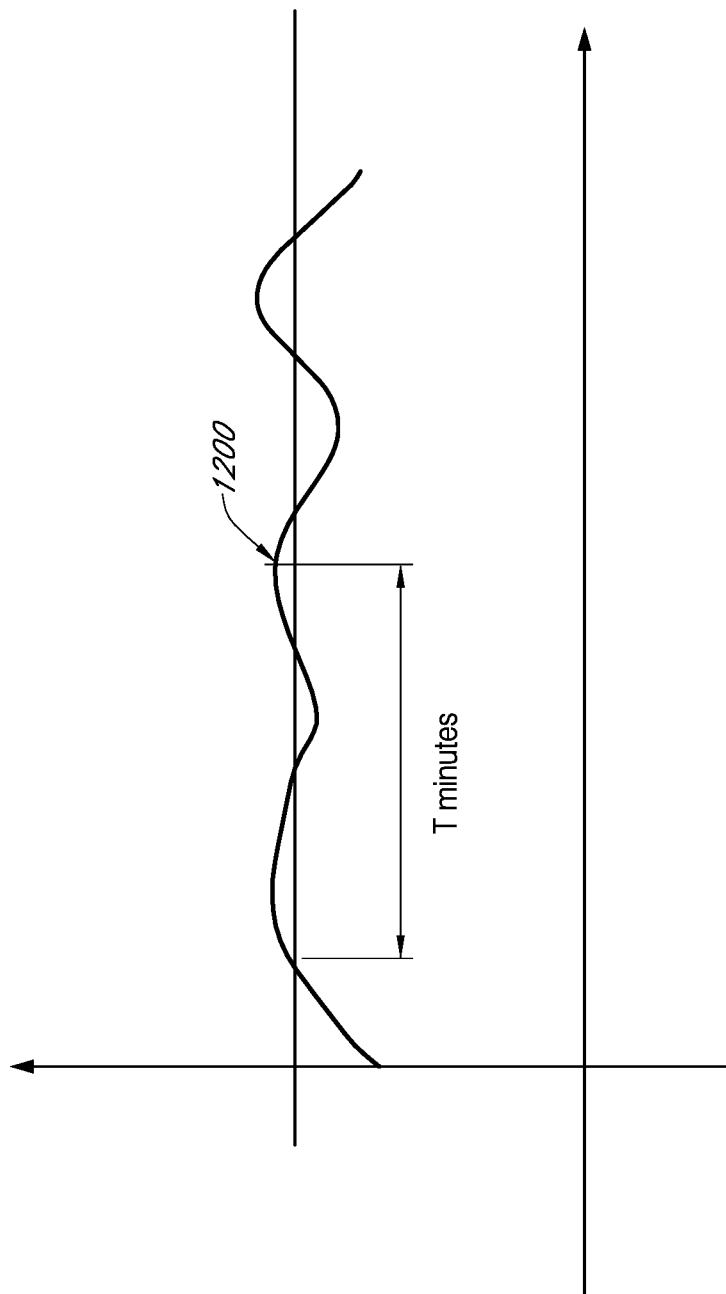
FIGS. 12-16 are example graphs showing estimated glucose values ("EGVs") and when alerts would be expected to be provided for the EGVs in accordance with embodiments of the disclosure.

FIG. 12 is an example graph showing average EGV is high over last T minutes. Notably, the user's glucose level crossed the predetermined hyperglycemic threshold at the beginning of T minutes, and the processor module transitioned to the active state 700 based on the (first) active transition criteria of the glucose level exceeding a first predetermined hyperglycemic threshold level of 180 mg/dL, thereby triggering the dynamic and intelligent monitoring of the host's glycemic condition. However, the user was not alerted because the user had enabled a predetermined wait time period (T) of 60 minutes before high alert. During the 60 minutes, the processor module actively monitored the host's glycemic condition using one or more hyperglycemic (second) criteria based on the average glucose over the predetermined wait time period, after which the glucose level was determined to be greater than the predetermined threshold level (180 mg/dL), resulting in output associated with the alert at 1200. In this case, the active state was initiated based on the first criteria (glucose level exceeding a threshold), but the alert was not provided to the user until the second criteria was met (based on average glucose level over the wait time exceeding a threshold).

Figure 13:
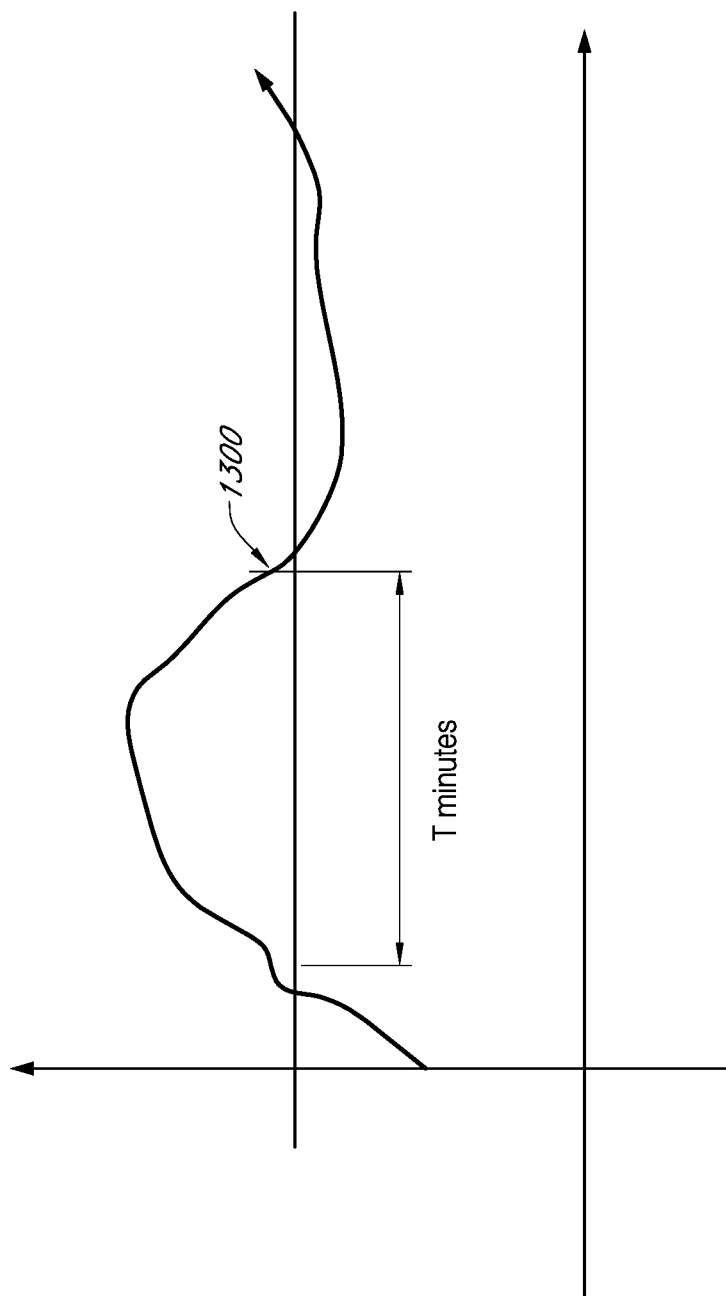

FIG. 13 is example graph showing average glucose is high, but falling rapidly, thus no alert is provided to the user or host because, although the average glucose level is high, the glucose level is falling rapidly. Notably, the user's glucose level crossed the predetermined hyperglycemic threshold at the beginning of T minutes, and the processor module transitioned to the active state 700 based on the (first) active transition criteria of the glucose level exceeding a first predetermined hyperglycemic threshold level of 180 mg/dL, thereby triggering the dynamic and intelligent monitoring of the host's glycemic condition. However, the user was not alerted because the user had enabled a predetermined wait time period (T) of 60 minutes before high alert. During the 60 minutes, the processor module actively monitored the host's glycemic condition using one or more hyperglycemic (second) criteria based on the rate of change of the glucose level, which was determined to be dropping a rate greater than the predetermined value (1 mg/dL/min), resulting in no output at 1300. In this case, the active state was initiated based on the first criteria (glucose level exceeding a threshold), but the processor module determined a state transition to inactive at 1300.

In some embodiments, the activation condition may include a time criteria or time component, meaning that a user's glucose has to exceed a threshold on average over a predetermined period of time, e.g., 60 minutes. As applied to the example shown in FIG. 13, the processor module may actively monitor the host's glycemic condition continuously using one or more hyperglycemic criteria based on the average glucose level and rate of change of the glucose level. In this scenario at 1300, the average glucose over 60 minutes was found to be above a predetermined threshold, however the rate of change of the glucose was determined to be dropping a rate greater than the predetermined value (1 mg/dL/min), resulting in no output at 1300. Consequently, the active state is not entered in this circumstance and no output is provided to the user.

Figure 14:
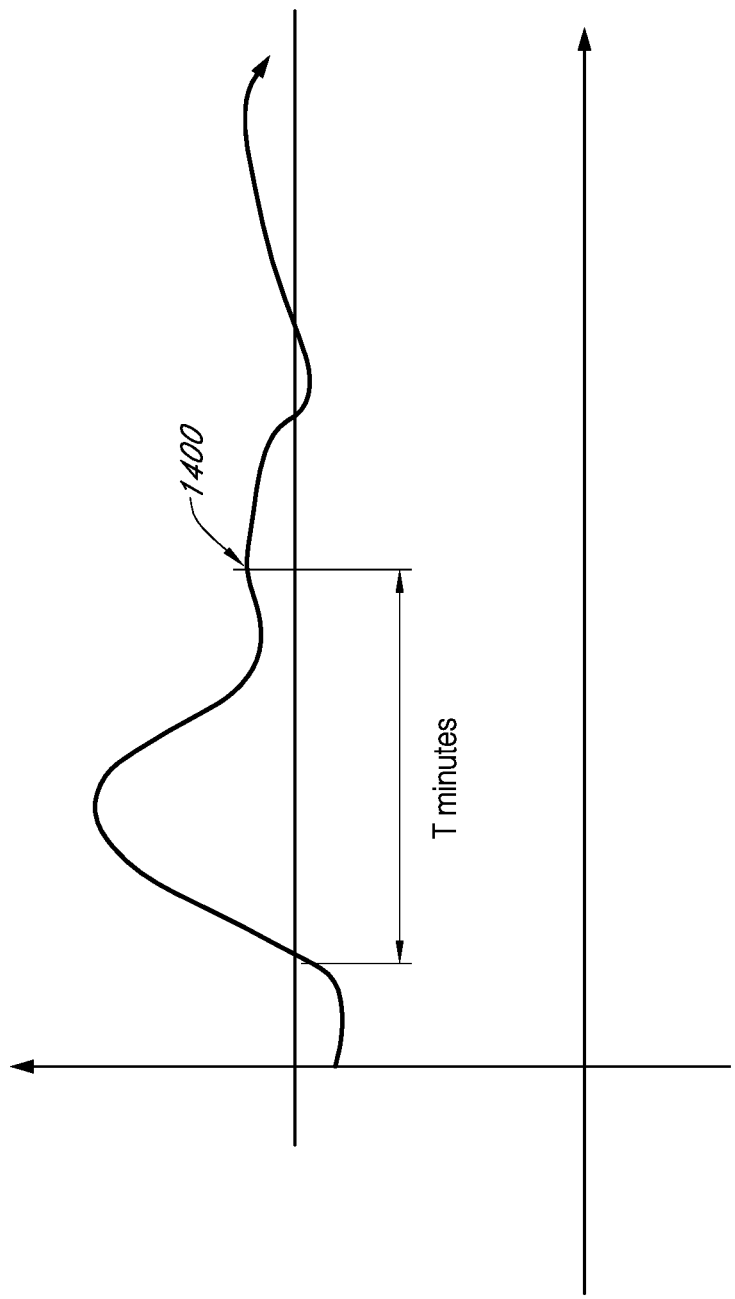

FIG. 14 is an example graph showing a high glucose level, followed by a rapid rate of change down, but then a steady glucose level still above the predetermined threshold. Notably, the user's glucose level crossed the predetermined hyperglycemic threshold at the beginning of T minutes, and the processor module transitioned to the active state 700 based on the (first) active transition criteria of the glucose level exceeding a first predetermined hyperglycemic threshold level of 180 mg/dL, thereby triggering the dynamic and intelligent monitoring of the host's glycemic condition. However, the user was not alerted because the user had enabled a predetermined wait time period (T) of 60 minutes before high alert. During the 60 minutes, the processor module actively monitored the host's glycemic condition using one or more hyperglycemic (second) criteria based on the glucose level and the rate of change of the glucose level, which at the end of the waiting period, was determined to still exceed the predetermined threshold and to have a rate of change that was not dropping faster than a predetermined rate, resulting in output at 1400. In this case, at reference numeral 1400, the user or host should be alerted here because although the glucose level fell for some time, the glucose level was steady and high (e.g., above a threshold) at the end of the wait time.

Figure 15:
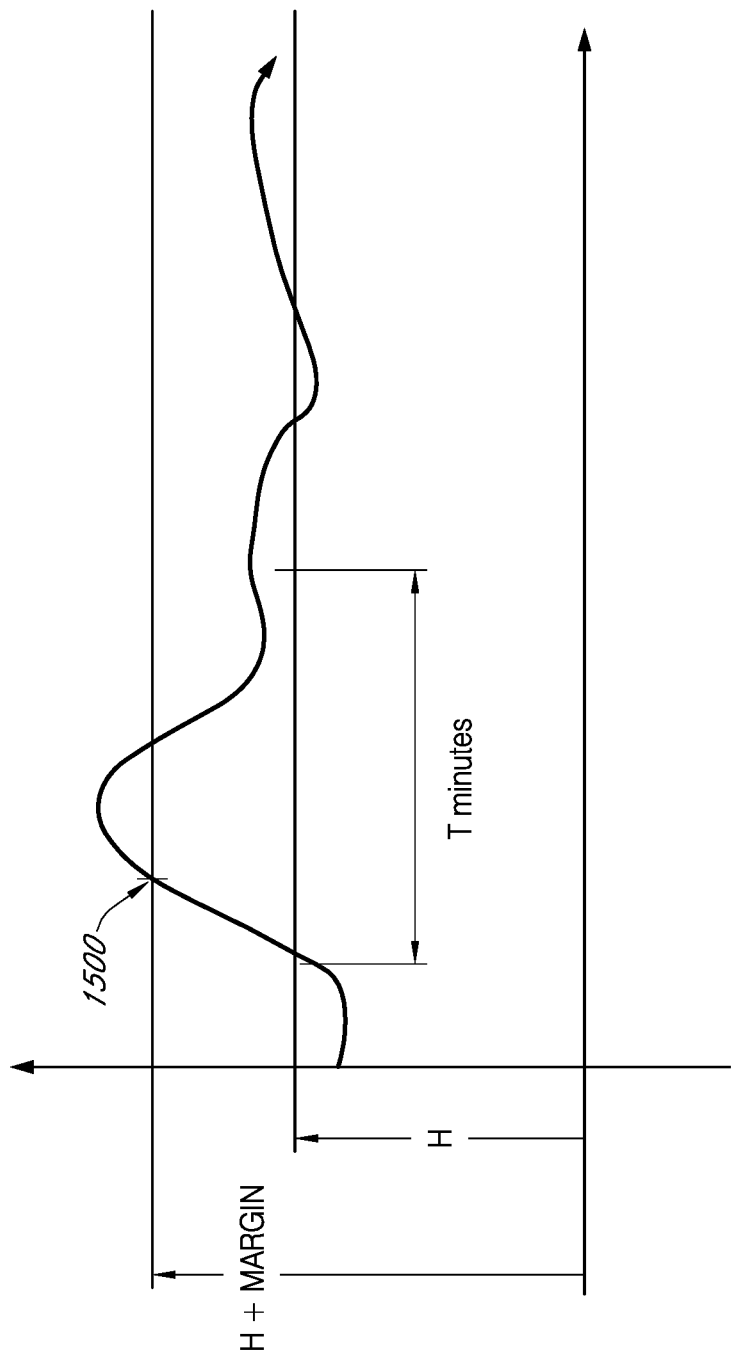

FIG. 15 is an example graph showing a host's glucose level that goes beyond the threshold plus a margin even before the wait time expires. Notably, the user's glucose level crossed the predetermined hyperglycemic threshold at the beginning of T minutes, and the processor module transitioned to the active state 700 based on the (first) active transition criteria of the glucose level exceeding a first predetermined hyperglycemic threshold level of 180 mg/dL, thereby triggering the dynamic and intelligent monitoring of the host's glycemic condition. However, the user was not alerted because the user had enabled a predetermined wait time period (T) of 60 minutes before high alert. During the 60 minutes, the processor module actively monitored the host's glycemic condition using one or more hyperglycemic (second) criteria based on the glucose level plus a margin (180 mg/dL+50 mg/dL=230 mg/dL), which occurred prior to the end of the waiting period, resulting in output at 1500 prior to the 60 minute expiration. In this case, the user or host should be alerted at 1500 because the glucose level has risen to such an extent that the no-alert waiting period should be overridden.

Figure 16:
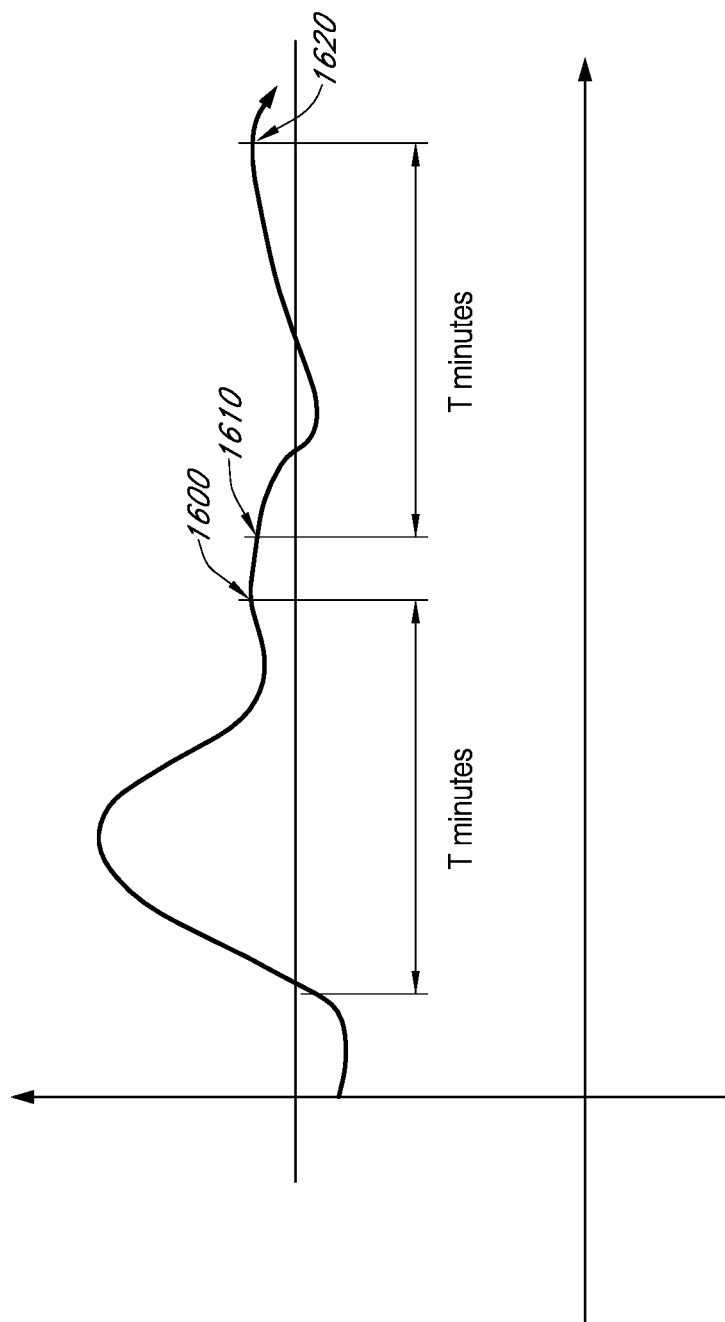

FIG. 16 is an example graph showing after user acknowledgement of an alert in a scenario similar to FIG. 14, because although the glucose level fell for some time, the glucose level was steady and high (e.g., above a threshold) at the end of the wait time. After the alert was output at 1600, the user acknowledged the alert at 1610, transitioning into the acknowledged state, which has a 60 minute active monitoring period. Notably, the user's glucose level crossed below the predetermined hyperglycemic threshold soon after the user acknowledged the alert, however not sufficiently low to inactive the alert (because the inactivation conditions included threshold plus delta criteria). Accordingly, the processor module continued to actively monitor the host's glycemic condition based on average glucose, which determined the average glucose level at something above the predetermined threshold at the end of 60 minutes. In this case, the user or host is re-alerted or provided a subsequent alert because the average EGV is still high after the acknowledgment time period 1620.

The scenarios above assume that "enable wait before alert" is turned on, however, any of those scenarios would have functioned similarly if the wait time was not enabled, but the acknowledged time period was selected by the user to be 60 minutes, in which case user would have a first alert after the first criteria were met (at the beginning of time period T) and then another one after the second criteria were met, for example at 1200, 1400, 1500 or 1600 (but not at other times in between when the user's glucose level oscillated up and down around the predetermined threshold).

This example further describes how the processor module actively monitors the host's glycemic condition after the user acknowledges a hyperglycemic alert (e.g., triggered with the host's glucose meeting one or more first or second criteria). Subsequent to the hyperglycemic alert output, the user acknowledges the alert, thus it may be assumed that the user is either watching or taking some action. The processor module transitions to acknowledged state. The processor module then actively monitors the host's glycemic condition, such that if the host's average glucose level since activation of the alert is less than the threshold (180 mg/dL) minus a delta (15 mg/dL); the host's actual (real-time) glucose level is less than the threshold minus the delta (165 mg/dL); average glucose level since activation of the alert is less than the predetermined threshold and the acknowledged time has expired; or rate of change of the host's glucose level falls faster than a predetermined rate (e.g., 1.0 mg/dL/min) and the glucose level is less than a threshold, predetermined meal information is received or confirmed; or predetermined insulin delivery information is received or confirmed, then the processor module would transition to inactive based on those inactivation criteria.

The disclosure presents the best mode contemplated for carrying out the present systems and methods for processing analyte sensor data, and of the manner and process of practicing them, in such full, clear, concise, and exact terms as to enable any person skilled in the art to which they pertain to practice these systems and methods. These systems and methods are, however, susceptible to modifications and alternate constructions from those discussed above that are fully equivalent.

For example, it should further be appreciated that the implementation and/or execution of all methods and processes may be performed by any suitable devices or systems, whether local or remote. Further, any combination of devices or systems may be used to implement the present methods and processes. Additionally, in some embodiments, the methods and processes described herein may reside in a non-transitory computer-readable storage medium including code which when executed by at least one processor causes operations of the present disclosure to be realized.

Furthermore, although the foregoing has been described in some detail by way of illustrations and examples for purposes of clarity and understanding, it is apparent to those skilled in the art that certain changes and modifications may be practiced. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated. Therefore, the description and examples should not be construed as limiting the scope of the disclosure to the specific embodiments and examples described herein, but rather to also cover all modification and alternatives coming with the true scope and spirit of the disclosure.

What is claimed is:

1. A method of activating hypoglycemic indicators based on continuous glucose sensor data, the method comprising:
    evaluating sensor data using a first function to determine whether a real time glucose value meets one or more user settable first criteria;
    evaluating sensor data using a second function to determine whether a parameter indicative of glucose value meets one or more non user settable second criteria;
    providing an output including a first hypoglycemic indicator if the one or more user settable first criteria is met, and providing an output including a second hypoglycemic indicator if the one or more non user settable second criteria are met.

2. The method of claim 1, wherein the evaluating sensor data using a first function to determine whether a real time glucose value meets one or more user settable first criteria comprises determining whether the real-time glucose value passes a glucose threshold.

3. The method of claim 2, wherein the evaluating sensor data using a first function to determine whether a real time glucose value meets one or more user settable first criteria further comprises determining whether an amplitude of rate of change or direction of rate of change meets a rate of change criterion.

4. The method of claim 1, wherein the evaluating sensor data using a first function to determine whether the real time glucose value meets one or more user settable first criteria comprises evaluating a static risk of a substantially real time glucose value.

5. The method of claim 1, wherein the evaluating sensor data using a second function to determine whether the parameter indicative of glucose value meets one or more second criteria comprises evaluating a dynamic risk of the predicted glucose value.

6. The method of claim 1, wherein the second function comprises an artificial neural network model that uses at least one of exercise, stress, illness or surgery to determine the parameter indicative of glucose value, and wherein the parameter is a predicted glucose value.

7. The method of claim 1, wherein the second function utilizes a first order autoregressive model to determine the parameter indicative of glucose value, and wherein the parameter is a predicted glucose value.

8. The method of claim 7, wherein the first order autoregressive model comprises a parameter alpha, and wherein alpha is estimated recursively each time a sensor data point is received.

9. The method of claim 1, wherein evaluating the sensor data using the first function and the second function allows for increased warning time of hypoglycemic alerts without substantially increasing the number of alerts as compared to evaluating the sensor data using the first function without evaluating the sensor data using the second function.

10. The method of claim 1, wherein the one or more user settable first criteria comprises a first threshold that is configured to be user settable.

11. The method of claim 10, wherein the one or more non user settable second criteria comprises a second threshold that is not user settable.

12. The method of claim 1, wherein the hypoglycemic indicator comprises a flag that has a particular set of instructions associated with it depending on whether the hypoglycemic indicator was activated based on the first function meeting the one or more user settable first criteria or whether the hypoglycemic indicator was activated based on the second function meeting the one or more non user settable second criteria.

13. The method of claim 1, wherein the output comprises at least one of an audible, tactile or visual output, and wherein the output is differentiated and/or provides information selectively based on whether the hypoglycemic indicator was activated based on the first function meeting the one or more user settable first criteria or whether the hypoglycemic indicator was activated based on the second function meeting the one or more non user settable second criteria.

14. The method of claim 1, wherein providing an output comprises transmitting a message to an insulin delivery device including instructions associated with at least one of: a) suspending insulin delivery, b) initiating a hypoglycemia and/or hyperglycemia minimizer algorithm, c) controlling insulin delivery or d) information associated with the hypoglycemia indicator.

15. The method of claim 1, wherein the one or more non user settable second criteria are programmed at the factory in such a way that no user is able to modify the second criteria.

16. The method of claim 1, wherein the user is a host or a healthcare provider.

17. The method of claim 1, wherein the second function provides no more than one additional alarm per week based on a retrospective analysis comparing the use of the first function and the second function together as compared to the first function alone.

18. The method of claim 1, wherein evaluating the sensor data using the first function and the second function provides increased warning time of hypoglycemic alerts without substantially increasing the number of alerts as compared to evaluating the sensor data using the first function without evaluating the sensor data using the second function.

19. A system for processing data, the system comprising:
a continuous analyte sensor configured to be implanted within a body; and
sensor electronics configured to receive and process sensor data output by the sensor, the sensor electronics including a processor configured to:
evaluate sensor data using a first function to determine whether a real time glucose value meets one or more user settable first criteria;
evaluate sensor data using a second function to determine whether a parameter indicative of a glucose value meets one or more non-user settable second criteria;
activate a first hypoglycemic indicator if the one or more user settable first criteria is met and activate a second hypoglycemic indicator if the one or more non user settable second criteria are met; and
provide an output based on the activated hypoglycemic indicator.

20. The system of claim 19, wherein evaluating the sensor data using the first function and the second function allows for increased warning time of hypoglycemic alerts without substantially increasing the number of alerts as compared to evaluating the sensor data using the first function without evaluating the sensor data using the second function.

21. The system of claim 19, wherein the one or more user settable first criteria comprises a first threshold that is configured to be user settable.

22. The system of claim 19, wherein the one or more non user settable second criteria comprises a second threshold that is not user settable.

23. The system of claim 19, wherein the hypoglycemic indicator comprises a flag that has a particular set of instructions associated with it depending on whether the hypoglycemic indicator was activated based on the first function meeting the one or more user settable first criteria or whether the hypoglycemic indicator was activated based on the second function meeting the one or more non user settable second criteria.

24. The system of claim 19, wherein the output comprises at least one of an audible, tactile or visual output, and wherein the output is differentiated and/or provides information selectively based on whether the hypoglycemic indicator was activated based on the first function meeting the one or more user settable first criteria or whether the hypoglycemic indicator was activated based on the second function meeting the one or more non user settable second criteria.

25. The system of claim 19, wherein providing output comprises transmitting a message to an insulin delivery device including instructions associated with at least one of: a) suspending insulin delivery, b) initiating a hypoglycemia and/or hyperglycemia minimizer algorithm, c) controlling insulin delivery or d) information associated with the hypoglycemia indicator.

26. The system of claim 19, wherein the one or more non user settable second criteria are programmed at the factory in such a way that no user is able to modify the non user settable second criteria.

27. The system of claim 19, wherein the user is a host or a healthcare provider.

28. The system of claim 19, wherein the second function provides no more than one additional alarm per week based on a retrospective analysis comparing the use of the first function and the second function together as compared to the first function alone.

29. The system of claim 19, wherein the evaluation of the sensor data using the first function and the second function provides increased warning time of hypoglycemic alerts without substantially increasing the number of alerts as compared to evaluation of the sensor data using the first function without evaluation of the sensor data using the second function.

\* \* \* \* \*

UNITED STATES PATENT AND TRADEMARK OFFICE
CERTIFICATE OF CORRECTION

PATENT NO. : 10,702,215 B2
APPLICATION NO. : 16/674979
DATED : July 7, 2020
INVENTOR(S) : Hari Hampapuram Page 1 of 2

It is certified that error appears in the above-identified patent and that said Letters Patent is hereby corrected as shown below:

On the Title Page

On Page 3, Column 2, Item (56), Line 25, under Other Publications, delete "devconvolution-" and insert --deconvolution- --.

In the Specification

In Column 1, Line 38, delete "Type I" and insert --Type 1--.

In Column 5, Line 24, delete "the a" and insert --the--.

In Column 6, Line 30, delete "the a" and insert --the--.

In Column 23, Line 53, delete "nighttime)," and insert --night time),--.

In Column 25, Line 59, delete "voL" and insert --vol--.

In Column 31, Line 37, delete "hosts'" and insert --host's--.

In Column 32, Line 9, delete "hosts'" and insert --host's--.

In Column 34, Line 38, delete "hosts'" and insert --host's--.

In Column 36, Line 37, delete "parents'" and insert --parent's--.

In Column 36, Line 43, delete "based" and insert --based on--.

In Column 36, Line 46, delete "the a" and insert --the--.

In Column 36, Line 56, delete "(except" and insert --except--.

Signed and Sealed this
Twenty-second Day of September, 2020

Andrei Iancu
*Director of the United States Patent and Trademark Office*

In Column 39, Line 47, delete "(e.g.," and insert --e.g.,--.

In the Claims

In Column 50, Line 12, Claim 19, delete "non-user" and insert --non user--.